United States Patent
Schunck et al.

(10) Patent No.: US 10,287,262 B2
(45) Date of Patent: *May 14, 2019

(54) EICOSANOID DERIVATIVES

(71) Applicants: Max-Delbrueck-Centrum fuer Molekulare Medizin, Berlin (DE); Board of Regents of University of Texas System, Austin, TX (US)

(72) Inventors: Wolf-Hagen Schunck, Berlin (DE); Gerd Wallukat, Berlin (DE); Robert Fischer, Berlin (DE); Cosima Arnold, Ulm (DE); Dominik N. Mueller, Berlin (DE); Narender Puli, Dallas, TX (US); John R. Falck, Dallas, TX (US)

(73) Assignees: MAX-DELBRUECK-CENTRUM FUER MOLEKULARE MEDIZIN, Berlin (DE); BOARD OF REGENTS OF UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,354

(22) Filed: Jan. 27, 2016

(65) Prior Publication Data
US 2016/0326128 A1 Nov. 10, 2016

Related U.S. Application Data

(63) Continuation of application No. 13/144,301, filed on Feb. 1, 2012, now Pat. No. 9,272,991.

(51) Int. Cl.
| | |
|---|---|
| *C07C 275/16* | (2006.01) |
| *C07C 233/09* | (2006.01) |
| *C07C 233/49* | (2006.01) |
| *C07C 235/28* | (2006.01) |
| *C07C 275/14* | (2006.01) |
| *C07C 233/47* | (2006.01) |
| *C07D 303/38* | (2006.01) |
| *C07C 235/76* | (2006.01) |
| *C07C 275/20* | (2006.01) |

(52) U.S. Cl.
CPC .......... *C07D 303/38* (2013.01); *C07C 233/09* (2013.01); *C07C 233/47* (2013.01); *C07C 233/49* (2013.01); *C07C 235/28* (2013.01); *C07C 235/76* (2013.01); *C07C 275/14* (2013.01); *C07C 275/16* (2013.01); *C07C 275/20* (2013.01)

(58) Field of Classification Search
CPC ... C07C 275/16; C07C 233/09; C07C 233/49; C07C 235/28; C07C 275/14; C07C 233/47; C07D 303/38
See application file for complete search history.

(56) References Cited

U.S. PATENT DOCUMENTS

| | | | |
|---|---|---|---|
| 5,753,702 A | 5/1998 | Bednar et al. | |
| 8,658,632 B2* | 2/2014 | Brostrom | C07C 233/09 514/183 |
| 9,272,991 B2* | 3/2016 | Schunck | C07C 233/47 |
| 2002/0035095 A1 | 3/2002 | Klimko et al. | |
| 2002/0049244 A1* | 4/2002 | Roman | A61K 31/00 514/381 |
| 2002/0151734 A1 | 10/2002 | Schwartzman et al. | |
| 2008/0095711 A1 | 4/2008 | Falck et al. | |
| 2008/0146663 A1 | 6/2008 | Imig et al. | |
| 2008/0306155 A1 | 12/2008 | Roman et al. | |

FOREIGN PATENT DOCUMENTS

WO 2004080389 A2 9/2004

OTHER PUBLICATIONS

Yu et al. Bioorganic & Medicinal Chemistry 2003, 11, 2803-2821.*
Jatoi et al. Critical Reviews in Oncology/Hematology 2005, 55, 37-43.*
Larsson et al. Am. J. Clin. Nutr. 2004, 79, 935-45.*
Yonezawa et al. Biochemical Pharmacology 2005, 70, 453-460.*
WebMD, Diabetes Health Center, Prevention, obtained from http://www.webmd.com/diabetes/guide/type-1-diabetes-prevention on Apr. 5, 2015.*
WebMD, Crohn's Disease Health Center, Crohn's Disease-Prevention, obtained from http://www.webmd.com/ibd-crohns-disease/crohns-disease/tc/crohns-disease-prevention on Apr. 5, 2015.*
Luo et al. Cell, 2009, 136, pp. 823-837.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
CAS Registry No. 110064-75-0, which entered STN on Aug. 29, 1987.*
Romanov, Stepan G. et al., "Total synthesis of (5Z,8Z,11Z,14Z)-18- and 19-oxoeicosa-5,8,11,14-tetraenoic acids", Tetrahedron, 2002, 58, pp. 8483-8487.
Dussault, Patrick et al., "A Chemoenzymic Approach to Hydroperoxyeicosatetraenoic Acids. Total Synthesis of 5 (S)-HPETE", J. Org. Chem., 1995, 60, pp. 218-226.

(Continued)

*Primary Examiner* — Matthew P Coughlin
(74) *Attorney, Agent, or Firm* — Agris & Von Natzmer, LLP; Joyce Von Natzmer

(57) ABSTRACT

The present invention provides compounds (n-3 PUFA derivatives) of formula (I):

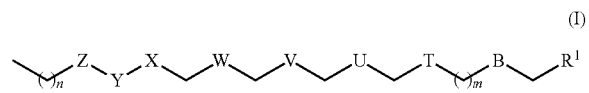

that modulate conditions associated with cardiac damage, especially cardiac arrhythmias.

13 Claims, 8 Drawing Sheets

(56) References Cited

OTHER PUBLICATIONS

Falck, J. R. et al., "11,12-Epoxyeicosatrienoic Acid (11,12-EET): Structural Determinants for Inhibition of TNF-alpha-Induced VCAM-1 Expression" in: Bioorganic & Medicinal Chemistry Letters, 13(22), 2003, pp. 4011-4014.

Falck, J. R. et al. "Comparison of vasodilatory properties of 14,15-EET analogs: structural requirements for dilation" in: Am J Physiol Heart Circ Physiol, No. 284, pp. H337-H349, 2003, (First published Sep. 19, 2002).

Yang, Wenqi et al.: "Stable 5,6-Epoxyeicosatrienoic Acid Analog Relaxes Coronary Arteries Through Potassium Channel Activation" in: Hypertension, 2005, No. 45, pp. 681-686.

Kang, Jing X. & Leaf, Alexander, 2000: Prevention of fatal cardiac arrhythmias by polyunsaturated fatty acids1'2'3, in:THe American Journal of Clinical Nutrition, vol. 71, No. 1, 202S-207S.

Li, Yunyuan; Kang, Jing X. & Leaf, Aleander, 1997: Differential Effects of Various Eicosanoids on the Production or Prevention of Arrhythmias in Cultured Neonatal Rat Cardiac Myocytes, Prostaglandins 54: 511-530.

Yi, Xiu-Yu et al: "Metabolism of adrenic acid to vasodilatory 1.alpha.,1.beta.-dihomo-epoxyeicosatrienoic acids by bovine coronary arteries" in American Journal of Physiology, No. 292, 2007, pp. H2265-H2274.

Zhang, Yongde et al: "EET homologs potently dilate coronary microvessels and activate BKCa Channels" in: American Journal of Physiology, No. 280, 2001, pp. H2430-H2440.

Falck, J. R. et al: "14,15-Epoxyeicosa-5,8,11-trienoic Acid (14,15-EET) Surrogates Containing Epoxide Bioisosteres: Influence upon Vascular Relaxation and Soluble Epoxide Hydrolase Inhibition" in: Journal of Medicinal Chemistry , 52(16), vol. 52, 2009, pp. 5069-5075.

Database CA [Online] Chemical Abstracts Service, Columbus, Ohio, US; 1992, Ali, M. et al: "A new hydroxyketone from the seeds of Musa balbisiana" retrieved from STN Database accession No. 1992: 55570, XP002578647.

Database CA [Online] Chemical Abstracts Service, Columbus, Ohio, US; 1976, Aliev, E. E. et al: "Relation between the chain-length of the hydrocarbon radical and the inhibitory efficiency of organic amide Compounds" retrieved from STN Database accession No. 1976:596754, XP002578648.

Database CA [Online] Chemical Abstracts Service, Columbus, Ohio, US; 1968, Durrani, Aziz A. et al: "Chemical examination of Scirpus tuberosus. l" retrieved from STN Database accession No. 1968:10218, XP002578649.

Database CA [Online] Chemical Abstracts Service, Columbus, Ohio, US; 2005, Yu, Quanwei et al: "Lyotropic and Thermotropic Phase Transitions in Films of Ionene-Alkyl Sulfate Complexes" retrieved from STN Database accession No. 2005:539357, XP002578650.

Database CA [Online] Chemical Abstracts Service, Columbus, Ohio, US; 1979, Tiwari, K.P. et al: "Methyl 19-ketotetracosanoate from Pavonia zeylanica Cav" retrieved from STN Database accession No. 1979:607389, XP002578651.

Database CA [Online] Chemical Abstracts Service, Columbus, Ohio, US; 1985, Gupta, Madan M. et al: "Oxo fatty acids from Cryptocoryne sprialis rhizomes" retrieved from STN Database accession No. 1985:42833, XP002578652.

Database CA [Online] Chemical Abstracts Service, Columbus, Ohio, US; 1978, Tiwari, K. P. et al: "Methyl 19-ketodocosanoate from Berberis acanthifolium" retrieved from STN Database accession No. 1978:611923, XP002578653.

Database CA [Online] Chemical Abstracts Service, Columbus, Ohio, US; 1994, Boggs, J. M. et al: "Do the long fatty acid chains of sphingolipids interdigitate across the center of a bilayer of shorter chain Symmetrie phospholipids?" retrieved from STN Database accession No. 1994:157109, XP002578654.

Database CA [Online] Chemical Abstracts Service, Columbus, Ohio, US; 1996, Weinbach, Susan P. et al: "Elucidation of Multilayer Growth of Amphiphiles on Liquid Surfaces" retrieved from STN Database accession No. 1996:256414, XP002578655.

Database CA [Online] Chemical Abstracts Service, Columbus, Ohio, US; 1985, Wu, Naiju et al: "Studies on chemical constituents of Shi Mang Cao (Polygonum capitatum)" retrieved from STN Database accession No. 1985:476116, XP002578656.

Database CA [Online] Chemical Abstracts Service, Columbus, Ohio, US; 1990, Iyer, R. R. et al: "Convergent approaches to the syntheses of long-chain aliphatic hydroxy ketones: potential bioactive Compounds of plant origin" retrieved from STN Database accession No. 1990:178456, XP002578657.

Database CA [Online] Chemical Abstracts Service, Columbus, Ohio, US; 1998, Gupta, Jyoti et al: "Phytoconstituents of *Capparis decidua* root barks" retrieved from STN Database accession No. 1998:810591, XP002578803.

Database CA [Online] Chemical Abstracts Service, Columbus, Ohio, US; 1969, SIH, Charles J. et al: "General biochemical synthesis of oxygenated Prostaglandins E" retrieved from STN Database accession No. 1969:427478, XP002578804.

Database CA [Online] Chemical Abstracts Service, Columbus, Ohio, US; 1969, Jones, Derrick F. et al: "Microbiological oxidation of long-chain aliphatic Compounds. IV. Alkane derivatives having polar terminal groups" retrieved from STN Database accession No. 1969:11049, XP002578805.

Database CA [Online] Chemical Abstracts Service, Columbus, Ohio, US; 1963, Toubiana, Raoul et al: "Long-chain aliphatic substances related to bacterial lipids" retrieved from STN Database accession No. 1963:408506, XP002578806.

Database CA [Online] Chemical Abstracts Service, Columbus, Ohio, US; 1953, Ames, D. E. et al: "Synthetic long-chain aliphatic Compounds. IX. Some antituberculous long-chain amines" retrieved from STN Database accession No. 1953:6172, XP002578807.

Database, Gunstone et al: "Fatty acids. 35. Preparation and properties of the complete series of methyl epoxyoctadecanoates," Accession No. 1972:548832, XP002539497.

CAS registry entry for Registry No. 83483-64-1, which entered STN on Nov. 16, 1984.

"Expert Scientific Group on Phase One Clinical Trials Final Report" Nov. 30, 2006, pp. C35-C38.

WebMD, Crohn's Disease Health Center, Crohn's Disease-Prevention, obtained from http://www.webmd.com/ibd-crohns-diease/crohns-disease/tc/crohns-disease-prevention on Apr. 5, 2015.

\* cited by examiner

EICOSANOID DERIVATIVES

RELATED APPLICATION(S)

This is the continuation of Ser. No. 13/144,301, filed Feb. 1, 2012, which is a U.S. national stage of International application PCT/EP2010/000140, filed Jan. 13, 2010 designating the United States and claiming priority to European patent application no. EP 09000372.4, filed Jan. 13, 2009, which is incorporated herein by reference in its entirety.

STATEMENT OF GOVERNMENT SUPPORT

Work related to this patent document was funded by the U.S. government. (NIH Grant R01GM031278). The government has certain rights in the patent document.

FIELD OF THE INVENTION

The present invention relates to compounds which are analogues of polyunsaturated fatty acids (PUFAs). The present invention further relates to compositions containing one or more of these compounds and to the use of these compounds or compositions for the treatment or prevention of conditions and diseases associated with inflammation, proliferation, hypertension, coagulation, immune function, heart failure and cardiac arrhythmias.

BACKGROUND

Fatty acids are one of the most extensively studied classes of compounds due to their important role in biological systems (Ferrante, A., Hii, C. S. T., Huang, Z. H., Rathjen, D. A. In The Neutrophils: New Outlook for the Old Cells. (Ed. Gabrilovich, D.) Imperial College Press (1999) 4: 79-150; Sinclair, A., and Gibson, R. (eds) 1992. Invited papers from the Third International Congress. American Oil Chemists' Society, Champaign, Ill. 1-482). Hundreds of different fatty acids exist in nature and among them. Naturally occurring polyunsaturated fatty acids (PUFAs) contain 16 to 22 carbon atoms with two or more methylene-interrupted double bonds.

PUFAs can be divided into four families, based on the parent fatty acids from which they are derived: linoleic acid (18: 2 n-6), α-linolenic acid (18: 3 n-3), oleic acid (18: 1 n-9) and palmitoleic acid (16: 1 n-7). The n-6 and n-3 PUFAs cannot be synthesized by mammals and are known as essential fatty acids (EFAs). They are acquired by mammalian bodies indirectly through desaturation or elongation of linoleic and α-linolenic acids, which must be supplied in the diet.

EFAs have a variety of biological activities and n-3 PUFAs are required for normal human health (Spector, A. A. (1999) Lipids 34, 1-3). For instance, dietary n-3 PUFAs have effects on diverse physiological processes impacting normal health and chronic disease (for a review, see, for example, Jump, D. B. (2002) J. Biol. Chem. 277, 8755-8758), such as the regulation of plasma lipid levels (Rambjor, G. S., Walen, A. I., Windsor, S. L., and Harris, W. S. (1996) Lipid 31, 45-49; Harris, W. S. (1997) Am. J. Clin. Nutr. 65, 1645-1654; Harris, W. S., Hustvedt, B-E., Hagen, E., Green, M. H., Lu, G., and Drevon, C. A. (1997) J. Lipid Res. 38, 503-515; Mori, T. A., Burke, V., Puddey, I. B., Watts, G. F., O'Neal, D. N., Best, J. D., and Beilen, L. J. (2000) Am. J. Clin. Nutr. 71, 1085-1094), cardiovascular (Nordoy, A. (1999) Lipids 34, 19-22; Sellmayer, A., Hrboticky, N., and Weber, P. C. (1999) Lipids 34, 13-18; Leaf, A. (2001) J. Nutr. Health Aging 5, 173-178) and immune function (Hwang, D. (2000) Annu. Rev. Nutr. 20, 431-456), insulin action (Storlien, L., Hulbert, A. J., and Else, P. L. (1998) Curr. Opin. Clin. Nutr. Metab. Care 1, 559-563; Storlien, L. H., Kriketos, A. D., Calvert, G. D., Baur, L. A., and Jenkins, A. B. (1997) Prostaglandins Leukotrienes Essent. Fatty Acids 57, 379-385), and neuronal development and visual function (Salem, N., Jr., Litman, B., Kim, H-Y., and Gawrisch, K. (2001) Lipids 36, 945-959). Ingestion of n-3 PUFA will lead to their distribution to virtually every cell in the body with effects on membrane composition and function, eicosanoid synthesis, and signaling as well as the regulation of gene expression (Salem, N., Jr., Litman, B., Kim, H-Y., and Gawrisch, K. (2001) Lipids 36, 945-959; Jump, D. B., and Clarke, S. D. (1999) Annu. Rev. Nutr. 19, 63-90; Duplus, E., Glorian, M., and Forest, C. (2000) 275, 30749-30752; Dubois, R. N., Abramson, S. B., Crofford, L., Gupta, R. A., Simon, L. S., Van De Putte, L. B. A., and Lipsky, P. E. (1998) FASEB J. 12, 1063-1073).

Additionally, it has been suggested that n-3 PUFAs are important modulators of neoplastic development because they are capable of decreasing the size and number of tumours as well as the lag time of tumour appearance (Abel, S., Gelderblom, W. C. A., Smuts, C. M., Kruger M. (1997) Pros. Leuko. and Essential, 56 (1): 29-39). Intake of n-3 PUFAs has been found to be associated with a reduced incidence of coronary arterial diseases, and various mechanisms by which n-3 PUFAs act have been proposed (Krombout, D. (1992) Nutr. Rev. 50: 49-53; Kinsella, J. E., Lokesh, B., Stone R. A. (1990) Am. J. Clin. Nuer. 52: 1-28). Some n-3 PUFAs also possess antimalarial (Kumaratilake, L. M., Robinson, B. S., Ferrante, A., Poulos A. (1992) J. Am. Soc. Clin. Investigation 89: 961-967) or anti-inflammatory properties (Weber, P. C. (1990) Biochem. Soc. Trans. 18: 1045-1049).

Furthermore, one of the EFAs' most important biological roles is to supply precursors for the production of bioactive fatty acid metabolites that can modulate many functions (Arm, J. P., and Lee, T. H. (1993) Clin. Sci. 84: 501-510). For instance, arachidonic acid (AA; 20:4, n-6) is metabolized by Cytochrome P450 (CYP) enzymes to several classes of oxygenated metabolites with potent biological activities (Roman R J. P-450 metabolites of arachidonic acid in the control of cardiovascular function. Physiol Rev. 2002; 82:131-85). Major metabolites include 20-hydroxyeicosatetraenoic acid (20-HETE) and a series of regio- and stereoisomeric epoxyeicosatrienoic acids (EETs). CYP4A and CYP4F isoforms produce 20-HETE and CYP2C and CYP2J isoforms EETs.

It is known that EPA (20:5, n-3) may serve as an alternative substrate for AA-metabolizing CYP isoforms (Theuer J, Shagdarsuren E, Muller D N, Kaergel E, Honeck H, Park J K, Fiebeler A, Dechend R, Haller H, Luft F C, Schunck W H. Inducible NOS inhibition, eicosapentaenoic acid supplementation, and angiotensin II-induced renal damage. Kidney Int. 2005; 67:248-58; Schwarz D, Kisselev P, Ericksen S S, Szklarz G D, Chernogolov A, Honeck H, Schunck W H, Roots I. Arachidonic and eicosapentaenoic acid metabolism by human CYP1A1: highly stereoselective formation of 17(R), 18(S)-epoxyeicosatetraenoic acid. Biochem Pharmacol. 2004; 67:1445-57; Schwarz D, Kisselev P, Chernogolov A, Schunck W H, Roots I. Human CYP1A1 variants lead to differential eicosapentaenoic acid metabolite patterns. Biochem Biophys Res Commun. 2005; 336:779-83; Lauterbach B, Barbosa-Sicard E, Wang M H, Honeck H, Kargel E, Theuer J, Schwartzman M L, Haller H, Luft F C, Gollasch M, Schunck W H. Cytochrome P450-dependent eicosapentaenoic acid metabolites are novel BK channel activators. *Hypertension.* 2002; 39:609-13; Barbosa-Sicard E, Markovic M, Honeck H, Christ B, Muller D N, Schunck W H. Eicosapentaenoic acid metabolism by cytochrome P450 enzymes of the CYP2C subfamily. *Biochem Biophys Res Commun.* 2005; 329:1275-81). A remarkable feature of CYP-dependent n-3 PUFA metabolism is the preferred epoxidation of the n-3 double bond which distinguishes EPA and DHA from AA. The resulting metabolites—17,18-EETeTr from EPA and 19,20-EDP from DHA—are unique in having no homolog within the series of AA products.

EETs and 20-HETE play important roles in the regulation of various cardiovascular functions (Roman R J. P-450 metabolites of arachidonic acid in the control of cardiovascular function. *Physiol Rev.* 2002; 82:131-85). It has been shown that Ang II-induced hypertension is associated with a down-regulation of CYP-dependent AA metabolism (Kaergel E, Muller D N, Honeck H, Theuer J, Shagdarsuren E, Mullally A, Luft F C, Schunck W H. P450-dependent arachidonic acid metabolism and angiotensin II-induced renal damage. *Hypertension.* 2002; 40:273-9) in a double-transgenic rat (dTGR) model of Ang II-induced hypertension and end-organ damage (Luft F C, Mervaala E, Muller D N, Gross V, Schmidt F, Park J K, Schmitz C, Lippoldt A, Breu V, Dechend R, Dragun D, Schneider W, Ganten D, Haller H. Hypertension-induced end-organ damage: A new transgenic approach to an old problem. *Hypertension.* 1999; 33:212-8). The transgenic rats harbor the human renin and angiotensinogen genes, produce Ang II locally and develop significant hypertension, myocardial infarction and albuminuria. The animals die of myocardial and renal failure before the eighth week of age. The model shows severe features of Ang II-induced inflammation. Reactive oxygen species are generated, the transcription factors NF-κB and AP-1 are activated, and genes harboring binding sites for these transcription factors are activated.

Recently, it has been shown that eicosapentaenoic acid (EPA) supplementation significantly reduced the mortality of dTGR (Theuer J, Shagdarsuren E, Muller D N, Kaergel E, Honeck H, Park J K, Fiebeler A, Dechend R, Haller H, Luft F C, Schunck W H. Inducible NOS inhibition, eicosapentaenoic acid supplementation, and angiotensin II-induced renal damage. *Kidney Int.* 2005; 67:248-58). Additionally, it has been shown that dTGR develop ventricular arrhythmias based on Ang II-induced electrical remodeling (Fischer R, Dechend R, Gapelyuk A, Shagdarsuren E, Gruner K, Gruner A, Gratze P, Qadri F, Wellner M, Fiebeler A, Dietz R, Luft F C, Muller D N, Schirdewan A. Angiotensin II-induced sudden arrhythmic death and electrical remodeling. *Am J Physiol Heart Circ Physiol.* 2007; 293:H1242-1253). Treatment of the dTGR rats with a PPAR-alpha activator strongly induced CYP2C23-dependent EET production and protected against hypertension and end-organ damage (Muller D N, Theuer J, Shagdarsuren E, Kaergel E, Honeck H, Park J K, Markovic M, Barbosa-Sicard E, Dechend R, Wellner M, Kirsch T, Fiebeler A, Rothe M, Haller H, Luft F C, Schunck W H. A peroxisome proliferator-activated receptor-alpha activator induces renal CYP2C23 activity and protects from angiotensin II-induced renal injury. *Am J Pathol.* 2004; 164:521-32). Long-term feeding of dTGR (from week 4 to 7 of age) with a mixture of pure EPA- and DHA-ethyl esters (Omacor from Solvay Arzneimittel, Hannover, Germany) improved the electrical remodeling of the heart in this model of angiotensin II-induced hypertension. In particular, EPA and DHA reduced the mortality, suppressed the inducibility of cardiac arrhythmias and protected against connexin 43-gap junctional remodeling (Fischer R, Dechend R, Qadri F, Markovic M, Feldt S, Herse F, Park J K, Gapelyuk A, Schwarz I, Zacharzowsky U B, Plehm R, Safak E, Heuser A, Schirdewan A, Luft F C, Schunck W H, Muller D N. Dietary n-3 polyunsaturated fatty acids and direct renin inhibition improve electrical remodeling in a model of high human renin hypertension. Hypertension. 2008 February; 51(2): 540-6). EPA was also shown to reduce the spontaneous beating rate, to prevent $Ca^{2+}$ induced arrhythmias and to electrically stabilize neonatal rat cardiomyocytes (Leaf A, Kang J X, Xiao Y F, Hillman G E. Clinical prevention of sudden cardiac death by n-3 polyunsaturated fatty acids and mechanism of prevention of arrhythmias by n-3 fish oils. *Circulation.* 2003; 107:2646-52). In general, CYP-dependent eicosanoids have to be considered as second messengers: EETs and 20-HETE are produced by CYP enzymes after extracellular signal induced release of AA from membrane phospholipids (by phospholipase A2) and exert their function in the context of signaling pathways modulating ion transport, cell proliferation and inflammation. Depending on the diet, n-3 PUFAs partially replace AA at the sn2-position of phospholipids and may thus become involved as alternative molecules in the subsequent signaling pathways.

The few studies on the biological activities of CYP-dependent eicosanoids in the heart indicate important roles for EETs and 20-HETE in the regulation of L-type $Ca^{2+}$ and sarcolemmal and mitochondrial ATP-sensitive potassium ($K_{ATP}$) channels. In cardiac myocytes, L-type $Ca^{2+}$ currents and cell shorting are reduced upon inhibition of EET generation and these effects can be reversed by adding 11,12-EET (Xiao Y F, Huang L, Morgan J P. Cytochrome P450: a novel system modulating Ca2+ channels and contraction in mammalian heart cells. *J Physiol.* 1998; 508 (Pt 3):777-92). EETs were also shown to activate cardiac $K_{ATP}$ channels. This effect is highly stereoselective: only the S,R but not the R,S-enantiomer of 11,12-EET was effective (Lu T, VanRollins M, Lee H C. Stereospecific activation of cardiac ATP-sensitive K(+) channels by epoxyeicosatrienoic acids: a structural determinant study. *Mol Pharmacol.* 2002; 62:1076-83). Overexpression of the EET-generating human CYP2J2 resulted in an improved postischemic functional recovery of the transgenic mouse heart via activation of $K_{ATP}$ channels (Seubert J, Yang B, Bradbury J A, Graves J, Degraff L M, Gabel S, Gooch R, Foley J, Newman J, Mao L, Rockman H A, Hammock B D, Murphy E, Zeldin D C. Enhanced postischemic functional recovery in CYP2J2 transgenic hearts involves mitochondrial ATP-sensitive K+ channels and p42/p44 MAPK pathway. *Circ Res.* 2004; 95:506-14). 20-HETE appears to play an opposite role by acting as an endogenous $K_{ATP}$ channel blocker (Gross E R, Nithipatikom K, Hsu A K, Peart J N, Falck J R, Campbell W B, Gross G J. Cytochrome P450 omega-hydroxylase inhibition reduces infarct size during reperfusion via the sarcolemmal KATP channel. *J Mol Cell Cardiol.* 2004; 37:1245-9; Nithipatikom K, Gross E R, Endsley M P, Moore J M, Isbell M A, Falck J R, Campbell W B, Gross G J. Inhibition of cytochrome P450 omega-hydroxylase: a novel endogenous cardioprotective pathway. *Circ Res.* 2004; 95:e65-71).

Although n-3 PUFAs play important roles in the biological process of the mammalian body, they are not widely used as therapeutics due to their limited availability in vivo. They are readily degradable by β-oxidation, which is the major oxidative pathway in fatty acid metabolism. The net process of β-oxidation is characterised by the degradation of the fatty acid carbon chain by two carbon atoms with the concomitant production of equimolar amounts of acetyl-coenzyme A.

To overcome the problem of β-oxidation, WO96/11908 discloses modified PUFAs, such as the β-oxa and β-thia PUFAs). These compounds were shown to have enhanced resistance to β-oxidation while still retaining certain biological activities of the native PUFAs.

Finally, new agents for the treatment or prevention of conditions and diseases associated with inflammation, proliferation, hypertension, coagulation, immune function, heart failure and cardiac arrhythmias are of considerable interest as these conditions account for a significant number of death in patients and administration of many of the presently employed drugs is associated with complex drug interactions and many adverse side effects.

Therefore, the problem underlying the present invention is to provide new analogues of n-3 PUFA metabolites, which are more stable against deactivation by soluble epoxide hydrolase and/or are less prone to auto-oxidation, and which have anti-inflammatory, anti-proliferative, anti-hypertension, anti-coagulation, or immune-modulating activity, especially cardioprotective activity.

SUMMARY OF THE INVENTION

The present invention relates to a compound of the general formula (I):

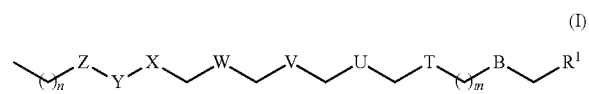

or a pharmacologically acceptable salt, solvate, hydrate or a pharmacologically acceptable formulation thereof, wherein $R^1$ is selected from

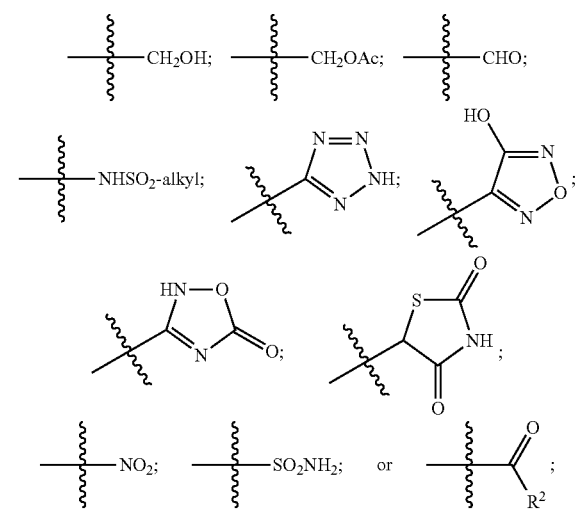

$R^2$ is hydroxy, heteroalkyl, alkoxy, polyalkoxyalkyl, $NR^3R^4$, $(NHS(O)_2-m-(C_6H_4)N_3$, or $Xaa_o$;

$R^3$ and $R^4$ are each and independently of each other selected from hydrogen atom, hydroxy, alkyl, heteroalkyl, cycloalkyl, alkylcycloalkyl, heteroalkylcycloalkyl, aralkyl, or heteroaralkyl;

Xaa is Gly, a conventional D,L-, D- or L-amino acid, a non-conventional D,L-, D- or L-amino acid, or a 2- to 10-mer peptide, wherein Xaa is joined to —C(O) by an amide bond;

o is an integer selected from 1 to 10;

B is $CH_2$, O, or S;

m is an integer from 1 to 6;

T, U, V, and W are each and independently of each other selected from —$CH_2CH_2$—, and cis or trans —CH=CH—, with the proviso that at least one of T, U, V or W is —$CH_2CH_2$—;

X is absent or selected from CH, $CH_2$, and $NR^5$, with the proviso that X is only CH if it forms together with Y and Z an epoxy group;

Z is selected from CH, $CH_2$, and $NR^{5'}$, with the proviso that Z is only CH if it forms together with X and Y an epoxy group;

$R^5$ and $R^{5'}$ are each and independently of each other selected from a hydrogen atom, a hydroxy, alkyl, cycloalkyl, alkylcycloalkyl, heteroalkylcycloalkyl, aralkyl, or heteroaralkyl group;

Y is —C(O)—, —C(O)—C(O)—, —O—, or —S—; and n is an integer from 0 to 6.

Compounds are generally described herein using standard nomenclature. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis, e.g. using modified CYP102 (CYP BM-3) or by resolution of the racemates, e.g. enzymatic resolution or resolution by conventional methods such as crystallization in the presence of a resolving agent, or chromatography, using, for example, a chiral HPLC column.

Certain compounds are described herein using a general formula that includes variables such as, e.g. B, $R^1$-$R^5$, T, U, V, W, X, Y, and Z. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups and R* at each occurrence is selected independently from the definition of R*. Also, combinations of substituents and/or variables are permissible only if such combinations result in stable compounds, i.e., compounds that can be isolated, characterized and tested for biological activity.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 6, i.e. 0, 1, 2, 3, 4, 5 or 6, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest. For example, a "ring substituent" may be a moiety such as a halogen, alkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

As used herein, the term "amino acid" refers to any organic acid containing one or more amino substituents, e.g. α-, β- or γ-amino, derivatives of aliphatic carboxylic acids. In the polypeptide notation used herein, e.g. $Xaa_5$, i.e. $Xaa_1Xaa_2Xaa_3Xaa_4Xaa_5$, wherein $Xaa_1$ to $Xaa_5$ are each and independently selected from amino acids as defined, the lefthand direction is the amino terminal direction and the righthand direction is the carboxy terminal direction, in accordance with standard usage and convention. The term "conventional amino acid" refers to the twenty naturally occurring amino acids, which are selected from the group consisting of Glycine, Leucine, Isoleucine, Valine, Alanine, Phenylalanine, Tyrosine, Tryptophan, Aspartic acid, Asparagine, Glutamic acid, Glutamine, Cysteine, Methionine, Arginine, Lysine, Proline, Serine, Threonine and Histidine, and encompasses all stereometric isoforms, i.e. D,L-, D- and L-amino acids thereof. These conventional amino acids can herein also be referred to by their conventional three-letter or one-letter abbreviations and their abbreviations follow conventional usage (see, for example, *Immunology-A Synthesis*, $2^{nd}$ Edition, E. S. Golub and D. R. Gren, Eds., Sinauer Associates, Sunderland Mass. (1991)).

The term "non-conventional amino acid" refers to unnatural amino acids or chemical amino acid analogues, e.g. α,α-disubstituted amino acids, N-alkyl amino acids, homo-amino acids, dehydroamino acids, aromatic amino acids (other than phenylalanine, tyrosine and tryptophan), and ortho-, meta- or para-aminobenzoic acid. Non-conventional amino acids also include compounds which have an amine and carboxyl functional group separated in a 1,3 or larger substitution pattern, such as β-alanine, γ-amino butyric acid, Freidinger lactam, the bicyclic dipeptide (BTD), amino-methyl benzoic acid and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art may also be used.

The use of analogues or non-conventional amino acids may improve the stability and biological half-life of the added peptide since they are more resistant to breakdown under physiological conditions. The person skilled in the art will be aware of similar types of substitution which may be made. A non limiting list of non-conventional amino acids which may be used as suitable building blocks for a peptide and their standard abbreviations (in brackets) is as follows: α-aminobutyric acid (Abu), L-N-methylalanine (Nmala), α-amino-α-methylbutyrate (Mgabu), L-N-methylarginine (Nmarg), aminocyclopropane (Cpro), L-N-methylasparagine (Nmasn), carboxylate L-N-methylaspartic acid (Nmasp), aniinoisobutyric acid (Aib), L-N-methylcysteine (Nmcys), aminonorbornyl (Norb), L-N-methylglutamine (Nmgln), carboxylate L-N-methylglutamic acid (Nmglu), cyclohexylalanine (Chexa), L-N-methylhistidine (Nmhis), cyclopentylalanine (Cpen), L-N-methylisolleucine (Nmile), L-N-methylleucine (Nmleu), L-N-methyllysine (Nmlys), L-N-methylmethionine (Nmmet), L-N-methylnorleucine (Nmnle), L-N-methylnorvaline (Nmnva), L-N-methylornithine (Nmorn), L-N-methylphenylalanine (Nmphe), L-N-methylproline (Nmpro), L-N-methylserine (Nmser), L-N- methylthreonine (Nmthr), L-N-methyltryptophan (Nmtrp), D-ornithine (Dorn), L-N-methyltyrosine (Nmtyr), L-N-methylvaline (Nmval), L-N-methylethylglycine (Nmetg), L-N-methyl-t-butylglycine (Nmtbug), L-norleucine (Nle), L-norvaline (Nva), α-methyl-aminoisobutyrate (Maib), α-methyl-γ-aminobutyrate (Mgabu), D-α-methylalanine (Dmala), α-methylcyclohexylalanine (Mthexa), D-α-methylarginine (Dmarg), α-methylcylcopentylalanine (Mcpen), D-α-methylasparagine (Dmasn), α-methyl-α-napthylalanine (Manap), D-α-methylaspartate (Dmasp), α-methylpenicillamine (Mpen), D-α-methylcysteine (Dmcys), N-(4-aminobutyl)glycine (NgIu), D-α-methylglutamine (Dmgln), N-(2-aminoethyl)glycine (Naeg), D-α-methylhistidine (Dmhis), N-(3-aminopropyl)glycine (Norn), D-α-methylisoleucine (Dmile), N-amino-α-methylbutyrate (Nmaabu), D-α-methylleucine (Dmleu), α-napthylalanine (Anap), D-α-methyllysine (Dmlys), N-benzylglycine (Nphe), D-α-methylmethionine (Dmmet), N-(2-carbamylethyl)glycine (NgIn), D-α-methylornithine (Dmorn), N-(carbamylmethyl)glycine (Nasn), D-α-methylphenylalanine (Dmphe), N-(2-carboxyethyl)glycine (NgIu), D-α-methylproline (Dmpro), N-(carboxymethyl)glycine (Nasp), D-α-methylserine (Dmser), N-cyclobutylglycine (Ncbut), D-α-methylthreonine (Dmthr), N-cycloheptylglycine (Nchep), D-α-methyltryptophan (Dmtrp), N-cyclohexylglycine (Nchex), D-α-methyltyrosine (Dmty), N-cyclodecylglycine (Ncdec), D-α-methylvaline (Dmval), N-cylcododecylglycine (Ncdod), D-N-methylalanine (Dnmala), N-cyclooctylglycine (Ncoct), D-N-methylarginine (Dnmarg), N-cyclopropylglycine (Ncpro), D-N-methylasparagine (Dnmasn), N-cycloundecylglycine (Ncund), D-N-methylaspartate (Dnmasp), N-(2,2-diphenylethyl)glycine (Nbhm), D-N-methylcysteine (Dnmcys), N-(3,3-diphenylpropyl)glycine (Nbhe), D-N-methylglutamine (Dnmgln), N-(3-guanidinopropyl)glycine (Narg), D-N-methylglutamate (Dnmglu), N-(1-hydroxyethyl)glycine (Ntbx), D-N-methylhistidine (Dnmhis), N-(hydroxyethyl))glycine (Nser), D-N-methylisoleucine (Dnmile), N-(imidazolylethyl))glycine (Nhis), D-N-methylleucine (Dnmleu), N-(3-indolylyethyl)glycine (Nhtrp), D-N-methyllysine (Dnnilys), N-methyl-γ-aminobutyrate (Nmgabu), N-methylcyclohexylalanine (Nmchexa), D-N-methylmethionine (Dnmmet), D-N-methylornithine (Dnmorn), N-methylcyclopentylalanine (Nmcpen), N-methylglycine (NaIa), D-N-methylphenylalanine (Dnmphe), N-methylaminoisobutyrate (Nmaib), D-N-methylproline (Dnmpro), N-(1-methylpropyl)glycine (Nile), D-N-methylserine (Dnmser), N-(2-methylpropyl)glycine (Nleu), D-N-methylthreonine (Dnmthr), D-N-methyltryptophan (Dnmtrp), N-(1-methylethyl)glycine (Nval), D-N-methyltyrosine (Dnmtyr), N-methyla-napthylalanine (Nmanap), D-N-methylvaline (Dnmval), N-methylpenicillamine (Nmpen), γ-aminobutyric acid (Gabu), N-(p-hydroxyphenyl)glycine (Nhtyr), L-/-butylglycine (Thug), N-(thiomethyl)glycine (Ncys), L-ethylglycine (Etg), penicillamine (Pen), L-homophenylalanine (Hphe), L-α-methylalanine (Mala), L-α-methylarginine (Marg), L-α-methylasparagine (Masn), L-α-methylaspartate (Masp), L-α-methyl-t-butylglycine (Mtbug), L-α-methylcysteine (Mcys), L-methylethylglycine (Metg), L-α-methylglutamine (MgIn), L-α-methylglutamate (MgIu), L-α-methylhistidine (Mhis), L-α-methylhomophenylalanine (Mhphe), L-α-methylisoleucine (Mile), N-(2-methylthioethyl)glycine (Nmet), L-α-methylleucine (Mleu), L-α-methyllysine (Mlys), L-α-methylmethionine (Mmet), L-α-methylnorleucine (MnIe), L-α-methylnorvaline (Mnva), L-α-methylornithine (Morn), L-α-methylphenylalanine (Mphe), L-α-methylproline (Mpro), L-α-methylserine (Mser), L-α-methylthreonine (Mthr), L-α-methyltryptophan (Mtrp), L-α-methyltyrosine (Mtyr), L-α-methylvaline (Mval), L-N-methylhomophenylalanine (Nmhphe), N—(N-(2,2-diphenylethyl)carbamylmethyl)glycine (Nnbhm), N—(N-(3,3-diphenylpropyl)carbamylmethyl)glycine (Nnbhe), 1-carboxy-1-(2,2-diphenyl-ethylamino)cyclopropane (Nmbc), L-O-methyl serine (Omser), L-O-methyl homoserine (Omhser).

The expression alkyl refers to a saturated, straight-chain or branched hydrocarbon group that contains from 1 to 20 carbon atoms, preferably from 1 to 10 carbon atoms, e.g. a n-octyl group, especially from 1 to 6, i.e. 1, 2, 3, 4, 5, or 6, carbon atoms, for example a methyl, ethyl, propyl, iso-propyl, n-butyl, iso-butyl, sec-butyl, tert-butyl, n-pentyl, iso-pentyl, n-hexyl, or 2,2-dimethylbutyl.

The expressions alkenyl and alkynyl refer to at least partially unsaturated, straight-chain or branched hydrocarbon groups that contain from 2 to 20 carbon atoms, preferably from 2 to 10 carbon atoms, especially from 2 to 6, i.e. 2, 3, 4, 5 or 6, carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atom(s) have been replaced, e.g. by a halogen atom, preferably F or Cl, such as, for example, a 2,2,2-trichloroethyl or a trifluoromethyl group.

The expression heteroalkyl refers to an alkyl, alkenyl or alkynyl group in which one or more, preferably 1, 2 or 3, carbon atoms, have been replaced independently of each other by an oxygen, nitrogen, phosphorus, boron, selenium, silicon or sulfur atom, preferably by an oxygen, sulfur or nitrogen atom. The expression heteroalkyl can also refer to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 10 carbon atoms and from 1 to 4 hetero atoms selected from oxygen, nitrogen and sulphur (especially oxygen and nitrogen). Especially preferably, a heteroalkyl group contains from 1 to 6, i.e. 1, 2, 3, 4, 5, or 6, carbon atoms and 1, 2 or 3, especially 1 or 2, hetero atoms selected from oxygen, nitrogen and sulphur, especially oxygen and nitrogen.

Examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a direct bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropyl-ethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxy-carbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, $NH_2$, =NH, $N_3$ or $NO_2$ groups, thus, for example, cyclic ketones such as, for example, cyclohexanone, 2-cyclohexenone or cyclopentanone. Further specific examples of cycloalkyl groups are a cyclo-propyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups. Examples are a piperidyl, prolinyl, imidazolidinyl, piperazinyl, morpholinyl, urotropinyl, pyrrolidinyl, tetra-hydrothiophenyl, tetrahydropyranyl, tetrahydrofuryl or 2-pyrazolinyl group and also lactames, lactones, cyclic imides and cyclic anhydrides.

The expression alkylcycloalkyl refers to a group that contains both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (especially 3, 4, 5, 6 or 7) ring carbon atoms, and one or two alkyl, alkenyl or alkynyl groups having 1 or 2 to 6 carbon atoms.

The expression heteroalkylcycloalkyl refers to alkylcycloalkyl groups as defined above in which one or more, preferably 1, 2 or 3, carbon atoms have been replaced independently of each other by an oxygen, nitrogen, silicon, selenium, phosphorus or sulfur atom (preferably by an oxygen, sulfur or nitrogen atom). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkyl-heterocycloalkyl and heteroalkylheterocycloalkenyl, the cyclic groups being saturated or mono-, di- or tri-unsaturated.

The expression aryl or Ar refers to an aromatic group that contains one or more rings containing from 6 to 14 ring carbon atoms, preferably from 6 to 10 (especially 6) ring carbon atoms. The expression aryl (or Ar, respectively) refers furthermore to groups in which one or more hydrogen atoms have been replaced by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). The expression heteroaryl refers furthermore to groups in which one or more hydrogen atoms have been replaced by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), triazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3"-bifuryl, pyrazolyl (e.g. 3-pyrazolyl) and isoquinolinyl groups.

The expression aralkyl refers to a group containing both aryl and also alkyl, alkenyl, alkynyl and/or cycloalkyl groups in accordance with the above definitions, such as, for example, an arylalkyl, arylalkenyl, arylalkynyl, arylcycloalkyl, aryl-cycloalkenyl, alkylarylcycloalkyl and alkylarylcycloalkenyl group. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (preferably 1, 2, 3 or 4) carbon atoms, each independently, have been replaced by an oxygen, nitrogen, silicon, selenium, phosphorus, boron or sulfur atom (preferably oxygen, sulfur or nitrogen), that is to say to a group containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups in which one or more hydrogen atoms of such groups have been replaced independently of each other by fluorine, chlorine, bromine or iodine atoms or by OH, =O, SH, =S, $NH_2$, =NH, $N_3$ or $NO_2$ groups.

The expression "optionally substituted" refers to a group in which one, two, three or more hydrogen atoms have been replaced independently of each other by fluorine, chlorine, bromine or iodine atoms or by OH, =O, SH, =S, $NH_2$, =NH, $N_3$ or $NO_2$ groups. This expression refers furthermore to a group that is substituted by one, two, three or more (preferably unsubstituted) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_2$-$C_{12}$ alkylcycloalkyl, $C_2$-$C_{11}$ heteroalkylcycloalkyl $C_6$-$C_{10}$ aryl, $C_1$-$C_9$ heteroaryl, $C_7$-$C_{12}$ aralkyl or $C_2$-$C_{11}$ heteroaralkyl groups.

The expression "halogen" or "halogen atom" as preferably used herein means fluorine, chlorine, bromine, or iodine.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range.

Preferably, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

Preferred is a compound of formula (I), wherein X and Z are each and independently of each other selected from CH, $CH_2$, and $NR^5$, with the proviso that X and Z are only CH if they form together with Y an epoxy group.

Preferred is a compound of formula (I), wherein $R^1$ is —$COR^2$.

Further preferred is a compound of formula (I), wherein $R^2$ is hydroxy, —$O(CH_2CH_2O)_pH$, or $NR^3R^4$, wherein p is an integer from 1 to 25, especially an integer from 1 to 3.

Further preferred is a compound of formula (I), wherein m is 1.

Further preferred is a compound of formula (I), wherein n is 0 or 1.

Also preferred is a compound of formula (I), wherein X, Y and Z together form an epoxy group, especially an epoxy group where X represents a CH-group with R-configuration and Z represents a CH-group with S-configuration.

Moreover preferred is a compound of formula (I), wherein V is —CH=CH—.

Furthermore preferred is a compound of formula (I), wherein W is —CH=CH—.

Further preferred is a compound of formula (I), wherein each of T, U and W is —$CH_2CH_2$—.

Especially preferred is a compound of formula (I), wherein Y is —C(O)— or —C(O)—C(O)—.

Further, especially preferred, is a compound of formula (I), wherein X is $NR^5$ with $R^5$ being a hydrogen atom, a methyl, ethyl, propyl or iso-propyl group.

Further, especially preferred, is a compound of formula (I), wherein Z is $NR^{5'}$ with $R^{5'}$ being a hydrogen atom, a methyl, ethyl, propyl or iso-propyl group.

Especially preferably, the compounds of formula (I) are selected from the following compounds:

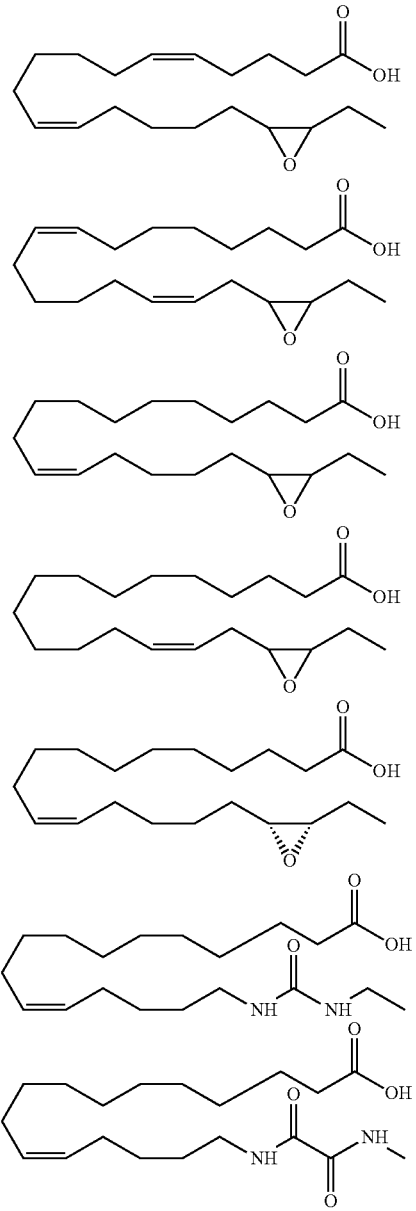

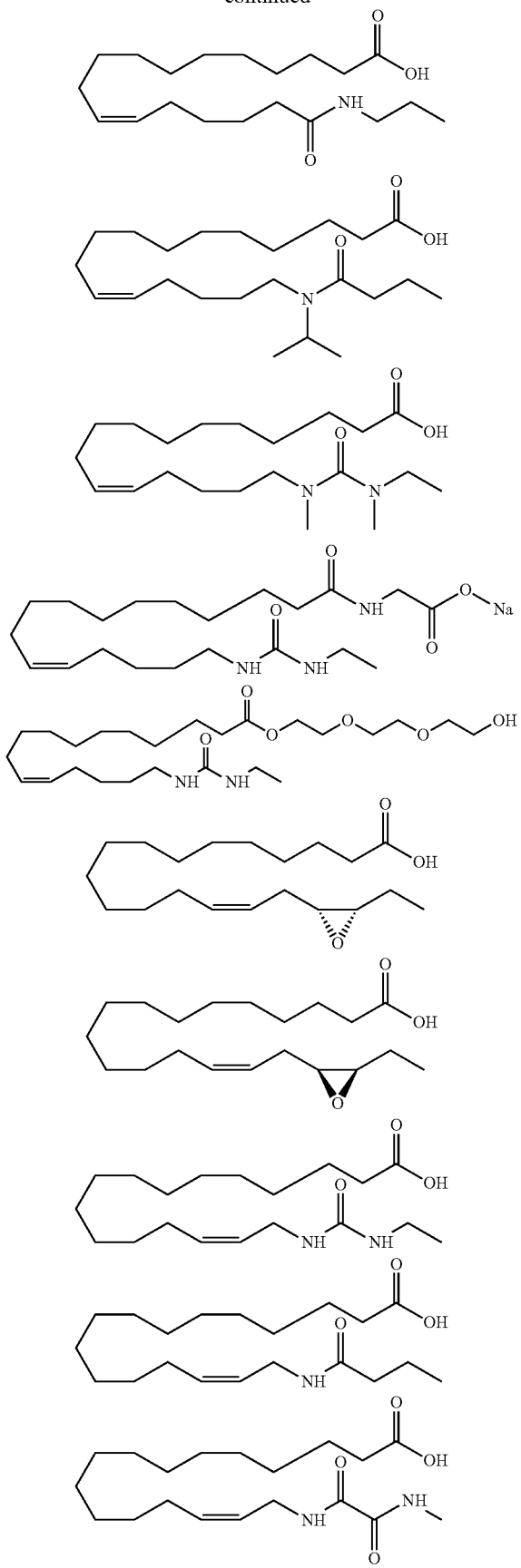

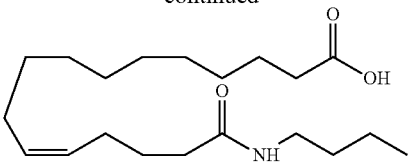

It is especially preferred to combine the preferred embodiments of the individual generic groups of formula (I) in any possible manner.

The compounds of formula (I) according to the present invention have improved properties, especially, low toxicity, low drug drug interaction, improved bioavailability especially with regard to oral administration, improved metabolic stability, and improved solubility.

The compounds provided herein exhibit high cardioprotective activity in a double transgenic rat model of Ang II-induced hypertension and end-organ damage.

The therapeutic use of compounds of formula (I), their pharmacologically acceptable salts, solvates or hydrates and also formulations and pharmaceutical compositions lie within the scope of the present invention. The present invention also relates to the use of those compounds of formula (I) as active ingredients in the preparation of medicaments and also to their use for the treatment of cardiac damage.

The pharmaceutical compositions according to the present invention comprise at least one compound of formula (I) and, optionally, one or more carrier substances, e.g. cyclodextrins such as hydroxypropyl β-cyclodextrin, micelles or liposomes, excipients and/or adjuvants. Pharmaceutical compositions may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical compositions provided herein. For instance, the compounds of the invention may advantageously be employed in combination with an antibiotic, anti-fungal, or anti-viral agent, an anti-histamine, a non-steroidal anti-inflammatory drug, a disease modifying anti-rheumatic drug, a cytostatic drug, a drug with smooth muscle activity modulatory activity or mixtures of the aforementioned.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions such as, e.g., in the treatment of skin conditions such as burns or itch.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent such as, e.g., calcium carbonate, calcium phosphate or kaolin, or as soft gelatin capsules wherein the active ingredient is mixed with water or an oil medium such as, e.g., peanut oil, liquid paraffin or olive oil.

Aqueous suspensions contain the active ingredient(s) in admixture with excipients suitable for the manufacture of aqueous suspensions. Such excipients include suspending agents such as, e.g., sodium carboxymethylcellulose, methylcellulose, hydropropylmethylcellulose, sodium alginate, polyvinylpyrrolidone, gum tragacanth and gum acacia; and dispersing or wetting agents such as, e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil such as, e.g., *arachis* oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil such as, e.g., olive oil or *arachis* oil, a mineral oil such as, e.g., liquid paraffin, or a mixture thereof. Suitable emulsifying agents include naturally-occurring gums such as, e.g., gum acacia or gum tragacanth, naturally-occurring phosphatides such as, e.g., soy bean lecithin, and esters or partial esters derived from fatty acids and hexitol, anhydrides such as, e.g., sorbitan monoleate, and condensation products of partial esters derived from fatty acids and hexitol with ethylene oxide such as, e.g., polyoxyethylene sorbitan monoleate. An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Compounds may be formulated for local or topical administration, such as for topical application to the skin or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols such as, e.g., ethanol or isopropyl alcohol or glycerin; glycols such as, e.g., butylene, isoprene or propylene glycol; aliphatic alcohols such as, e.g., lanolin; mixtures of water and organic solvents and mixtures of organic solvents such as alcohol and glycerin; lipid-based materials such as fatty acids, acylglycerols including oils, such as, e.g., mineral oil, and fats of natural or synthetic origin, phosphoglycerides, sphingolipids and waxes; protein-based materials such as collagen and gelatin; silicone-based materials, both non-volatile and volatile; and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (*Pharmaceutical Press*, London 1993) and Martin (ed.), Remington's Pharmaceutical Sciences. Formulations may comprise microcapsules, such as hydroxymethylcellulose or gelatin-microcapsules, liposomes, albumin microspheres, micro-emulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included in a topical formulation include, but are not limited to, abrasives, absorbents, anti-caking agents, anti-foaming agents, anti-static agents, astringents such as, e.g., witch hazel, alcohol and herbal extracts such as chamomile extract, binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%); Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying including mist, aerosol or foam spraying; dropper application; sprinkling; soaking; and rinsing. Controlled release vehicles can also be used, and compositions may be formulated for transdermal administration as a transdermal patch.

A pharmaceutical composition may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Pharmaceutical compositions may also be prepared in the form of suppositories such as e.g., for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as, i.e., a formulation such as a capsule that creates a slow release of modulator following administration. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

For the treatment of cardiac damage, especially cardiac arrhythmias, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day, about 0.5 mg to about 7 g per patient per day. The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination, i.e. other drugs being used to treat the patient, and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

n-3 PUFA derivatives provided herein are preferably administered to a patient such as, e.g., a human, orally or parenterally, and are present within at least one body fluid or tissue of the patient. Accordingly, the present invention further provides methods for treating patients suffering from cardiac damage. As used herein, the term "treatment" encompasses both disease-modifying treatment and symptomatic treatment, either of which may be prophylactic, i.e., before the onset of symptoms, in order to prevent, delay or reduce the severity of symptoms, or therapeutic, i.e., after the onset of symptoms, in order to reduce the severity and/or duration of symptoms. Patients may include but are not limited to primates, especially humans, domesticated companion animals such as dogs, cats, horses, and livestock such as cattle, pigs, sheep, with dosages as described herein.

Compounds of formula (I) of the present invention may be used for the treatment and/or prevention of conditions and diseases associated with inflammation, proliferation, hypertension, coagulation, immune function, heart failure and cardiac arrhythmias.

Examples of conditions and diseases associated with proliferation include tumors or neoplasms, where proliferation of cells is uncontrolled and progressive. Some such uncontrolled proliferating cells are benign, but others are termed "malignant" and may lead to death of the organism. Malignant neoplasms or "cancers" are distinguished from benign growths in that, in addition to exhibiting aggressive cellular proliferation, they may invade surrounding tissues and metastasize. Moreover, malignant neoplasms are characterized in that they show a greater loss of differentiation (greater"dedifferentiation"), and greater loss of their organization relative to one another and their surrounding tissues. This property is also called "anaplasia". Neoplasms treatable by the present invention also include solid phase tumors/malignancies, i. e., carcinomas, locally advanced tumors and human soft tissue sarcomas. Carcinomas include those malignant neoplasms derived from epithelial cells that infiltrate (invade) the surrounding tissues and give rise to metastastic cancers, including lymphatic metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems. The type of cancer or tumor cells that may be amenable to treatment according to the invention include, for example, breast, colon, lung, and prostate cancers, gastrointestinal cancers including esophageal cancer, stomach cancer, colorectal cancer, polyps associated with colorectal neoplasms, pancreatic cancer and gallbladder cancer, cancer of the adrenal cortex, ACTH-producing tumor, bladder cancer, brain cancer including intrinsic brain tumors, neuroblastomas, astrocytic brain tumors, gliomas, and metastatic tumor cell invasion of the central nervous system, Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer; breast cancer (small cell and ductal), penile cancer, retinoblastoma, testicular cancer, thyroid cancer, trophoblastic neoplasms, and Wilms' tumor.

Examples of conditions and diseases associated with inflammation and immune function include inflammatory disorders such as acute-phase reaction, local and systemic inflammation and inflammation caused by other diseases whatever type, etiology or pathogenesis and caused by inflammatory diseases exemplified below, and immunological disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, and vasculitis. In particular, examples of such conditions and diseases include inflammatory bowel disease including Crohn's disease and ulcerative colitis (Stadnicki et al., *Am. J. Physiol. Gastrointest Liver Physiol.* 2005, 289(2), G361-6; Devani et al., *Am. J. Gastroenerol* 2002, 97(8), 2026-32; Devani et al., *Dig. Liv. Disease* 2005, 37(9), 665-73), irritable bowel syndrome, enterocolitis, liver diseases, pancreatitis, nephritis, cystitis (interstitial cystitis), uveitis, retinitis, glaucoma, otitis media, peridontitis, inflammatory skin disorders such as psoriasis, eczema, atopic diseases, dermatitis, itching, juvenile or adult onset rheumatoid arthritis and gouty arthritis (Cassim et al., *Pharmacol. Ther.* 2002, 94, 1-34; Sharma et al., *Exp. Toxic Pathol.* 1994, 46, 421-433; Brechter et al., *Arthr. Rheum.* 2007, 56(3), 910-923), ankylosing spondylitis, adult onset or pediatric (systemic onset juvenile idiopathic arthritis) Still's disease, psoriatic arthritis, osteoarthritis and edema associated with burns, sprains or fracture, cerebral edema, closed head injury, angioedema, vasculitis, diabetic vasculopathy, type I diabetes, diabetic nephropathy, diabetic neuropathy, diabetic retinopathy, post capillary resistance or diabetic syndromes associated with insults (e.g. hyperglycemia, diuresis, proteinuria and increased nitrite and kallikrein urinary excretion), gall bladder diseases, smooth muscle relaxants for the treatment of spasms of the gastrointestinal tract or uterus, multiple sclerosis, epilepsy, amyotrophic lateral sclerosis, Alzheimer's disease, stroke, Parkinson's disease, systemic inflammatory response syndrome (SIRS), ischemia-reperfusion injury and atherosclerosis (Raidoo et al., *Immunopharmacol* 1997, 36(2-3), 153-60; McLean et al., *Cardiovasc. Res.* 2000, 48, 194-210), septic shock, antihypovolemic and/or anti-hypotensive agents, headache including cluster headache, migraine including prophylactic and acute use, closed head trauma, cancer, sepsis, gingivitis, osteoporosis, benign prostatic hyperplasia, hyperactive bladder, fibrotic diseases such as pulmonary fibrosis, renal fibrosis, liver fibrosis, progressive sclerosis and recurrent stricture formation in Crohn's disease (Goldstein et al., *J. Biol. Chem.* 1984, 259(14), 9263-8; Ricupero et al., *J. Biol. Chem.* 2000, 275(17), 12475-80; Romero et al., *J. Biol. Chem.* 2005, 15, 14378-14384), disorders of the respiratory pathways in asthma, atopic or non-atopic asthma, occupational asthma, exercise-induced bronchoconstriction, bronchitis, pneumoconiosis including aluminosis, anhracosis, asbestosis, chalicosis, ptilosis, siderosis, silicosis, tabaccosis and byssinosis, chronic obstructive pulmonary disease including emphysema, adult respiratory distress syndrome, pneumonia, allergic rhinitis, vasomotor rhinitis and pleurisy, auto-inflammatory diseases such as familial Mediterranean fever (FMF), tumor-necrosis factor receptor associated periodic syndrome (TRAPS), neonatal onset multisystem inflammatory disease (NOMID), familial cold autoinflammatory syndrome (FCAS) including familial cold urticaria (FCU), pyogenic arthritis pyoderma gangrenosum acne (PAPA) syndrome and Muckle-Wells disease Examples of conditions and diseases associated with heart failure and cardiac arrhythmias include diseases associated with cardiac damage including sudden cardiac death after myocardial infarction, cardiac arrhythmias including ventricular tachycardia, malignant ventricular tachycardia and atrial fibrillation, heart failure based on coronary artery disease, dilatative cardiomyopathy, myocarditis, hypertensive heart disease, diabetes and inflammatory cardiomyopathy.

It is also within the present invention that the compounds according to the invention are used as or for the manufacture of a diagnostic agent, whereby such diagnostic agent is for the diagnosis of the diseases and conditions which can be addressed by the compounds of the present invention for therapeutic purposes as disclosed herein.

For various applications, the compounds of the invention can be labelled by isotopes, fluorescence or luminescence markers, antibodies or antibody fragments, any other affinity label like nanobodies, aptamers, peptides etc., enzymes or enzyme substrates. These labelled compounds of this invention are useful for mapping the location of BK receptors in vivo, ex vivo, in vitro and in situ such as, e.g. in tissue sections via autoradiography and as radiotracers for positron emission tomography (PET) imaging, single photon emission computerized tomography (SPECT) and the like to characterize those receptors in living subjects or other materials. The labelled compounds according to the present invention may be used in therapy, diagnosis and other applications such as research tools in vivo and in vitro, in particular the applications disclosed herein.

DESCRIPTION OF VARIOUS EMBODIMENTS OF THE INVENTION

Figure 1:
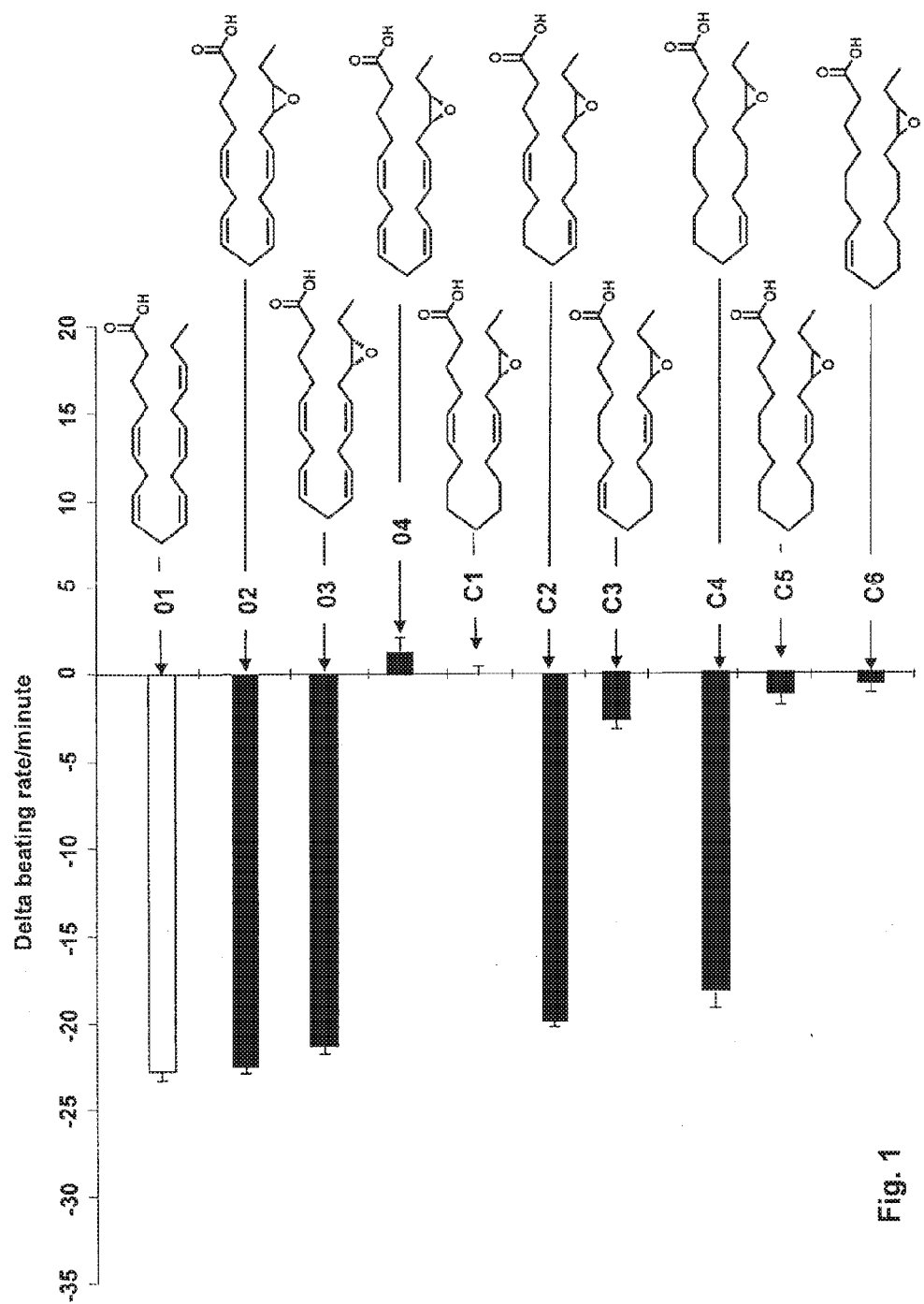
FIG. 1 shows the structures of compounds tested and the values for the chronotropic effects (Δ beats/min) based on the difference between the basal and compound-induced beating rate of the individual clusters.
Figure 1:
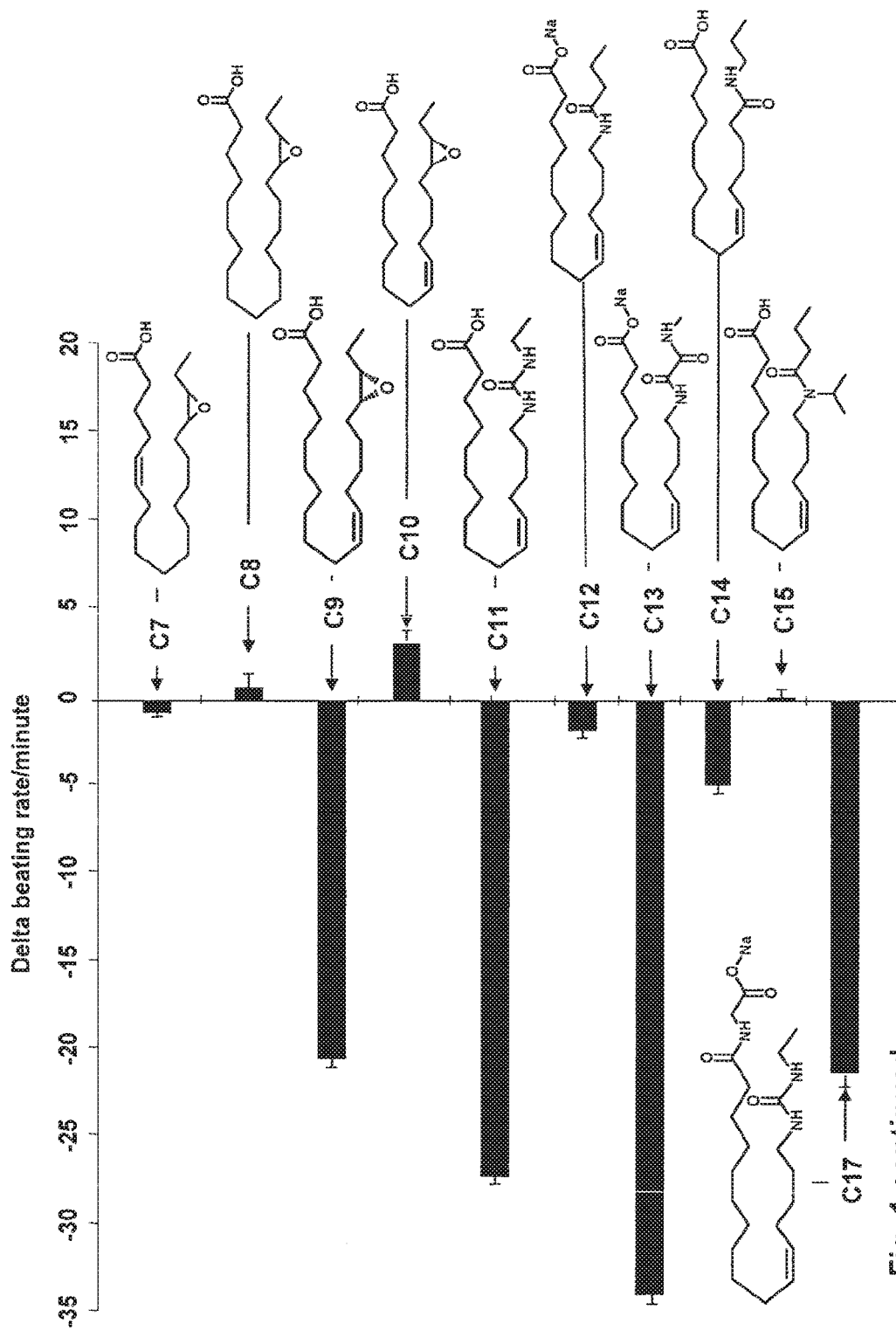
Figure 1:
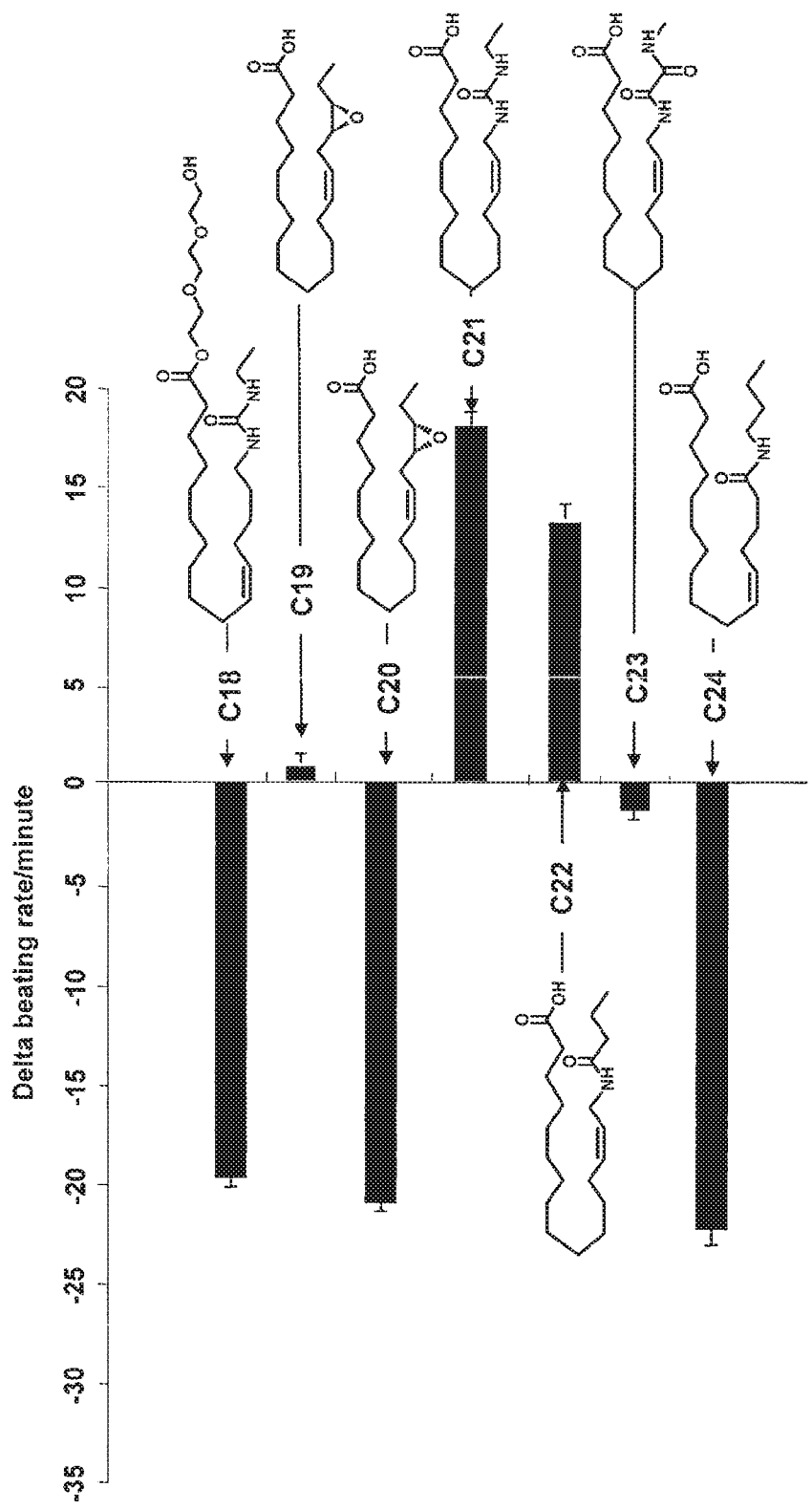

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

Example 1

Synthesis of (5Z,14Z)-16-(3-Ethyloxirane-2-yl) hexadeca-5,14-dienoic acid (1)

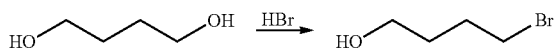

1,4-Butanediol (32 g, 35.55 mmol; Alfa Aesar) and aq. 48% HBr (45 mL) were heated under reflux in benzene (380 mL) with water removal using a Dean-Stark apparatus. After 12 h, all volatiles were removed in vacuo and the residue was purified by $SiO_2$ column chromatography using a gradient of 10-30% EtOAc/hexanes as eluent to give 4-bromobutan-1-ol (29.20 g, 68%). TLC: 30% EtOAc/hexanes, $R_f$=0.30; $^1$H NMR ($CDCl_3$, 300 MHz) δ 3.70 (t, J=6.1 Hz, 2H), 3.45 (t, J=6.1 Hz, 2H), 1.92-2.04 (m, 2H), 1.68-1.78 (m, 2H).

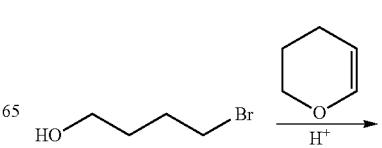

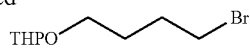

3,4-Dihydro-2H-pyran (8.0 g, 95.36 mmol) was added to a 0° C. solution of 4-bromobutan-1-ol (12.0 g, 79.47 mmol) in dichloromethane (150 mL) followed by p-toulenesulphonic acid (20 mg). After 1 h, the reaction was carefully quenched with sat. aq. NaHCO$_3$ solution (5 mL), washed with water (100 mL), brine (70 mL), and concentrated in vacuo. The residue was purified by SiO$_2$ column chromatography using 2% EtOAc/hexanes as eluent to give 2-(4-bromobutoxy)tetrahydro-2H-pyran (16.57 g, 88%) as colorless oil. TLC: 10% EtOAc/hexanes, R$_f$≈0.50; $^1$H NMR (CDCl$_3$, 300 MHz) δ 4.58 (t, J=2.5 Hz, 1H), 3.90-3.72 (m, 2H), 3.38-3.50 (m, 4H), 1.92-2.04 (m, 2H), 1.65-1.80 (m, 4H), 1.60-1.50 (m, 4H). Lit. ref: G. L. Kad; I. Kaur; M. Bhandari; J. Singh; J. Kaur *Organic Process Research & Development* 2003: 7, 339.

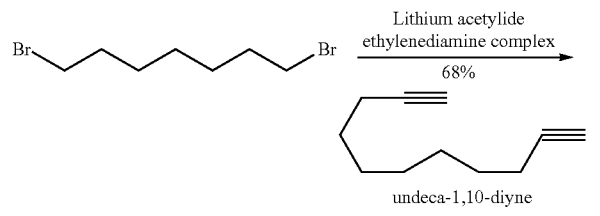

A solution of 1,7-dibromoheptane (13.5 g, 52.32 mmol) in anhydrous dimethylsulfoxide (25 mL) was added dropwise to a stirring, 0° C. solution of lithium acetylide ethylenediamine complex (12.04 g, 130.8 mmol) in anhydrous dimethylsulfoxide (125 mL) under an argon atmosphere. After stirring at 5-8° C. for 2 h, the reaction mixture was diluted with ether (100 mL) and washed with water (2×40 mL). The aqueous washes were extracted with ether (2×50 mL). The combined ethereal fractions were dried over anhydrous Na$_2$SO$_4$ and concentrated under reduced pressure. The residue was purified by SiO$_2$ column chromatography using hexanes as eluent to give undec-1,10-diyne as a colorless oil (5.3 g, 68%) (lit. ref: Hellbach, Björn; Gleiter, Rolf; Rominger, Frank Synthesis 2003, 2535-2541). TLC: SiO$_2$, hexane (100%), R$_f$≈0.8; $^1$H NMR (300 MHz, CDCl$_3$) δ 2.14-2.18 (m, 4H), 1.92 (t, J=2.55 Hz, 2H), 1.50-1.53 (m, 4H), 1.40-1.42 (m, 4H), 1.23-1.25 (m, 2H).

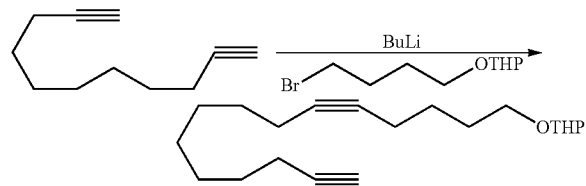

n-BuLi (4.86 mL of 2.5 M in hexanes, 12.16 mmol) was added dropwise to a −78° C. solution of undec-1,10-diyne (2.0 g, 13.51 mmol) in dry tetrahydrofuran/HMPA (105 mL, 6:1) under an argon atmosphere. After 30 min, the reaction mixture was warmed to −10° C. over 2 h and maintained at this temperature for 20 min, then re-cooled to −75° C. To this was added a solution of 2-(4-bromobutoxy)-tetrahydropyran (2.4 g, 10.14 mmol) in dry THF (15 mL). The resulting mixture was warmed to room temperature over 3 h, maintained at this temperature for 12 h, then quenched with sat. aq. NH$_4$Cl (25 mL). After 20 min, the mixture was extracted with ether (2×125 mL). The combined ethereal extracts were washed with water (2×100 mL), brine (100 mL), dried over Na$_2$SO$_4$ and concentrated under reduced pressure. The residue was purified by SiO$_2$ column chromatography using 5% EtOAc/hexanes as eluent to give 2-(pentadeca-5,14-diynyloxy)tetrahydropyran (1.97 g, 64%) as a colorless oil. TLC: 10% EtOAc/hexanes, R$_f$≈0.6; $^1$H NMR (400 MHz, CDCl$_3$) δ 4.58 (t, J=2.5 Hz, 1H), 3.82-3.89 (m, 1H), 3.71-3.78 (m, 1H), 3.43-3.53 (m, 1H), 3.36-3.47 (m, 1H), 2.01-2.20 (m, 6H), 1.93 (t, J=2.5 Hz, 1H), 1.27-1.81 (m, 20H). Lit. ref: F. Slowinski; C. Aubert; M. Malacria *Eur. J. Org. Chem.* 2001: 3491.

The reaction also produced approximately 10% of the dialkylated adduct. TLC: 10% EtOAc/hexanes, R$_f$≈0.3; $^1$H NMR (300 MHz, CDCl$_3$) δ 4.58 (t, J=2.5 Hz, 2H), 3.82-3.89 (m, 2H), 3.71-3.78 (m, 2H), 3.43-3.53 (m, 2H), 3.36-3.47 (m, 2H), 2.01-2.20 (m, 8H), 1.27-1.81 (m, 30H).

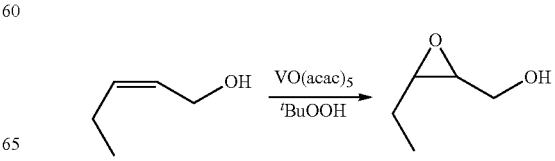

A solution of the 2-(pentadeca-5,14-diynyloxy)tetrahydropyran (4.05 g, 13.27 mmol) and p-toluenesulphonic acid (42 mg) in MeOH (100 mL) was stirred at room temperature for 4 h. All volatiles were then removed in vacuo and the residue was purified by SiO$_2$ column chromatography using 15% EtOAc/hexanes as eluent to give pentadeca-5,14-diyn-1-ol (2.77 g, 95%) as a colorless oil. TLC: 30% EtOAc/hexanes, R$_f$≈0.40; $^1$H NMR (300 MHz, CDCl$_3$) δ 3.85 (t, 2H, J=7.0 Hz), 2.03-2.30 (m, 6H), 1.93 (t, 1H, J=2.6 Hz), 1.26-1.83 (m, 14H).

Jones reagent (10 mL of a 10 N solution in water) in acetone (25 mL) was added to a stirring, −40° C. solution of above alcohol (1.9 g, 4.55 mmol) in acetone (75 mL). After 1 h, the reaction mixture was warmed to −10° C. and maintained for another 2 h, then quenched with excess (5 equiv) of isopropanol. The green chromium salts were removed by filtration and the filter cake was washed with acetone. The combined filtrates were concentrated in vacuo and the obtained residue was dissolved in EtOAc (100 mL), washed with water (50 mL) and again concentrated in vacuo. The residue was purified by SiO$_2$ column chromatography using 15% EtOAc/hexanes as eluent to give pentadeca-5,14-diynoic acid (2.42 g, 82%) as a white solid. TLC: 40% EtOAc/hexanes, R$_f$≈0.40; $^1$H NMR (400 MHz, CDCl$_3$) δ 2.48 (t, 2H, J=7.3 Hz), 2.10-2.17 (m, 6H), 1.93 (t, 1H, J=2.6 Hz), 1.75-1.86 (m, 2H), 1.25-1.55 (m, 10H).

tert-Butyl hydroperoxide (15.72 g, 33 mL of a 5.2 M solution in decane) was added to a stirring solution of pent-2(Z)-en-1-ol (5.00 g, 58.14 mmol) and vanadium(III) acetylacetonate (150 mg) in dry benzene (200 mL) under an argon atmosphere. The initial pale green solution turned pink. After 3 h, the reaction was quenched with dimethylsulfide (52 g, 87.33 mmol, 5 equiv). After an additional 1 h, the reaction was diluted with an equal volume of $Et_2O$ (250 mL), washed with water (2×250 mL), brine (200 mL), dried over $Na_2SO_4$, and concentrated in vacuo. The residue was purified by $SiO_2$ column chromatography using 30% EtOAc/hexanes as eluent to give (Z)-(3-ethyloxiranyl)-methanol (4.86 g, 82%) as a pale yellow oil. TLC: 40% EtOAc/hexanes, $R_f \approx 0.3$; $^1H$ NMR (400 MHz, $CDCl_3$) δ 3.86 (dd, 1H, J=12.1 Hz, 4.0 Hz), 3.67 (dd, 1H, J=6.8 Hz, 4.0 Hz), 3.17 (ddd, 1H, J=4.1 Hz, 4.3 Hz, 6.8 Hz), 3.01 (ddd, 1H, J=4.3 Hz, 6.4 Hz, 6.4 Hz) 1.46-1.71 (m, 2H), 1.04 (t, 3H, J=7.6 Hz). Lit. ref: C. Arnold; W. Stefan; Y. A. Yse; S. H. Dieter *Liebigs Annalen der Chemie* 1987: 7, 629.

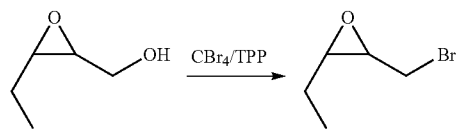

A solution of carbon tetrabromide (10.8 g, 32.64 mmol) in $CH_2Cl_2$ (25 mL) was stirred into a −10° C. solution of triphenylphosphine (8.6 g, 32.94 mmol) and the above epoxy alcohol (2.8 g, 27.45 mmol) in dry $CH_2Cl_2$ (100 mL) under an argon atmosphere. After 30 min, the reaction mixture was washed with water (75 mL), brine (50 mL), dried over anhydrous $Na_2SO_4$, and all volatiles were removed under reduced pressure. The residue was purified by $SiO_2$ column chromatography using 5% EtOAc/hexanes as eluent to give (Z)-2-bromomethyl-3-ethyloxirane (2.92 g, 65%) as colorless oil. TLC: 20% EtOAc/hexanes, $R_f \approx 0.6$; $^1H$ NMR (400 MHz, $CDCl_3$) δ 3.49-3.53 (dd, 1H, J=4.9, 9.3 Hz), 3.22-3.31 (m, 2H), 3.01-3.06 (m, 1H), 1.54-1.62 (m, 2H), 1.08 (t, 3H, J=7.6 Hz).

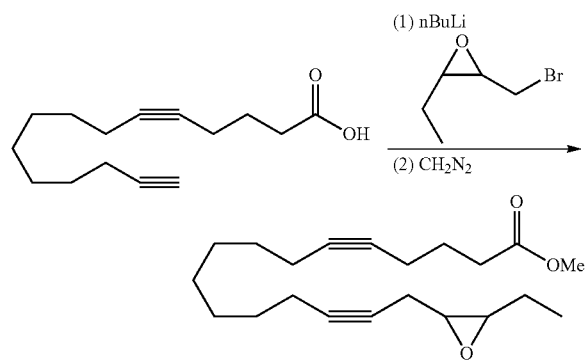

n-BuLi (1.8 mL of a 2.5 M hexanes solution, 4.48 mmol) was added slowly to a −70° C. solution of pentadeca-5,14-diynoic acid (0.5 g, 2.14 mmol) in dry tetrahydrofuran (30 mL) and HMPA (8 mL) under an argon atmosphere. The resulting mixture was stirred at −75° C. for 30 min, then allowed to warm to 0° C. over 2 h. After 1 h at 0° C., the reaction mixture was re-cooled −72° C. and a solution of (Z)-2-bromomethyl-3-ethyloxirane (0.46 g, 2.56 mmol) in dry THF (10 mL) was introduced. The resulting mixture was warmed to room temperature over 3 h. After stirring at room temperature for 12 h, the reaction was quenched with sat. aq. $NH_4Cl$ (10 mL), stirred for 20 min, and then extracted with ether (3×75 mL). The combined ethereal extracts were washed with water (2×100 mL), brine (100 mL), dried over $Na_2SO_4$ and concentrated under reduced pressure. The residue was dissolved in 5% MeOH/ether, cooled to 0° C., and treated with an excess of ethereal diazomethane until the yellow color persisted for 10 min. After 1 h, all volatiles were removed under reduced pressure and the residue was purified by $SiO_2$ column chromatography using 5% EtOAc/hexanes as eluent to give methyl 16-[(Z)-3-ethyloxiranyl]hexadeca-5,14-diynoate (0.39 g, 56%) as a colorless oil. TLC: 10% EtOAc/hexanes, $R_f \approx 0.5$; $^1H$ NMR (400 MHz, $CDCl_3$) δ 3.65 (s, 3H), 3.07-3.12 (m, 1H), 2.88-2.92 (m, 1H), 2.51-2.58 (m, 1H), 2.41 (t, 2H, J=7.3), 2.08-2.26 (m, 7H), 1.74-1.81 (m, 2H), 1.22-1.64 (m, 12H), 1.05 (t, 3H, J=7.6 Hz). Lit. ref: J. R. Falck; P. S. Kumar; Y. K. Reddy; G. Zou; J. H. Capdevila *Tetrahedron Lett.* 2001: 42, 7211.

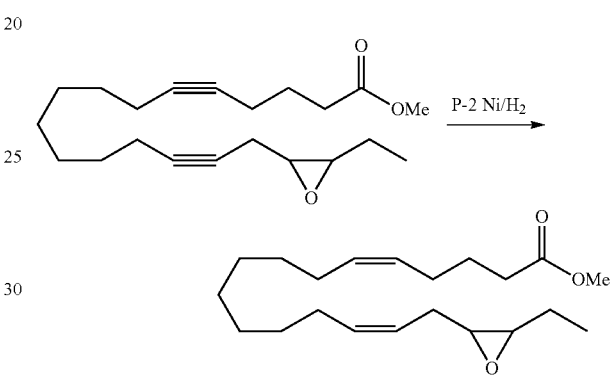

$NaBH_4$ (33 mg, 0.88 mmol) was added portionwise to a stirring solution of nickel(II) acetate tetrahydrate (190 mg, 0.76 mmol) in absolute ethanol (5 mL) under a hydrogen blanket (1 atm). After 15 min, freshly distilled ethylenediamine (200 mg, 3.24 mmol) was added followed by a solution of methyl 16-[(Z)-3-ethyloxiranyl]hexadeca-5,14-diynoate (360 mg, 1.08 mmol) in absolute ethanol (5 mL). The heterogeneous mixture was maintained at room temperature for 90 min, then diluted with ether (15 mL), and filtered through a short pad of silica gel. The filter cake was washed with ether (3×5 mL). The combined ethereal filtrates were dried over anhydrous $Na_2SO_4$ and concentrated in vacuo to give methyl 16-[(Z)-3-ethyloxiranyl]hexadeca-5(Z),14(Z)-dienoate (0.35 g, 97%) as a colorless oil sufficiently pure to be used in the next step without purification. TLC: 20% EtOAc/hexanes, $R_f \approx 0.6$; $^1H$ NMR (400 MHz, $CDCl_3$) δ 5.24-5.54 (m, 4H), 3.62 (s, 3H), 2.82-2.92 (m, 2H), 2.26-2.38 (m, 1H), 2.29 (t, 2H, J=7.3 Hz), 2.10-2.18 (m, 1H), 1.93-2.06 (m, 6H), 1.60-1.69 (m, 2H), 1.46-1.59 (m, 2H), 1.20-1.34 (m, 10H), 1.01 (t, 3H, J=7.3 Hz); $^{13}C$ NMR (100 MHz, $CDCl_3$) δ 174.24, 133.12, 130.16, 128.62, 124.12, 58.6, 56.8, 51.96, 33.72, 29.91, 29.84, 29.58, 29.46, 27.54, 27.48, 26.84, 26.43, 25.06, 21.21, 10.08.

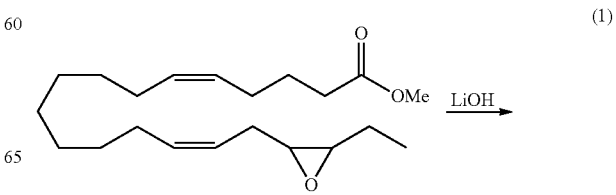

(1)

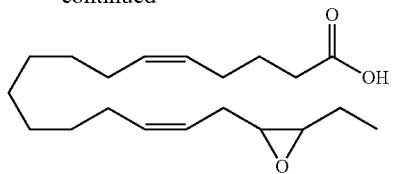

LiOH (1 mL, 2 M aqueous solution) was added to a 0° C. solution of methyl 16-[(Z)-3-ethyloxiranyl]hexadeca-5(Z),14(Z)-dienoate (90 mg, 0.266 mmol) in THF (8 mL) and deionized H$_2$O (2 mL). After stirring at room temperature overnight, the reaction mixture was cooled to 0° C., the pH was adjusted to 4 with 1 M aq. oxalic acid, and extracted with ethyl acetate (2×20 mL). The combined extracts were washed with water (30 mL), brine (25 mL), dried over anhydrous Na$_2$SO$_4$, and concentrated in vacuo. The residue was purified by SiO$_2$ column chromatography using 25% EtOAc/hexanes as eluent to give 16-[(Z)-3-ethyloxiranyl]hexadeca-5(Z),14(Z)-dienoic acid (82 mg, 92%) as a colorless oil. TLC: 30% EtOAc/hexanes, R$_f$≈0.3; $^1$H NMR (400 MHz, CDCl$_3$) δ 5.26-5.51 (m, 4H), 2.88-2.98 (m, 2H), 2.31-2.44 (m, 1H), 2.35 (t, 2H, J=7.7 Hz), 2.13-2.20 (m, 1H), 1.96-2.11 (m, 6H), 1.64-1.70 (m, 2H), 1.48-1.61 (m, 2H), 1.22-1.37 (m, 10H), 1.05 (t, 3H, J=7.51); $^{13}$C NMR (100 MHz, CDCl$_3$) δ 179.96, 133.02, 131.87, 128.40, 123.97, 58.85, 57.73, 33.86, 30.04, 29.96, 29.94, 29.88, 29.81, 27.64, 27.42, 26.81, 26.24, 24.86, 21.28, 10.81.

Example 2

Synthesis of (5Z,11Z)-16-(3-Ethyloxirane-2-yl)hexadeca-5,11-dienoic acid (2)

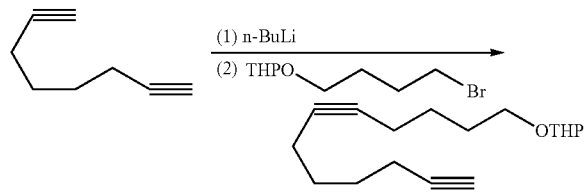

Oct-1,7-diyne (9.0 g, 84.9 mmol; G F Smith) was alkylated with 2-(4-bromobutoxy)-tetrahydropyran (15 g, 63.68 mmol) as described above for the synthesis of 2-(pentadeca-5,14-diynyloxy)tetrahydropyran to give 2-(dodeca-5,11-diynyloxy)tetrahydropyran (10.85 g, 65%) as a colorless oil. TLC: 10% EtOAc/hexanes, R$_f$≈0.6; $^1$H NMR (400 MHz, CDCl$_3$) δ 4.57 (t, J=2.5 Hz, 1H), 3.82-3.87 (m, 1H), 3.70-3.77 (m, 1H), 3.46-3.51 (m, 1H), 3.36-3.42 (m, 1H), 2.14-2.20 (m, 6H), 1.93 (t, 1H, J=2.5 Hz), 1.46-1.72 (m, 14H).

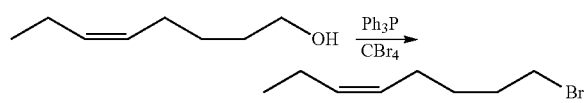

A solution of carbon tetrabromide (10.8 g, 32.94 mmol) in CH$_2$Cl$_2$ (25 mL) was stirred into a 0° C. solution of triphenylphosphine (8.6 g, 32.94 mmol) and oct-5(Z)-en-1-ol (2.8 g, 14.06 mmol) in dry CH$_2$Cl$_2$ (100 mL) under an argon atmosphere. After 30 min, the reaction mixture was washed with water (75 mL), brine (50 mL), dried over anhydrous Na$_2$SO$_4$, and all volatiles were removed under reduced pressure. The residue was purified by fractional distillation to afford 8-bromo-oct-3(Z)-ene (2.01 g, 75%) as a light yellow oil. TLC: 10% EtOAc/hexanes, R$_f$≈0.7; $^1$H NMR (400 MHz, CDCl$_3$) δ 5.26-5.45 (m, 2H), 3.42 (t, 2H, J=7.6 Hz), 1.98-2.22 (m, 4H), 1.63-1.82 (m, 2H), 1.46-1.54 (m, 2H), 0.95 (t, 3H, J=7.3 Hz). Lit. ref: R. M. Seifert *J. Agric. Food Chem.* 1981: 29, 647.

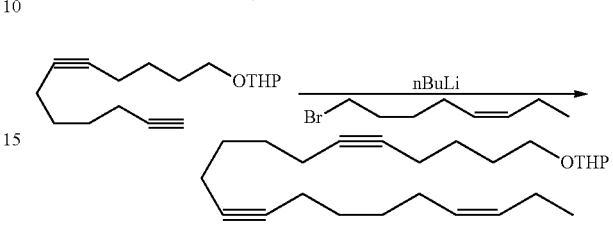

n-BuLi (2.5 M solution in hexanes, 20.65 mmol), 2-(dodeca-5,11-diynyloxy)tetrahydropyran (4.5 g, 17.2 mmol), and 8-bromo-oct-3(Z)-ene (4.1 g, 21.5 mmol) were reacted as described above for the synthesis of 2-(pentadeca-5,14-diynyloxy)tetrahydropyran to give 2-[eicos-17(Z)-ene-5,11-diynyloxy]tetrahydropyran (4.15 g, 65%) as a colorless oil. TLC: 10% EtOAc/hexanes, R$_f$≈0.6; $^1$H NMR (400 MHz, CDCl$_3$) δ 5.26-5.41 (m, 2H), 4.58 (t, J=2.5 Hz, 1H), 3.82-3.87 (m, 1H), 3.70-3.77 (m, 1H), 3.46-3.51 (m, 1H), 3.36-3.42 (m, 1H), 2.11-2.20 (m, 8H), 1.92-2.04 (m, 4H), 1.62-1.86 (m, 4H), 1.39-1.69 (m, 14H), 0.94 (t, 3H, J=7.5 Hz).

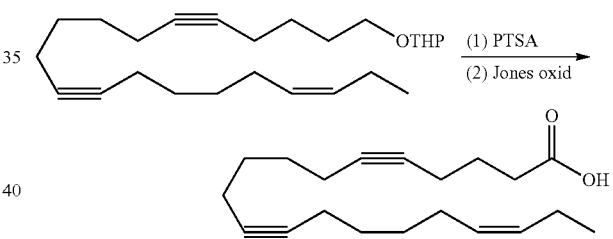

A solution of 2-[eicos-17(Z)-ene-5,11-diynyloxy]tetrahydropyran (1.3 g, 3.49 mmol) and p-toluenesulphonic acid (50 mg; PTSA) in MeOH (50 mL) was stirred at room temperature for 4 h, then concentrated in vacuo. The residue was purified by SiO$_2$ column chromatography using 15% EtOAc/hexanes as eluent to give eicosa-17(Z)-ene-5,11-diyn-1-ol (925 mg, 92%) as a colorless oil. TLC: 30% EtOAc/hexanes, R$_f$≈0.35; $^1$H NMR (400 MHz, CDCl$_3$) δ 5.27-5.42 (m, 2H), 3.66 (t, 2H, J=6.8 Hz), 2.00-2.19 (m, 12H), 1.43-1.72 (m, 12H), 0.95 (t, 3H, J=7.7 Hz).

Jones reagent (5 mL of a 10 N aq. solution) in acetone (10 mL) was added slowly to a stirring, −40° C. solution of eicosa-17(Z)-ene-5,11-diyn-1-ol (1.0 g, 3.47 mmol) in acetone (50 mL). After 1 h, the reaction mixture was warmed to −10° C., maintained at this temperature for 3 h, then quenched with excess (5 equiv) isopropanol. The green chromium salts were removed by filtration, the filter cake was washed with acetone, and the combined filtrates were concentrated in vacuo. The residue was dissolved in ethyl acetate (100 mL), washed with water (50 mL), and concentrated in vacuo. The residue was purified by SiO$_2$ column chromatography using 15% EtOAc/hexanes as eluent to give eicosa-17(Z)-ene-5,11-diynoic acid (920 mg, 88%) as a colorless oil. TLC: 30% EtOAc/hexanes, R$_f$≈0.35; $^1$H NMR (400 MHz, CDCl$_3$) δ 5.24-5.41 (m, 2H), 2.41 (t, 3H, J=6.9 Hz), 2.10-2.19 (m, 8H), 1.98-2.09 (m, 4H), 1.75-1.81 (m, 2H), 0.96 (t, 3H, J=7.7 Hz).

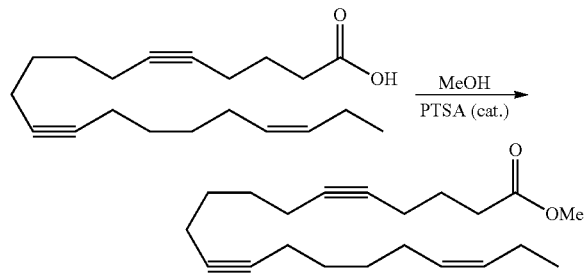

A solution of eicosa-17(Z)-ene-5,11-diynoic acid (0.8 g, 2.63 mmol) and PTSA (20 mg) in MeOH (30 mL) was stirred at room temperature for 10 h, then concentrated in vacuo and the residue was purified by SiO$_2$ column chromatography using 3% EtOAc/hexanes as eluent to give methyl eicos-17(Z)-ene-5,11-diynoate (682 mg, 82%) as a colorless oil. TLC: 10% EtOAc/hexanes, R$_f$=0.60; $^1$H NMR (400 MHz, CDCl$_3$) δ 5.27-5.42 (m, 2H), 3.67 (s, 3H), 2.43 (t, 2H, J=7.6 Hz), 2.12-2.21 (m, 8H), 1.99-2.09 (m, 4H), 1.76-1.82 (m, 2H), 1.42-1.58 (m, 8H), 0.95 (t, 3H, J=7.7 Hz).

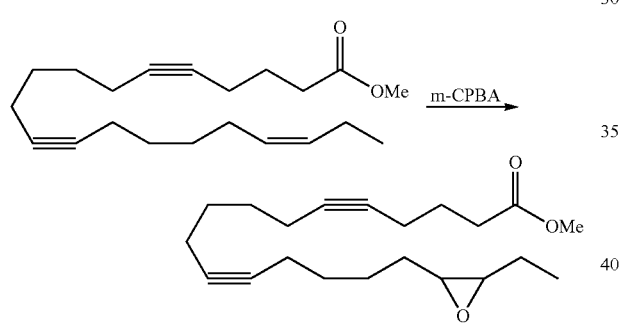

m-Chloroperbenzoic acid (1.6 g, 4.76 mmol; m-CPBA) was added to a 0° C. solution of methyl eicosa-17(Z)-ene-5,11-diynoate (1.15 g, 3.66 mmol) in CH$_2$Cl$_2$ (50 mL). After 2 h at room temperature, the reaction mixture was diluted with CH$_2$Cl$_2$ (25 mL), washed with sat. aq. NaHCO$_3$ (2×25 mL), brine (2×25 mL), water (50 mL), dried over Na$_2$SO$_4$, and concentrated under reduced pressure. The residue was purified by SiO$_2$ column chromatography using 5% EtOAc/hexanes as eluent to give methyl 16-[(Z)-3-ethyloxiranyl]hexadeca-5,11-diynoate (990 mg, 82%) as colorless oil. TLC: 10% EtOAc/hexanes, R$_f$=0.3; $^1$H NMR (400 MHz, CDCl$_3$) δ 3.67 (s, 3H), 2.84-2.94 (m, 2H), 2.42 (t, 2H, J=7.3 Hz), 2.14-2.23 (m, 8H), 1.74-1.83 (m, 2H), 1.42-1.61 (m, 12H), 1.03 (t, 3H, J=7.6 Hz).

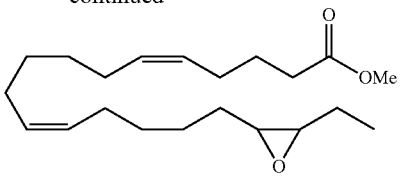

Methyl 16-[(Z)-3-ethyloxiranyl]hexadeca-5,11-diynoate (250 mg, 0.75 mmol) was subjected to semi-hydrogenation as described above for the synthesis of methyl 16-[(Z)-3-ethyloxiranyl]hexadeca-5(Z),14(Z)-dienoate to give methyl 16-[(Z)-3-ethyloxiranyl]hexadeca-5(Z),11(Z)-dienoate (246 mg, 98%) as a colorless oil. TLC: 20% EtOAc/hexanes, R$_f$=0.65; $^1$H NMR (400 MHz, CDCl$_3$) δ 5.27-5.42 (m, 4H), 3.66 (s, 3H), 2.83-2.93 (m, 2H), 2.30 (t, 2H, J=7.3 Hz), 1.92-2.09 (m, 8H), 1.63-1.72 (m, 2H), 1.25-1.58 (m, 12H), 1.03 (t, 3H, J=7.7 Hz); $^{13}$C NMR (100 MHz, CDCl$_3$) δ 174.45, 131.24, 130.04, 129.68, 128.88, 58.30, 56.75, 51.65, 33.63, 29.92, 29.76, 27.94, 29.74, 27.36, 26.86, 26.52, 25.54, 21.36, 10.89. Lit. ref: J. R. Falck; L. M. Reddy; Y. K. Reddy; M. Bondlela; U. M. Krishna; Y. Ji; J. Sun.; J. K. Liao *Bioorg. Med. Chem. Lett.* 2003: 13, 4011.

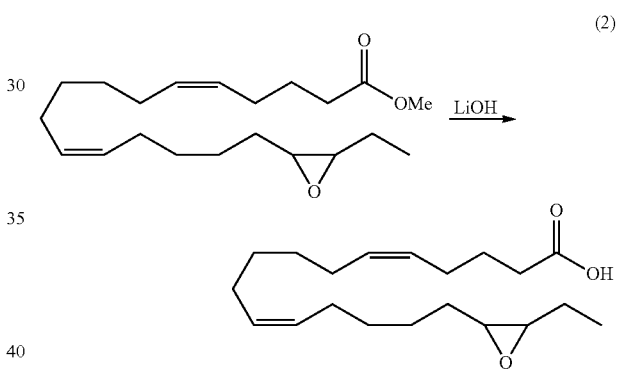

Methyl 16-[(Z)-3-ethyloxiranyl]hexadeca-5(Z),11(Z)-dienoate (0.25 g, 0.74 mmol) was hydrolyzed as described above for 16-[(Z)-3-ethyloxiranyl]hexadeca-5(Z),14(Z)-dienoic acid to give 16-[(Z)-3-ethyloxiranyl]hexadeca-5(Z),11(Z)-dienoic acid (222 mg, 93%) as a colorless oil. TLC: 30% EtOAc/hexanes, R$_f$=0.3; $^1$H NMR (400 MHz, CDCl$_3$) δ 5.28-5.40 (m, 4H), 2.87-2.97 (m, 2H), 2.34 (t, 3H, J=7.0 Hz), 1.97-2.12 (m, 8H), 1.63-1.74 (m, 2H), 1.30-1.60 (m, 12H), 1.02 (t, 3H, J=7.4 Hz); $^{13}$C NMR (300 MHz, CDCl$_3$) δ 180.06, 131.75, 130.03, 129.77, 128.66, 58.86, 57.87, 33.93, 29.93, 29.84, 29.81, 27.89, 27.68, 26.41, 26.36, 24.83, 21.26, 10.84.

Example 3

Synthesis of (8Z,14Z)-16-(3-Ethyloxirane-2-yl)hexadeca-8,14-dienoic Acid (3)

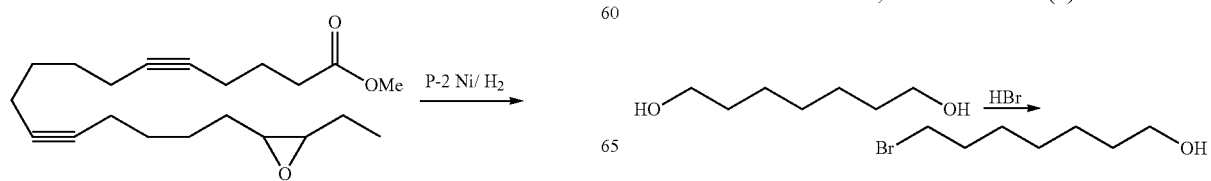

Heptane-1,7-diol (36.0 g, 272 mmol; Alfa Aesar) and aq. 48% HBr (38 mL) were heated under reflux in benzene (400 mL) with water removal using a Dean-Stark apparatus. After 12 h, all volatiles were removed in vacuo and the residue was purified by SiO$_2$ column chromatography using a gradient of 10-30% EtOAc/hexanes as eluent to give 7-bromoheptan-1-ol (26.22 g, 62%) as colorless oil. TLC: 50% EtOAc/hexanes, R$_f$=0.4; $^1$H NMR (400 MHz, CDCl$_3$) δ 3.61 (t, 2H, J=7.1 Hz), 3.39 (t, 2H, J=6.8 Hz), 1.80-1.88 (m, 2H), 1.52-1.58 (m, 2H), 1.30-1.46 (m, 6H).

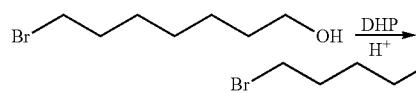

7-Bromoheptane-1-ol (11.0 g, 56.7 mmol) from above was protected as its THP ether as described previously to give 2-(7-bromoheptyloxy)tetrahydro-2H-pyran (14.50 g, 92%) as colorless oil. TLC: 10% EtOAc/hexanes, R$_f$=0.5; $^1$H NMR (400 MHz, CDCl$_3$) δ 4.58 (m, J=2.5 Hz, 1H), 3.84-3.88 (m, 1H), 3.68-3.77 (m, 1H), 3.46-3.3.51 (m, 1H), 3.33-3.43 (m, 3H), 1.80-1.81 (m, 2H), 1.30-1.62 (m, 14H).

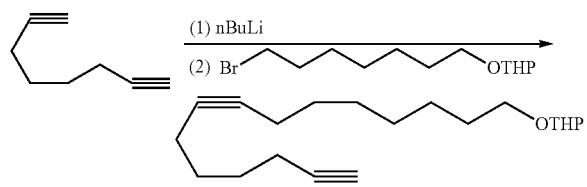

Oct-1,7-diyne (6.3 g, 59.3 mmol) was alkylated with 2-(7-bromoheptyloxy)tetrahydro-2H-pyran (11 g, 39.56 mmol) as described above to give 2-(pentadeca-8,14-diynyloxy)tetrahydro-2H-pyran (7.82 g, 64%) as colorless oil. TLC: 10% EtOAc/hexanes, R$_f$=0.6; $^1$H NMR (400 MHz, CDCl$_3$) δ 4.57 (t, J=2.5 Hz, 1H), 3.82-3.87 (m, 1H), 3.70-3.77 (m, 1H), 3.46-3.51 (m, 1H), 3.36-3.42 (m, 1H), 2.14-2.20 (m, 6H), 1.93 (t, J=2.6 Hz, 1H), 1.46-1.72 (m, 20H)

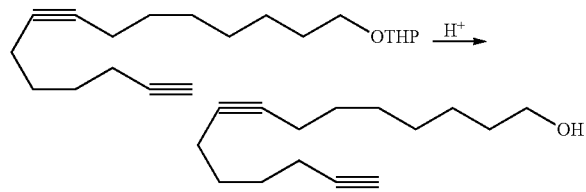

2-(Pentadeca-8,14-diynyloxy)tetrahydro-2H-pyran (5 g, 16.45 mmol) was cleaved using p-toluenesulphonic acid (60 mg) in MeOH (100 mL) as described above and the product was purified by SiO$_2$ column chromatography using 15% EtOAc/hexanes as eluent to give pentadeca-8,14-diyn-1-ol (3.26 g, 90%) as a colorless oil. TLC: 30% EtOAc/hexanes, R$_f$=0.35; $^1$H NMR (400 MHz, CDCl$_3$) δ 3.63 (t, 2H, J=5.5 Hz), 2.10-2.18 (m, 6H), 1.93 (t, 1H, J=2.6 Hz), 1.24-1.62 (m, 14H).

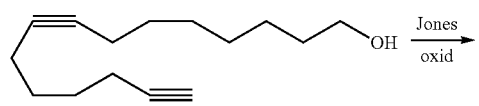

Oxidation of pentadeca-8,14-diyn-1-ol (3.0 g, 13.69 mmol) using Jones reagent as described above and purification by SiO$_2$ column chromatography using 15% EtOAc/hexanes as eluent gave pentadeca-8,14-diynoic acid (2.80 g, 87%) as a colorless oil. TLC: 30% EtOAc/hexanes, R$_f$=0.33; $^1$H NMR (400 MHz, CDCl$_3$) δ 2.34 (t, J=7.0 Hz, 2H), 2.10-2.18 (m, 6H), 1.93 (t, J=2.6 Hz, 1H,), 1.55-1.67 (m, 6H), 1.33-1.49 (m, 6H).

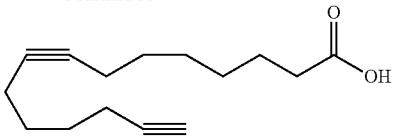

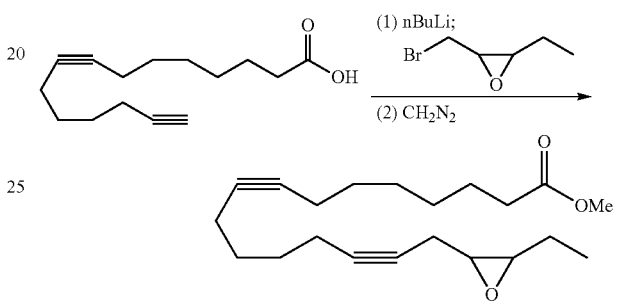

Pentadeca-8,14-diynoic acid (0.80 g, 3.42 mmol) was alkylated with (Z)-2-(bromomethyl)-3-ethyloxirane (0.74 g, 4.10 mmol) and esterified using diazomethane as described above to give methyl 16-[(Z)-3-ethyloxiranyl]hexadeca-5,14-diynoate to give methyl 16-[(Z)-3-ethyloxiran-2-yl]hexadeca-8,14-diynoate (658 mg, 58%) as a colorless oil. TLC: 10% EtOAc/hexanes, R$_f$=0.5; $^1$H NMR (400 MHz, CDCl$_3$) δ 3.65 (s, 3H), 3.07-3.12 (m, 1H), 2.88-2.92 (m, 1H), 2.51-2.61 (m, 1H), 2.32-2.50 (m, 1H), 2.30 (t, J=7.5 Hz, 3H), 2.08-2.25 (m, 6H), 1.25-1.65 (m, 14H), 1.06 (t, J=7.3 Hz, 3H)

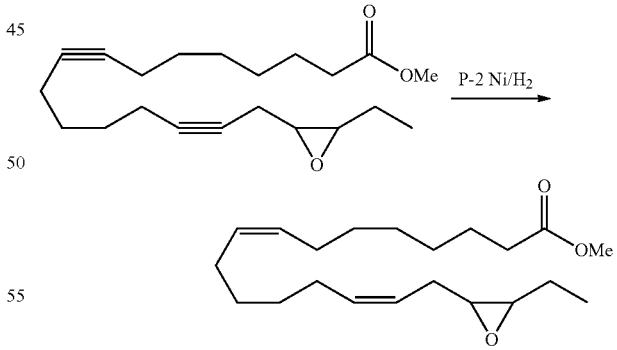

Methyl 16-[(Z)-3-ethyloxiranyl]hexadeca-8,14-diynoate was subjected to the semi-hydrogenation procedure above to give methyl 16-[(Z)-3-ethyloxiranyl]hexadeca-8(Z),14(Z)-dienoate (97%) as a colorless oil. TLC: 20% EtOAc/hexanes, R$_f$=0.55; $^1$H NMR (400 MHz, CDCl$_3$) δ 5.31-5.56 (m, 4H), 3.66 (s, 3H), 2.86-2.96 (m, 2H), 2.25-2.42 (m, 1H), 2.28 (t, 2H, J=7.33 Hz), 2.12-2.20 (m, 1H), 1.96-2.08 (m, 6H), 1.52-1.64 (m, 4H), 1.26-1.39 (m, 10H), 1.03 (t, 3H, J=7.3 Hz); $^{13}$C NMR (100 MHz, CDCl$_3$) δ 174.30, 132.60, 129.99, 129.84, 124.13, 58.40, 56.73, 51.51, 34.17, 29.66, 29.47, 29.30, 29.18, 29.03, 27.46, 27.27, 27.20, 26.28, 25.05, 21.21, 10.76.

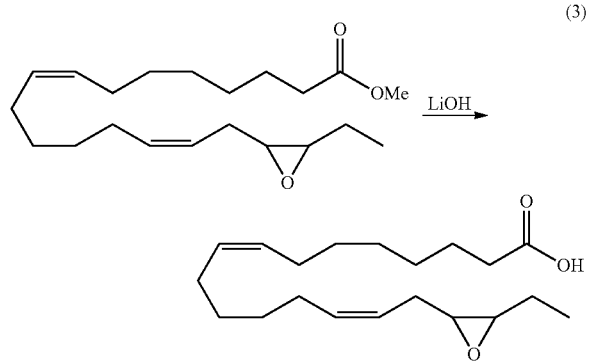

Methyl 16-[(Z)-3-ethyloxiranyl]hexadeca-8(Z),14(Z)-dienoate was hydrolyzed as described above to give 16-[(Z)-3-ethyloxiranyl]hexadeca-8(Z),14(Z)-dienoic acid (93%) as a colorless oil. TLC: 30% EtOAc/hexanes, $R_f$≈0.3; $^1$H NMR (300 MHz, CDCl$_3$) δ 5.31-5.53 (m, 4H), 2.87-2.98 (m, 2H), 2.33-2.43 (m, 1H), 2.33 (t, J=7.3 Hz, 2H), 2.13-2.22 (m, 1H), 1.94-2.08 (m, 6H), 1.52-1.64 (m, 4H), 1.30-1.38 (m, 10H), 1.04 (t, J=7.4 Hz, 3H); $^{13}$C NMR (75 MHz, CDCl$_3$) δ 180.06, 132.54, 130.03, 130.01, 125.03, 58.87, 57.73, 34.16, 29.86, 29.74, 29.71, 29.52, 29.45, 27.84, 27.67, 27.42, 26.33, 24.75, 21.48, 10.82.

Example 4

Synthesis of 16-[(Z)-3-Ethyloxiranyl]hexadec-11(Z)-enoic Acid (4), 16-[(Z)-3-Ethyloxiranyl]hexadec-5(Z)-enoic Acid (7), and 16-[(Z)-3-Ethyloxiranyl]hexadecanoic Acid (8)

A stream of dry air was passed through a stirring solution of hydrazine hydrate (400 mg, 12 mmol, 20 equiv), methyl 16-[(Z)-3-ethyloxiranyl]hexadeca-5(Z),11(Z)-dienoate (200 mg, 0.60 mmol), and CuSO$_4$.5H$_2$O (10 mg) in ethanol (5 mL). The stream of air was passed through EtOH to saturated it with ethanol and help maintain the reaction volume. After 12 h, the reaction mixture was passed through a short pad of silica gel and the filter cake was washed with dichloromethane (3×10 mL). The combined filtrates were dried over anhydrous Na$_2$SO$_4$, and concentrated in vacuo. The residue was resolved into its components by AgNO$_3$-impregnated PTLC using 2% CH$_2$Cl$_2$/benzene: $R_f$≈0.2, 0.4, 0.55, and 0.85 for methyl 16-[(Z)-3-ethyloxiranyl]hexadeca-5(Z),11(Z)-dienoate, methyl 16-[(Z)-3-ethyloxiranyl]hexadec-11(Z)-enoate, methyl 16-[(Z)-3-ethyloxiranyl]hexadec-5(Z)-enoate, and methyl 16-[(Z)-3-ethyloxiranyl]hexadecanoate, respectively, isolated in a ratio of 2:3:3:2, respectively. Lit. ref: E. J. Corey; T. M. Eckrich *Tetrahedron Lett.* 1984: 25, 2415.

Methyl 16-[(Z)-3-ethyloxiranyl]hexadec-5(Z)-enoate: $^1$H NMR (400 MHz, CDCl$_3$) δ 5.27-5.42 (m, 2H), 3.66 (s, 3H), 2.84-2.92 (m, 2H), 2.30 (t, J=7.4 Hz, 2H), 1.96-2.08 (m, 4H), 1.64-1.71 (m, 2H), 1.45-1.58 (m, 4H), 1.21-1.36 (m, 16H), 1.03 (t, J=7.3 Hz, 3H); $^{13}$C NMR (100 MHz, CDCl$_3$) δ 174.45, 131.88, 128.63, 58.64, 57.87, 51.96, 33.88, 29.99, 29.86, 29.74, 29.46, 27.98, 27.76, 26.88, 26.72, 25.88, 21.32, 10.48.

Methyl 16-[(Z)-3-ethyloxiranyl]hexadec-11(Z)-enoate: $^1$H NMR (300 MHz, CDCl$_3$) 5.25-5.35 (m, 2H), 3.61 (s, 3H), 2.79-2.89 (m, 2H), 2.25 (t, J=7.3 Hz, 2H), 1.93-2.04 (m, 4H), 1.19-1.60 (m, 22H), 1.00 (t, J=7.2 Hz, 3H); $^{13}$C NMR (100 MHz, CDCl$_3$) δ 174.48, 130.41, 129.54, 58.54, 57.45, 51.62, 34.27, 29.92, 29.81, 29.67, 29.63, 29.47, 29.46, 29.34, 27.80, 27.42, 27.27, 26.42, 25.14, 10.82.

Methyl 16-[(Z)-3-ethyloxiranyl]hexadecanoate: $^1$H NMR (400 MHz, CDCl$_3$) δ 3.67 (s, 3H), 2.84-2.94 (m, 2H), 2.31 (t, 2H, J=7.4 Hz), 1.42-1.65 (m, 6H), 1.22-1.34 (m, 24H), 1.04 (t, 3H, J=7.3 Hz).

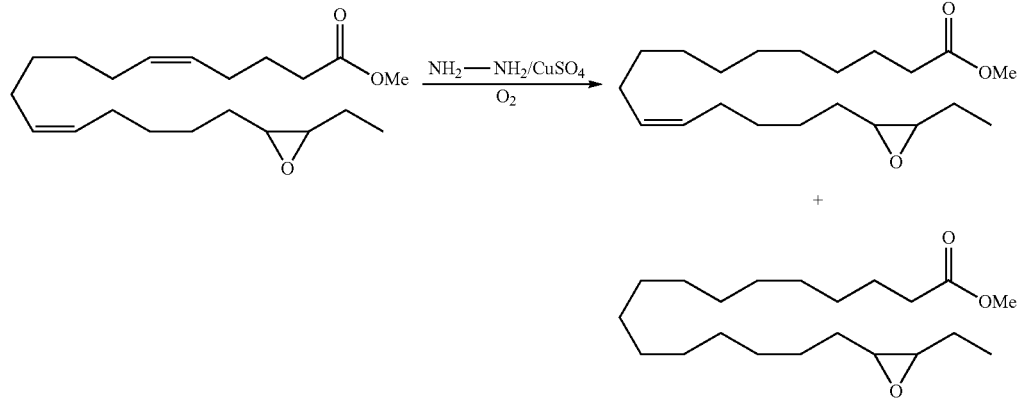

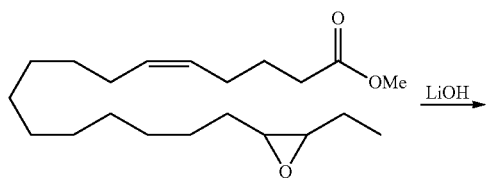
(7)

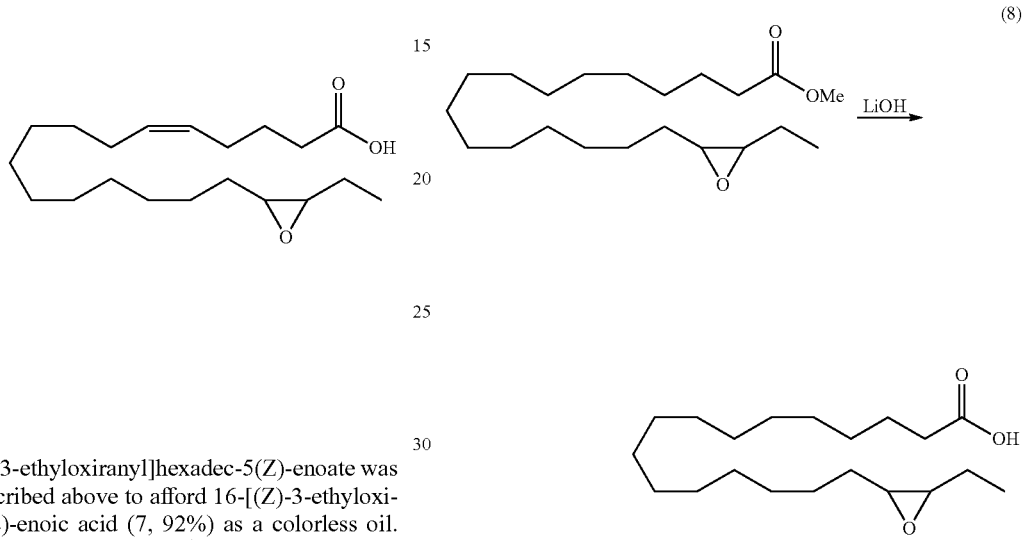
(8)

Methyl 16-[(Z)-3-ethyloxiranyl]hexadec-11(Z)-enoate was hydrolyzed as described above to afford 16-[(Z)-3-ethyloxiranyl]hexadec-11(Z)-enoic acid (4, 92%) as a colorless oil. TLC: SiO$_2$, 30% EtOAc/hexanes, R$_f$≈0.3; $^1$H NMR (300 MHz, CDCl$_3$) δ 5.28-5.40 (m, 2H), 2.84-2.94 (m, 2H), 2.31 (t, J=7.6 Hz, 2H), 1.96-2.04 (m, 4H), 1.02-1.62 (m, 22H), 1.01 (t, 3H, J=7.4 Hz); $^{13}$C NMR (75 MHz, CDCl$_3$) δ 180.10, 130.45, 129.57, 58.74, 57.67, 34.27, 29.92, 29.81, 29.66, 29.60, 29.46, 29.43, 29.25, 27.76, 27.43, 27.28, 26.41, 24.89, 21.27, 10.81.

Methyl 16-[(Z)-3-ethyloxiranyl]hexadec-5(Z)-enoate was hydrolyzed as described above to afford 16-[(Z)-3-ethyloxiranyl]hexadec-5(Z)-enoic acid (7, 92%) as a colorless oil. TLC: 30% EtOAc/hexanes, R$_f$≈0.3; $^1$H NMR (300 MHz, CDCl$_3$) δ 5.27-5.43 (m, 2H), 2.85-2.93 (m, 2H), 2.34 (t, J=7.6 Hz, 2H), 1.95-2.11 (m, 4H), 1.64-1.72 (m, 2H), 1.49-1.60 (m, 4H), 1.22-1.36 (m, 16H), 1.03 (t, J=7.4 Hz, 3H); $^{13}$C NMR (75 MHz, CDCl$_3$) δ 179.42, 131.54, 128.40, 60.08, 58.75, 57.73, 34.59, 31.86, 29.86, 29.74, 29.71, 29.45, 27.84, 27.42, 26.81, 26.64, 24.85, 21.28, 15.47, 10.81.

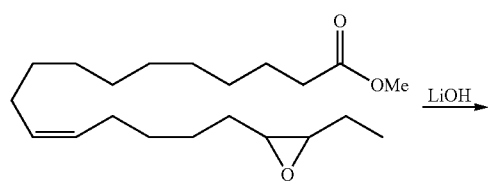
(4)

Methyl 16-[(Z)-3-ethyloxiranyl]hexadecanoate was hydrolyzed as described above to afford 16-[(Z)-3-ethyloxiranyl]hexadecanoic acid (8, 94%) as white solid. M.P.: 62.1-62.5° C., TLC: 30% EtOAc/hexanes, R$_f$≈0.35; $^1$H NMR (400 MHz, CDCl$_3$) δ 2.86-2.94 (m, 2H), 2.34 (t, 2H, J=7.3 Hz), 1.46-1.65 (m, 30H), 1.04 (t, 3H, J=7.35 Hz); $^{13}$C NMR (100 MHz, CDCl$_3$) δ 180.04, 58.83, 57.47, 34.24, 30.06, 30.03, 29.92, 29.81, 29.66, 29.60, 29.46, 29.43, 29.25, 27.76, 27.43, 27.28, 26.41, 24.89, 21.27, 10.89.

Enantiomeric Resolution of Methyl 16-[(Z)-3-ethyloxiranyl]hexadec-11(Z)-enoate by Chiral HPLC Chromatography of methyl 16-[(Z)-3-ethyloxiranyl]hexadec-11(Z)-enoate using a Chiralcel® OJ-H column (250×4.6 mm) with hexane/iPrOH (99.7:0.3) at a flow rate of 1 mL/min, uv detector at 195 nm, furnished the R,S-enantiomer (R$_t$=15.17 min) and S,R-enantiomer (R$_t$=17.68 min). Preparative separation: Chiralcel® OJ-H column (250×20 mm) using hexane/iPrOH (99.5:0.5) at a flow rate of 8 mL/min, uv detector at 195 nm, injecting 7 mg/100 μL in mobile phase.

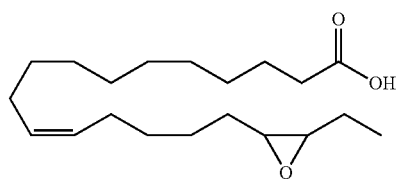

Example 5

Synthesis of 16-[(Z)-3-Ethyloxiranyl]hexadec-14(Z)-enoic Acid (5), 16-[(Z)-3-Ethyloxiranyl]hexadec-8(Z)-enoic Acid (6) and 16-[(Z)-Ethyloxiranyl]hexadec-14(Z)-enoic Acid (8)

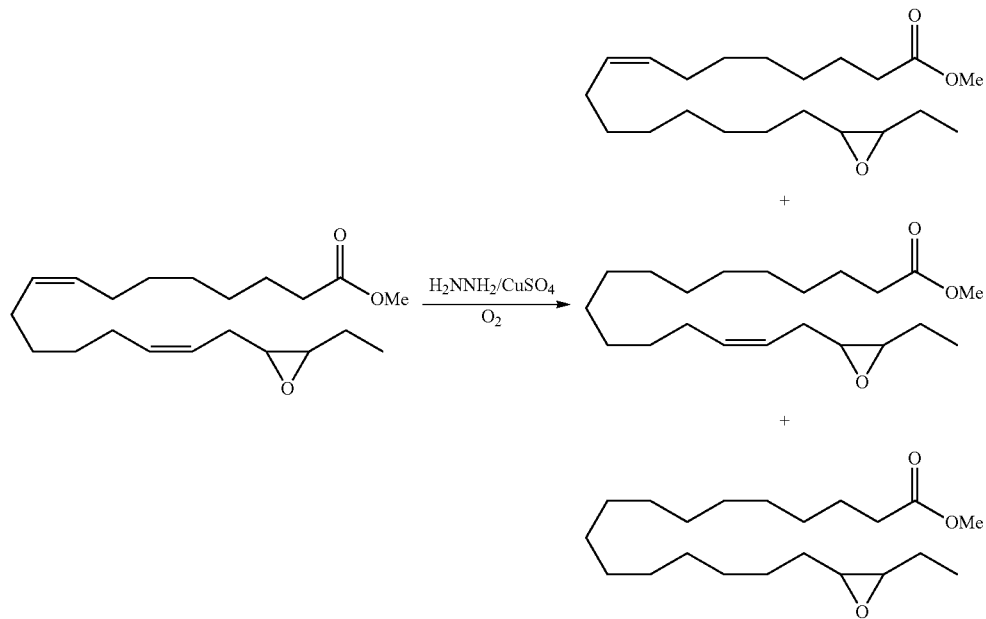 [SMILES: CCC1OC1CCCCCCC/C=C\CCCCCCC(=O)OC ; CCC1OC1C/C=C\CCCC/C=C\CCCCCCC(=O)OC ; "O2" ; CCC1OC1C/C=C\CCCCCCCCCCCCC(=O)OC ; CCC1OC1CCCCCCCCCCCCCCCC(=O)OC]

Methyl 16-[(Z)-3-ethyloxiranyl]hexadeca-8(Z),14(Z)-dienoate was partially reduced using diimide as described above. AgNO$_3$-impregnated PTLC using 2% CH$_2$Cl$_2$/benzene: R$_f$=0.2, 0.5, 0.6, and 0.85 for methyl 16-[(Z)-3-ethyloxiranyl]hexadeca-8(Z),14(Z)-dienoate, methyl (Z)-16-(3-ethyloxiranyl)hexadec-14(Z)-enoate, methyl 16-[(Z)-3-ethyloxiranyl]hexadec-8(Z)-enoate, and methyl 16-[(Z)-3-ethyloxiranyl]hexadecanoate, respectively, isolated in a ratio of 2:3:3:2, respectively.

Methyl 16-[(Z)-3-ethyloxiranyl]hexadec-8(Z)-enoate: $^1$H NMR (300 MHz, CDCl$_3$) δ 5.31-5.35 (m, 2H), 3.66 (s, 3H), 2.84-2.91 (m, 2H), 2.27 (t, J=7.3 Hz, 2H,), 1.97-2.08 (m, 4H), 1.47-1.64 (m, 4H), 1.22-1.39 (m, 18H), 1.03 (t, J=7.3 Hz, 3H).

Methyl 16-[(Z)-ethyloxiranyl]hexadec-14(Z)-enoate: $^1$H NMR (300 MHz, CDCl$_3$) δ 5.35-5.53 (m, 2H), 3.63 (s, 3H), 2.84-2.95 (m, 2H), 2.32-2.39 (m, 1H), 2.27 (t, J=7.3 Hz, 2H), 2.12-2.95 (m, 1H), 1.98-2.04 (m, 2H), 1.48-1.64 (m, 4H), 1.20-1.34 (m, 18H), 1.04 (t, J=7.4 Hz, 3H); $^{13}$C NMR (75 MHz, CDCl$_3$) 174.62, 132.86, 123.86, 58.84, 56.92, 51.76, 34.48, 29.96, 29.89, 29.84, 29.79, 29.74, 29.68, 29.66, 29.59, 29.57, 27.76, 26.36, 25.17, 21.33, 10.07.

-continued

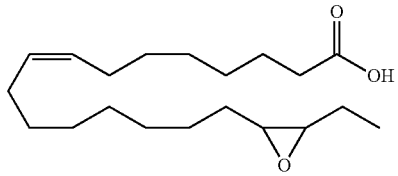

Methyl 16-[(Z)-3-ethyloxiranyl]hexadec-8(Z)-enoate was hydrolyzed as described above to afford 16-[(Z)-3-ethyloxiranyl]hexadec-8(Z)-enoic acid (6, 91%) as a colorless oil. TLC: 30% EtOAc/hexanes, R$_f$=0.33; $^1$H NMR (400 MHz, CDCl$_3$) δ 5.34-5.40 (m, 2H), 2.90-2.96 (m, 2H), 2.36 (t, 2H, J=7.7 Hz), 2.01-2.05 (m, 4H), 1.22-1.65 (m, 22H), 1.07 (t, 3H, J=7.4 Hz); $^{13}$C NMR (75 MHz, CDCl$_3$) δ 180.08, 130.52, 129.66, 58.54, 57.47, 34.23, 29.81, 29.61, 29.56, 29.36, 29.16, 29.13, 29.07, 28.86, 27.53, 26.78, 26.61, 24.49, 21.46, 10.78.

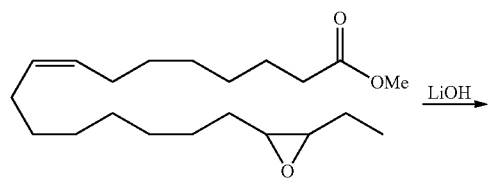

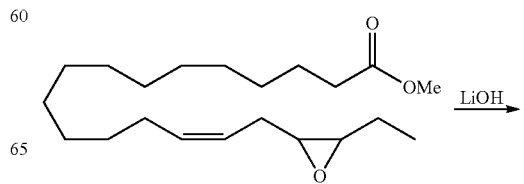

-continued

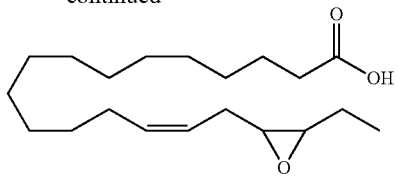

Methyl 16-[(Z)-3-ethyloxiranyl]hexadec-14(Z)-enoate was hydrolyzed as described above to afford 16-[(Z)-3-ethyloxiranyl]hexadec-14(Z)-enoic acid (5, 90%). TLC: 30% EtOAc/hexanes, $R_f \approx 0.32$; $^1$H NMR (300 MHz, CDCl$_3$) δ 5.36-5.59 (m, 2H), 2.87-2.98 (m, 2H), 2.34 (t, J=7.6 Hz, 2H), 2.31-2.43 (m, 1H), 2.12-2.22 (m, 1H), 1.99-2.06 (m, 2H), 1.50-1.64 (m, 4H), 1.20-1.35 (m, 18H), 1.04 (t, J=7.3 Hz, 3H); $^{13}$C NMR (75 MHz, CDCl$_3$) δ 180.04, 133.06, 123.96, 58.46, 57.42, 34.12, 30.04, 30.01, 30.00, 29.98, 29.84, 29.96, 29.92, 29.89, 29.87, 27.88, 26.38, 25.01, 21.27, 10.92.

Example 6

Synthesis of 16-(3-Ethylureido)hexadec-11(Z)-enoic Acid (11)

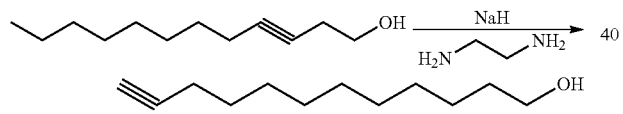

NaH (7.5 g, 60% oil dispersion, 326 mmol) was added portionwise to a stirring, 0° C. solution of dodec-3-yn-1-ol (10.0 g, 54.95 mmol; GF Smith) in ethylenediamine (40 mL). After 1 h, the temperature was raised to 70° C. After another 8 h, the reaction mixture was cooled to 0° C., carefully quenched with ice cold water (100 mL), and extracted with ether (3×60 mL). The combined ethereal extracts were washed with water (100 mL). The aqueous wash was back-extracted with ether (3×60 mL). The combined organic extracts were concentrated in vacuo and the residue subjected to column chromatography using 10% EtOAc/hexanes afforded dodec-10-yn-1-ol (7.4 g, 74%) contaminated with 3-5% of other regioisomers. TLC: 30% EtOAc/hexane, $R_f \approx 0.4$; $^1$H NMR (300 MHz, CDCl$_3$) δ 3.66 (t, 2H, J=7.3 Hz), 2.14-2.21 (m, 2H), 1.93 (t, J=1.9 Hz, 1H), 1.20-1.63 (m, 16H). Lit. ref: R. V. Novikov; A. A. Vasil'ev; I. A. Balova *Russ. Chem. Bull., Internat. Ed.* 2005: 54, 1043-1045.

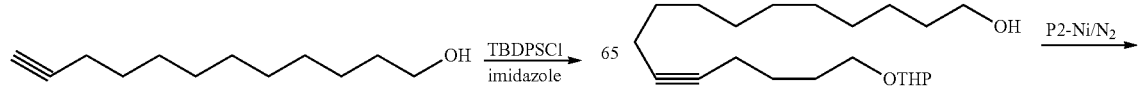

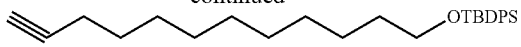

tert-Butyldiphenylsilyl chloride (TBDPSCl, 8.70 g, 31.65 mmol) was slowly added to a 0° C. solution of dodec-11-yn-1-ol (4.80 g, 26.37 mmol) and imidazole (3.23 g, 47.47 mmol) in anhydrous dichloromethane (100 mL). After stirring at room temperature for 3 h, the reaction mixture was washed with water (75 mL), brine (50 mL), and concentrated under reduced pressure. The residue was purified by SiO$_2$ column chromatography using 3% EtOAc/hexanes as eluent to give 12-(tert-butyldiphenylsilyloxy)dodec-1-yne (9.75 g, 88%) as a colorless oil. TLC: 6% EtOAc/hexanes, $R_f \approx 0.7$; $^1$H NMR (CDCl$_3$, 300 MHz) δ 7.65-7.68 (m, 4H), 7.34-7.42 (m, 6H), 3.65 (t, J=7.3 Hz, 2H), 2.18 (dt, J=7.0, 2.4 Hz, 2H), 1.94 (t, J=1.9 Hz, 1H), 1.20-1.60 (m, 16H), 1.04 (s, 9H).

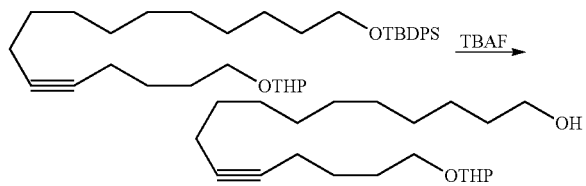

Alkylation of 12-(tert-butyldiphenylsilyloxy)dodec-1-yne with 2-(4-bromobutoxy)tetrahydropyran as described above gave tert-butyldiphenyl-[16-(tetrahydropyran-2-yloxy)hexadec-11-ynyloxy]silane (66%) as a colorless oil which was used in the next reaction without further purification. TLC: 10% EtOAc/hexane, $R_f \approx 0.5$.

Tetra-n-butylammonium fluoride (3.14 g, 12.5 mL of a 1 M soln in THF, 12.50 mmol) was added to a solution of the above crude tert-butyldiphenyl-[16-(tetrahydropyran-2-yloxy)hexadec-11-ynyloxy]silane (6 g, 10.42 mmol) in THF (150 mL) under an argon atmosphere. After 5 h, the reaction mixture was quenched with sat. aq. NH$_4$Cl (5 mL), washed with water (100 mL), and brine (75 mL). The aqueous layer was back-extracted with ether (2×75 mL). The combined organic extracts were dried over Na$_2$SO$_4$, concentrated under reduced pressure, and the residue was purified by SiO$_2$ column chromatography using 5-10% EtOAc/hexanes as eluent to give 16-(tetrahydro-2H-pyran-2-yloxy)hexadec-11-yn-1-ol (3.17 g, 80% overall) as a colorless oil. TLC: 40% EtOAc/hexanes, $R_f \approx 0.4$; $^1$H NMR (CDCl$_3$, 300 MHz) 4.57-4.59 (m, 1H), 3.82-3.90 (m, 1H), 3.71-3.79 (m, 1H), 3.64 (t, 2H, J=6.8 Hz), 3.46-3.53 (m, 1H), 3.36-3.44 (m, 1H), 2.10-2.22 (m, 4H), 1.20-1.80 (m, 26H).

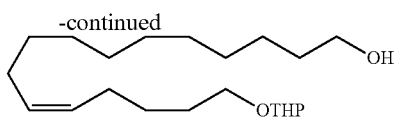

Semi-hydrogenation of 16-(tetrahydro-2H-pyran-2-yloxy)hexadec-11-yn-1-ol as described above gave 16-(tetrahydro-2H-pyran-2-yloxy)hexadec-11(Z)-en-1-ol (99%) as a colorless oil. TLC: 20% EtOAc/hexane, $R_f$=0.30; $^1$H NMR (CDCl$_3$, 300 MHz) δ 5.33-5.37 (m, 2H), 4.58 (m, 1H), 3.83-3.90 (m, 1H), 3.73-3.77 (m, 1H), 3.65 (t, 2H, J=6.7 Hz), 3.46-3.53 (m, 1H), 3.34-3.44 (m, 1H), 1.97-2.09 (m, 4H), 1.20-1.83 (m, 26H).

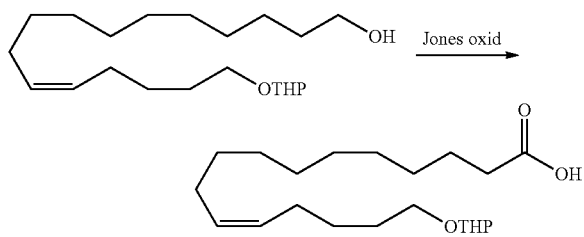

Jones oxidation of 16-(tetrahydro-2H-pyran-2-yloxy)hexadec-11(Z)-en-1-ol as described above gave 16-(tetrahydro-2H-pyran-2-yloxy)hexadec-11(Z)-enoic acid (68%) as a colorless oil. TLC: SiO$_2$, 40% EtOAc/hexanes, $R_f$=0.40; $^1$H NMR (CDCl$_3$, 300 MHz) δ 5.33-5.37 (m, 2H), 4.56-4.58 (m, 1H), 3.83-3.88 (m, 1H), 3.73-3.78 (m, 1H), 3.49-3.53 (m, 1H), 3.35-3.43 (m, 1H), 2.34 (t, J=7.0 Hz, 2H) 1.97-2.09 (m, 4H), 1.20-1.84 (m, 24H).

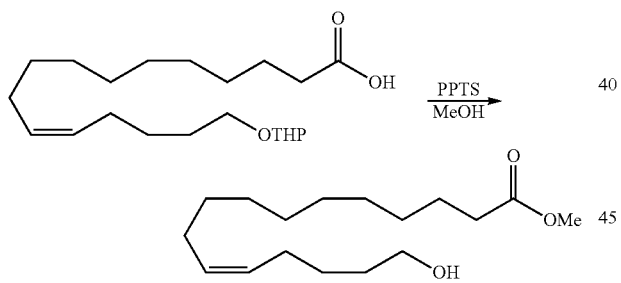

A solution of 16-(tetrahydro-2H-pyran-2-yloxy)hexadec-11(Z)-enoic acid (2.1 g, 5.93 mmol) and PTSA (50 mg) in MeOH (30 mL) was stirred at room temperature for 10 h, then concentrated in vacuo and the residue was purified by SiO$_2$ column chromatography using 15% EtOAc/hexanes as eluent to give methyl 16-hydroxyhexadec-11(Z)-enoate (1.42 g, 83%) as a colorless oil. TLC: 20% EtOAc/hexanes, $R_f$=0.35; $^1$H NMR (CDCl$_3$, 300 MHz) δ 5.33-5.37 (m, 2H), 3.65 (s, 3H), 3.63 (t, J=7.3 Hz, 2H), 2.29 (t, J=7.0 Hz, 2H), 1.97-2.08 (m, 4H), 1.21-1.64 (m, 18H).

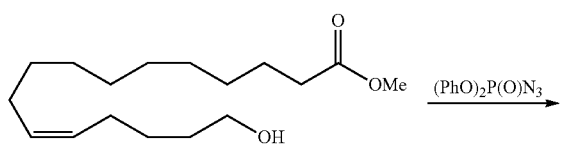

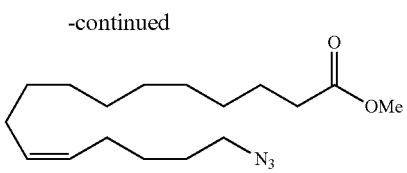

Diisopropyl azodicaboxylate (DIAD; 1.15 g, 5.70 mmol,) was added dropwise to a −20° C. solution of triphenylphosphine (1.49 g, 5.70 mmol) in dry THF (30 mL) under an argon atmosphere. After stirring for 10 min, a solution of methyl 16-hydroxyhexadec-11(Z)-enoate (1.35 g, 4.75 mmol) in anhydrous THF (5 mL) was added dropwise. After 30 min at −20° C., the reaction mixture was warmed to 0° C. and diphenylphosphoryl azide (DPPA, 1.38 g, 5.70 mmol) was added dropwise. After stirring at room temperature for 6 h, the reaction was quenched with water (3 mL), diluted with ether (50 mL), and washed with brine (40 mL). The aqueous layer was back-extracted with ether (2×30 mL). The combined organic extracts were dried over Na$_2$SO$_4$, and concentrated under reduced pressure. The residue was purified by SiO$_2$ column chromatography using 5% EtOAc/hexanes as eluent to afford methyl 16-azidohexadec-11(Z)-enoate (1.14 g, 78%) as a light yellow oil (contaminated with a little DIAD impurity). TLC: 10% EtOAc/hexanes, $R_f$=0.45; $^1$H NMR (CDCl$_3$, 300 MHz) δ 5.31-5.43 (m, 2H), 3.66 (s, 3H), 3.26 (t, J=6.7 Hz, 2H), 2.30 (t, J=7.1 Hz, 2H), 1.97-2.10 (m, 4H), 1.50-1.64 (m, 4H), 1.15-1.48 (m, 14H). Lit. ref.: C. M. Afonso; M. T. Barros; L. S. Godinhoa; C. D. Maycock *Tetrahedron* 1994: 50, 9671.

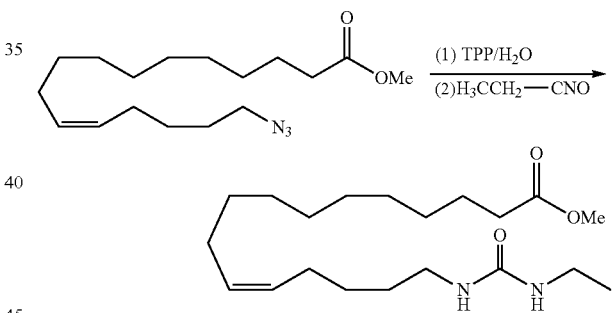

Triphenylphosphine (1.15 g., 4.41 mmol) was added to a room temperature solution of methyl 16-azidohexadec-11(Z)-enoate (1.05 g., 3.4 mmol) in THF (25 mL). After 2 h, water (200 □L) was added and the stirring was continued for another 8 h. The reaction mixture was then diluted with EtOAc (20 mL), washed with water (20 mL) and brine (25 mL). Aqueous layers were back-extracted with EtOAc (2×30 mL). The combined organic extracts were dried over Na$_2$SO$_4$, concentrated under reduced pressure and further dried under high vacuum for 4 h. The crude methyl 16-aminohexadec-11(Z)-enoate was used in the next step without additional purification. Lit. ref.: S. Chandrasekhar; S. S. Sultana; N. Kiranmai; Ch. Narsihmulu *Tetrahedron Lett.* 2007: 48, 2373.

Ethyl isocyanate (60 mg, 0.85 mmol) was added to a room temperature solution of the above crude methyl 16-aminohexadec-11(Z)-enoate (200 mg. 0.71 mmol) in dry THF (20 mL). After 6 h, reaction mixture was concentrated under reduced pressure and the residue was purified by SiO$_2$ column chromatography using 30% EtOAc/hexanes as eluent to give methyl 16-(3-ethylureido)hexadec-11(Z)-enoate (223 mg, 86%) as a colorless, thick oil. TLC: 50% EtOAc/hexanes, $R_f$=0.40; $^1$H NMR (CDCl$_3$, 300 MHz) δ 5.23-5.38 (m, 2H), 5.08 (br s, 2H), 3.63 (s, 3H), 3.09-3.20 (m, 4H), 2.27 (t, J=7.1 Hz, 2H), 1.93-2.04 (m, 4H), 1.20-1.62 (m, 18H), 1.08 (t, J=7.3 Hz, 3H); $^{13}$C NMR (CDCl$_3$, 75 MHz) δ 174.72, 130.53, 129.45, 51.70, 40.47, 35.26, 34.32, 30.24, 29.91, 29.66, 29.60, 29.46, 29.34, 27.43, 27.27, 27.12, 25.15, 15.80. Lit. ref.: V. Papesch; E. F. Schroeded *J. Org. Chem.* 1951: 16, 1879.

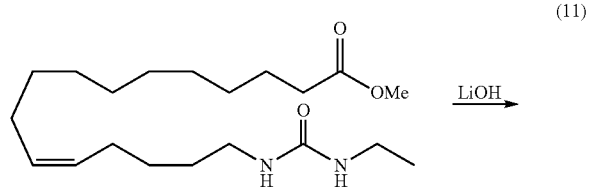

(11)

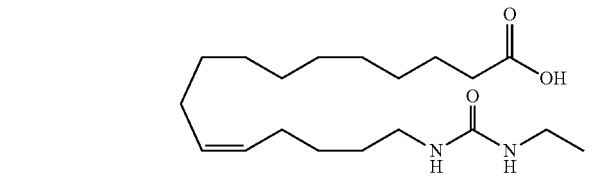

Methyl 16-(3-ethylureido)hexadec-11(Z)-enoate was hydrolyzed as described above to give 16-(3-ethylureido)hexadec-11(Z)-enoic acid (82%) obtained as a white powder. M.P.: 83.1-83.3° C. TLC: SiO$_2$, 75% EtOAc/hexanes, $R_f$=0.3; $^1$H NMR (CDCl$_3$, 300 MHz) δ 5.26-5.42 (m, 2H), 4.89 (br s, 1H), 3.06-3.24 (m, 4H), 2.32 (t, J=7.1 Hz, 2H), 1.97-2.08 (m, 4H), 1.22-1.64 (m, 18H), 1.14 (t, J=7.3 Hz, 3H); $^{13}$C NMR (CDCl$_3$, 75 MHz) δ 179.72, 130.79, 129.35, 40.99, 35.66, 34.45, 29.70, 29.67, 29.24, 29.12, 28.99, 27.26, 27.14, 27.04, 24.97, 15.50.

Example 7

Synthesis of 16-(Butyrylamino)hexadec-11(Z)-enoic acid (12)

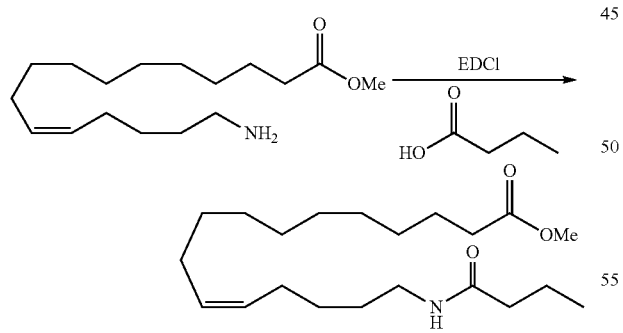

Butyric acid (100 mg, 1.10 mmol), 1-hydroxybenzotriazole (145 mg, 1.10 mmol; HOBt) and diisopropylethylamine (150 mg, 1.10 mmol; DIPEA) were added to a stirring solution of the previously described crude methyl 16-aminohexadec-11(Z)-enoate (240 mg, 0.85 mmol) in anhydrous DMF (20 mL) under an argon atmosphere. After 5 min, 1-ethyl-3-(3-dimethylaminopropyl)carbodiimide (210 mg, 1.10 mmol; EDCI) was added as a solid. After stirring for 12 h at room temperature, the reaction mixture was diluted with EtOAc (30 mL), washed with water (30 mL), and brine (20 mL). The combined aqueous layers were back-extracted with EtOAc (3×30 mL). The combined organic extracts were dried over Na$_2$SO$_4$, concentrated under reduced pressure, and the residue was purified by SiO$_2$ column chromatography using 30% EtOAc/hexanes as eluent to give methyl 16-(butyrylamino)hexadec-11(Z)-enoate (246 mg, 82%) as a viscous oil. TLC: 50% EtOAc/hexanes, $R_f$=0.5; $^1$H NMR (CDCl$_3$, 300 MHz) δ 5.58 (br s, 1H), 5.26-5.40 (m, 2H), 3.65 (s, 3H), 3.19-3.26 (m, 2H), 2.25-2.31 (m, 2H), 2.12 (t, J=7.1 Hz, 2H), 1.95-2.08 (m, 4H), 1.22-1.66 (m, 18H), 0.92 (t, J=7.1 Hz, 3H); $^{13}$C NMR (CDCl$_3$, 75 MHz) δ 174.61, 173.26, 130.71, 129.31, 51.67, 39.60, 38.99, 34.32, 29.90, 29.66, 29.60, 29.50, 29.45, 29.34, 27.43, 27.21, 27.01, 25.15, 19.46, 13.98. Lit. ref.: J. Cesar; M. S. Dolenc *Tetrahedron Lett.* 2001, 42, 7099.

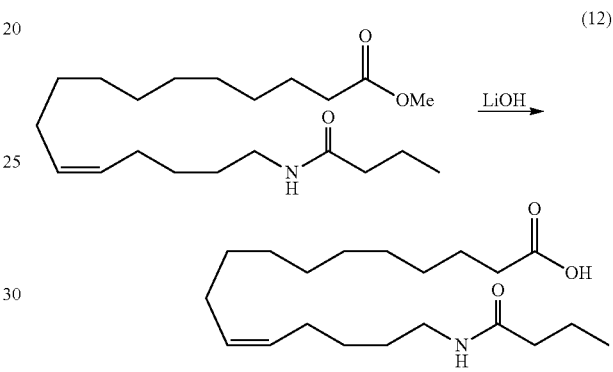

(12)

Methyl 16-(butyrylamino)hexadec-11(Z)-enoate was hydrolyzed as described above to give 16-(butyrylamino)hexadec-11(Z)-enoic acid (88%) as a white solid. M.P. 99.2-99.6° C. TLC: 75% EtOAc/hexanes, $R_f$=0.5; $^1$H NMR (CD$_3$OD, 300 MHz) δ 5.28-5.41 (m, 2H), 3.15 (t, 2H, J=7.3 Hz), 2.01-2.21 (m, 8H), 1.22-1.64 (m, 20H), 0.93 (t, 3H, J=7.1 Hz); $^{13}$C NMR (CDCl$_3$, 75 MHz) δ 174.89, 130.10, 129.17, 39.07, 37.88, 29.67, 29.55, 29.49, 29.20, 28.89, 27.00, 26.95, 26.66, 26.52, 22.96, 19.31, 12.85.

Example 8

Synthesis of 16-(2-(methylamino)-2-oxoacetamido)hexadec-11(Z)-enoic acid (13)

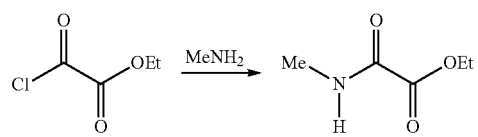 [SMILES: "MeNH2" ; CCOC(=O)C(=O)Cl ; CCOC(=O)C(=O)NC]

Methylamine (1.5 g, 23 mL of a 1 M THF solution, 48.38 mmol) solution was added dropwise to a −10° C. solution of ethyl chlorooxoacetate (5.0 g, 36.76 mmol) and triethylamine (5.6 g, 7.6 mL, 55.44 mmol) in dry THF (100 mL) under an argon atmosphere. After stirring at 0° C. for 1 h, then reaction was quenched with water (5 mL). Following another 20 min, the reaction mixture was extracted into ethyl acetate (2×30 mL) and the combined organic extracts were washed with water (2×100 mL), dried and concentrated in vacuo. The residue was purified by column chromatography using 40% EtOAc/hexanes to give monoethyl N-methyloxalamic acid (3.95 g, 82%) as a white powder. TLC: 75% EtOAc/hexane, $R_f$≈0.4; $^1$H NMR (CDCl$_3$, 300 MHz) δ 4.35 (q, 2H, J=7.0 Hz), 2.92 (d, 3H, J=5.2 Hz), 1.37 (t, 3H, J=7.3 Hz).

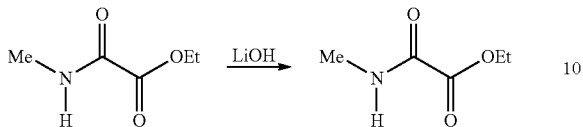

The obtained mass (2 g, 15.26 mmol) was subjected to hydolize in the presence of lithium hydroxide (2.0 M) solution in aqueous tetrahydrofuran. After completion of the reaction (as per TLC), the whole mass was acidify with 1N HCl (15 mL) to bring $P^H$=1 and then diluted with ethyl acetate (50 mL) and washed with water (50 mL). The aqueou layer was back extracted with ethyl acetate (3×40 mL). The combined organic layer was dried over Na$_2$SO$_4$ and concentrated under reduced pressure and the obtained mass was washed with hexanes/ether (1/1) to give white solid which was used for next reaction without further purification.

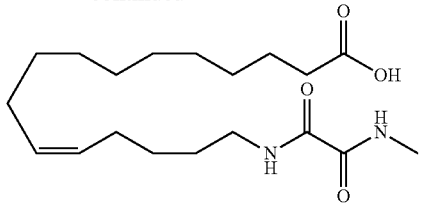

Methyl 16-aminohexadec-11(Z)-enoate (180 mg, 0.64 mmol) was condensed with 2-(methylamino)-2-oxoacetic acid (mg, 0.77 mmol) as described above to give methyl 16-(2-(methylamino)-2-oxoacetamido)hexadec-11(Z)-enoate (160 mg, 68%) as a white solid. TLC: 100% EtOAc, $R_f$≈0.4; $^1$H NMR (CDCl$_3$, 300 MHz) δ 7.45 (br s, 1H), 5.26-5.42 (m, 2H), 3.66 (s, 3H), 3.27-3.35 (m, 2H), 2.90 (d, 3H, J=5.2 Hz), 2.30 (t, 2H, J=7.3 Hz), 1.96-2.08 (m, 4H), 1.24-1.66 (m, 18H); $^{13}$C NMR (CDCl$_3$, 75 MHz) δ 174.60, 160.81, 159.94, 130.87, 129.08, 51.68, 39.79, 34.33, 29.91, 29.68, 29.63, 29.50, 29.46, 29.36, 29.02, 27.46, 27.08, 26.91, 26.40, 25.17.

(13)

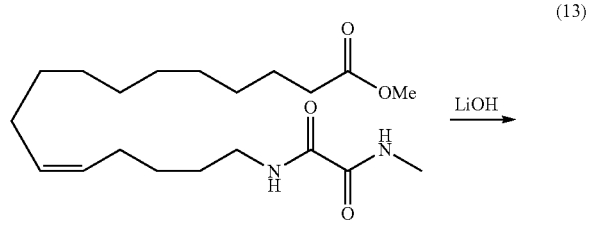

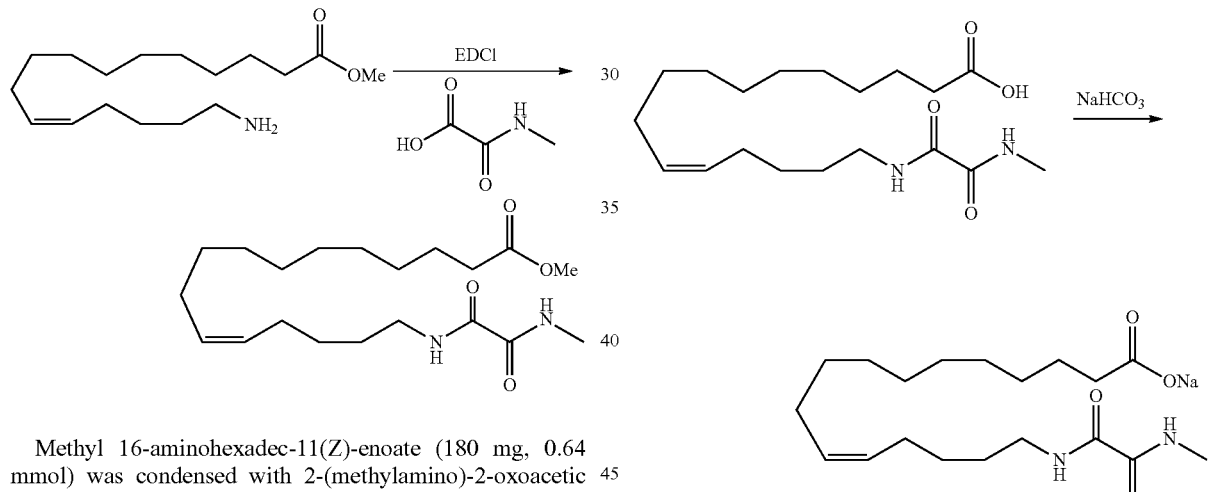

Methyl 16-(2-(methylamino)-2-oxoacetamido)hexadec-11(Z)-enoate (150 mg, 0.40 mmol) was hydrolyzed using LiOH as described above to afford 16-(2-(methylamino)-2-oxoacetamido)hexadec-11(Z)-enoic acid (126 mg, 89%) as a white powder. M.P.: 110.2-110.6° C. TLC: 5% MeOH/CH$_2$Cl$_2$, $R_f$≈0.4; $^1$H NMR (CDCl$_3$, 300 MHz) δ 7.80 (br s, 1H), 7.66 (br s, 1H), 5.26-5.42 (m, 2H), 3.28-3.35 (m, 2H), 2.90 (s, 3H), 2.36 (t, 2H, J=7.3 Hz), 1.97-2.08 (m, 4H), 1.51-1.64 (m, 4H), 1.22-1.42 (m, 14H); $^{13}$C NMR (CDCl$_3$, 75 MHz) δ 177.98, 160.96, 159.93, 130.83, 129.22, 39.91, 33.91, 29.58, 29.25, 29.12, 29.01, 28.95, 27.21, 27.09, 26.93, 26.46, 24.89.

16-(2-(Methylamino)-2-oxoacetamido)hexadec-11(Z)-enoic acid (30 mg) was dissolved in deionized water (30 mL) and NaHCO$_3$ (2 g., 10 equiv) was added with stirring. After 1 h at room temperature, pre-washed Bio-Rad® Bio-Beads (SM-2, 20-50 mesh, 15 g) were added. After gently stirring for 1 h, the beads were collected on a sintered glass funnel and washed with water (150 mL), and then the salt was stripped from the beads by washing with 99% ethanol (200 mL). The ethanol washings were concentrated under reduced pressure to give sodium 16-(2-(Methylamino)-2-oxoacetamido)hexadec-11(Z)-enoate as a white amorphous solid. $^1$H NMR (CD$_3$OD, 300 MHz) δ 7.52-7.64 (m, 2H), 5.27-5.38 (m, 2H), 3.27 (t, 2H, J=7.4 Hz), 2.82 (s, 3H), 2.25 (t, 2H, J=7.5 Hz), 1.97-2.05 (m, 4H), 1.52-1.65 (m, 4H), 1.20-1.41 (m, 14H);

Example 9

Synthesis of 16-(N-Isopropylbutyramido)hexadec-11(Z)-enoic acid (15)

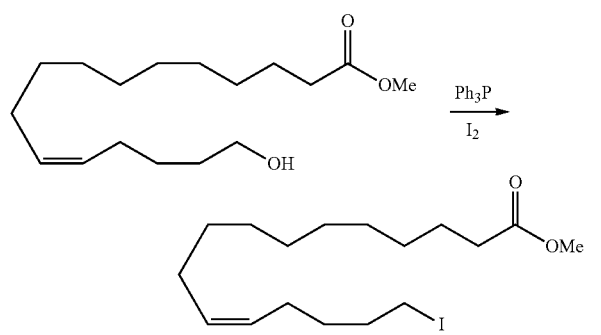

Triphenylphosphine (730 mg, 2.78 mmol) and imidazole (190 mg, 2.78 mmol) were added to a 0° C. solution of methyl 16-hydroxyhexadec-11(Z)-enoate (660 mg, 2.32 mmol) in dry THF (50 mL) under an argon atmosphere. After 10 min, solid iodine (700 mg, 1.2 equiv) was added portionwise. After stirring at room temperature for 3 h, the reaction mixture was quenched with sat. aq. sodium bisulfite solution (10 mL). After an additional 1 h, the solution was washed with water (2×30 mL), concentrated under reduced pressure, and the residue was purified by flash column chromatography using 10% EtOAc/hexanes as eluent to give methyl 16-iodohexadec-11(Z)-enoate (505 mg, 76%). TLC: 10% EtOAc/hexanes, $R_f$≈0.55; $^1$H NMR (CDCl$_3$, 300 MHz) δ 5.28-5.42 (m, 2H), 3.66 (s, 3H), 3.18 (t, J=7.0 Hz, 2H), 2.30 (t, J=7.6 Hz, 2H), 1.98-2.08 (m, 4H), 1.24-1.85 (m, 18H).

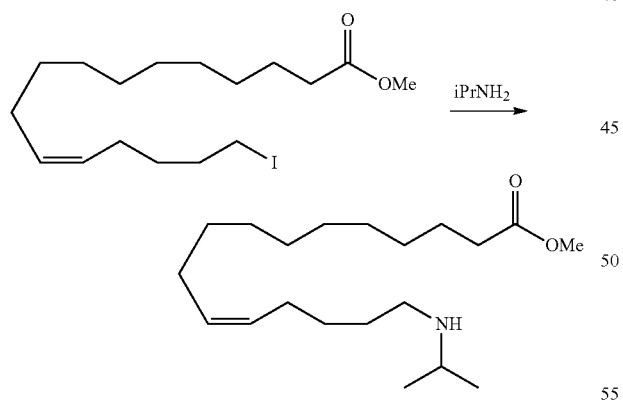

Isopropylamine (220 mg, 3.8 mmol) was added to a solution of methyl 16-iodohexadec-11(Z)-enoate (300 mg, 0.76 mmol) from above and potassium carbonate (320 mg) in THF (20 mL) under an argon atmosphere in a sealed tube. After heating at 90° C. for h, the reaction mixture was cooled to room temperature, diluted with EtOAc (50 mL), washed with water (20 mL), dried, and concentrated under high vacuum for 5 h. The crude methyl 16-(N-isopropylamino)hexadec-11(Z)-enoate was used in the next reaction without further purification. TLC: 20% MeOH/CH$_2$Cl$_2$, $R_f$≈0.20; $^1$H NMR (CDCl$_3$, 300 MHz) δ 5.28-5.40 (m, 2H), 3.66 (s, 3H), 2.72-2.84 (m, 1H), 2.58 (t, J=7.2 Hz, 2H), 2.29 (t, J=7.6 Hz, 2H), 1.98-2.08 (m, 4H), 1.22-1.62 (m, 18H), 1.05 (d, 6H, J=6.4 Hz).

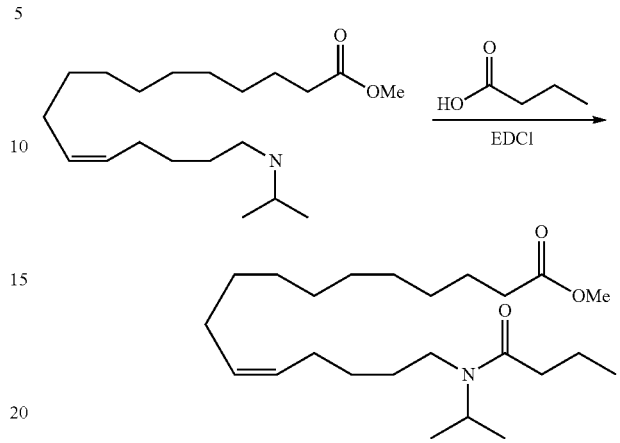

Methyl 16-(N-isopropylamino)hexadec-11(Z)-enoate (400 mg, 1.2 mmol) was acylated with n-butyric acid (130 mg, 1.47 mmol) as described above to give methyl 16-(N-isopropylbutyramido)hexadec-11(Z)-enoate (348 mg, 74%). TLC: 50% EtOAc/hexanes, $R_f$≈0.30; $^1$H NMR (CDCl$_3$, 300 MHz, rotamers) δ 5.28-5.42 (m, 2H), 4.61-4.67 and 3.99-4.10 (m, 1H for two rotamers 60/40 ratio), 3.66 (s, 3H), 3.06-3.16 (m, 2H), 2.21-2.36 (m, 4H), 1.95-2.10 (m, 4H), 1.20-1.72 (m, 20H), 1.17 and 1.12 (d, J=6.6 Hz, 3H for two rotamers in 60/40 ratio), 0.96 and 0.95 (t, 3H, J=7.3 Hz for two rotamers in 60/40 ratio).

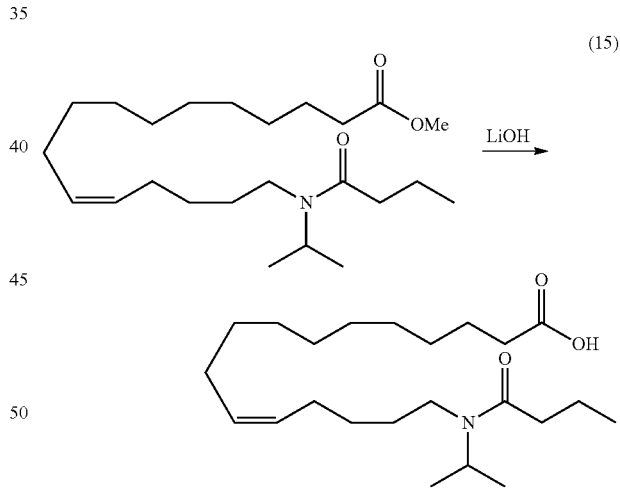

Methyl 16-(N-isopropylbutyramido)hexadec-11(Z)-enoate (320 mg, 0.81 mmol) was hydrolyzed as described above to give 16-(N-isopropylbutyramido)hexadec-11(Z)-enoic acid (254 mg, 83%) as a thick, colorless oil. TLC: 75% EtOAc/hexanes, $R_f$≈0.40; $^1$H NMR (CDCl$_3$, 300 MHz, rotamers) δ 5.26-5.41 (m, 2H), 4.63-4.69 and 4.00-4.10 (m, 1H for two rotamers in 60/40 ratio), 3.06-3.17 (m, 2H), 2.22-2.37 (m, 4H), 1.98-2.12 (m, 4H), 1.50-1.72 (m, 4H), 1.22-1.40 (m, 16H), 1.18 and 1.12 (d, J=7.0 Hz, 6H for two rotamers in 60/40 ratio), 0.96 and 0.95 (t, J=7.3 Hz, 3H for two rotamers in 60/40 ratio); $^{13}$C NMR (CDCl$_3$, 75 MHz, rotamers) δ 179.07, 178.95, 173.42, 172.89, 131.03, 130.35, 129.70, 128.99, 48.51, 45.70, 43.58, 41.22, 35.98, 35.83, 34.37, 31.20, 29.90, 29.86, 29.67, 29.61, 29.53, 29.48, 29.39, 28.37, 29.28, 27.84, 27.50, 27.46, 27.35, 27.19, 26.90, 25.00, 21.54, 20.75, 19.35, 19.22, 14.23; MS: m/z 380 (M-H)+.

Example 10

Synthesis of Methyl 16-(3-ethyl-1,3-dimethylureido)hexadec-11(Z)-enoic Acid (16)

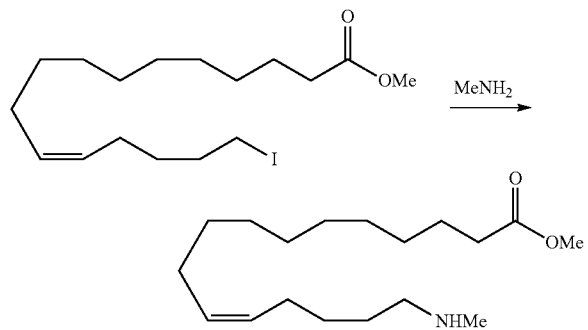

Methylamine (1 mL of a 1.0 M THF soln, 33 mg) was added to a solution of methyl 16-iodohexadec-11(Z)-enoate (300 mg, 0.76 mmol) from above and potassium carbonate (320 mg, 2.28 mmol, 3 equiv) in THF (20 mL) under an argon atmosphere in a sealed tube. After heating at 90° C. for 12 h, the reaction mixture was cooled to room temperature, diluted with EtOAc (50 mL), washed with water (20 mL), dried, and concentrated under high vacuum for 5 h. The crude methyl 16-(methylamino)hexadec-11(Z)-enoate was used in the next reaction without further purification. TLC: 10% MeOH/CH$_2$Cl$_2$, R$_f$=0.2; $^1$H NMR (CDCl$_3$, 300 MHz) δ 5.28-5.40 (m, 2H), 3.66 (s, 3H), 2.56 (t, J=6.8 Hz, 2H), 2.42 (s, 3H), 2.29 (t, J=7.6 Hz, 2H), 1.96-2.06 (m, 4H), 1.24-1.64 (m, 18H)

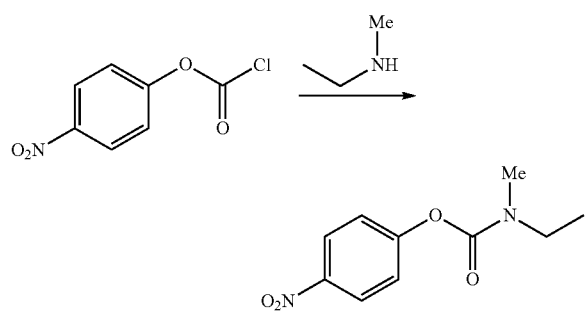

Triethylamine (12.84 g, 127.11 mmol) and p-nitrophenyl chloroformate (63.56 mmol, 12.8 g) were added to a room temperature solution of N-ethylmethylamine (2.50 g, 42.37 mmol) in dry DMF (70 mL) under an argon atmosphere. After 2 h, the reaction mixture was quenched with water, diluted with EtOAc (200 mL), washed with water (2×100 mL), and brine (75 mL). All volatiles were removed under reduced pressure and the residue was purified by SiO$_2$ column chromatography using 10% EtOAc/hexanes to afford compound 4-nitrophenyl ethyl(methyl)carbamate (5.8 g, 76%) as a yellow oil. TLC: 20% EtOAc/hexanes, R$_f$=0.50; $^1$H NMR (CDCl$_3$, 300 MHz) δ 8.18-8.21 (m, 2H), 7.25-7.29 (m, 2H), 3.37-3.46 (m, 2H), 3.05 and 2.97 (s, 3H for two rotamers in 60/40 ratio), 1.17-1.22 (m, 3H).

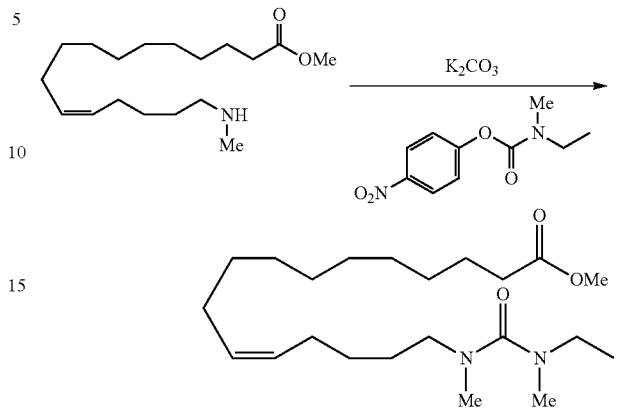

A solution of crude methyl 16-(methylamino)hexadec-11(Z)-enoate from above (150 mg, 0.51 mmol) in anhydrous acetonitrile (20 mL) was added to a mixture of p-nitrophenyl chloroformate (130 mg, 0.72 mmol) and K$_2$CO$_3$ (230 mg, 1.5 mmol.) in dry acetonitrile (20 mL) at room temperature. After heating under reflux for 36 h, the solvent was removed under reduced pressure and the residue was diluted with water (30 mL) and then extracted into EtOAc (2×30 mL). The combined organic extracts were dried over Na$_2$SO$_4$ and concentrated under reduced pressure. The residue was purified by SiO$_2$ column chromatography using 15% EtOAc/hexanes as eluent to afford methyl 16-(3-ethyl-1,3-dimethylureido)hexadec-11(Z)-enoate (65 mg, 34%) as a colorless oil. TLC: 40% EtOAc/hexanes, R$_f$=0.40; $^1$H NMR (CDCl$_3$, 300 MHz) δ 5.27-5.40 (m, 2H), 3.66 (s, 3H), 3.10-3.18 (m, 4H), 2.77 (s, 3H), 2.75 (s, 3H), 2.29 (t, J=7.2 Hz, 2H), 1.97-2.05 (m, 4H), 1.50-1.68 (m, 4H), 1.20-1.42 (m, 14H), 1.12 (t, J=6.9 Hz, 3H).

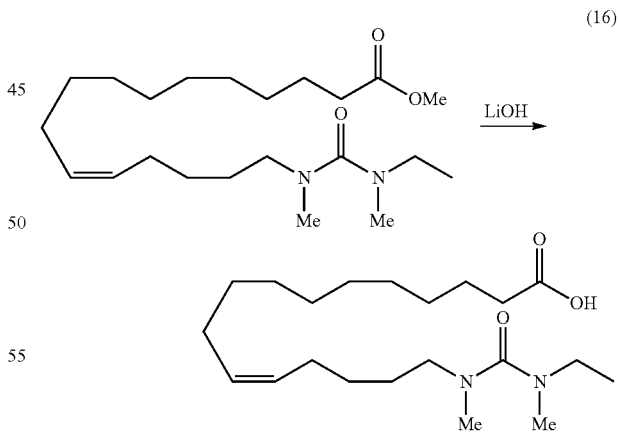

(16)

Methyl 16-(3-ethyl-1,3-dimethylureido)hexadec-11(Z)-enoate (30 mg, 0.08 mmol) was hydrolyzed as described above to give 16-(3-ethyl-1,3-dimethylureido)hexadec-11(Z)-enoic acid (15 mg, 75%) as colorless oil. TLC: 50% EtOAc/hexanes, R$_f$=0.30; $^1$H NMR (CDCl$_3$, 400 MHz) δ 5.33-5.41 (m, 2H), 3.12-3.19 (m, 4H), 2.79 (s, 3H), 2.76 (s, 3H), 2.31-2.38 (m, 2H), 1.98-2.06 (m, 4H), 1.20-1.68 (m, 18H), 1.13 (t, J=6.9 Hz, 3H); $^{13}$C NMR (CDCl$_3$, 75 MHz)

δ 177.52, 166.83, 130.61, 129.567, 51.58, 45.38, 37.91, 36.93, 34.12, 29.74, 29.67, 28.72, 28.42, 27.43, 26.68, 24.99, 22.64, 15.34.

Example 11

Synthesis of Sodium 17-Oxo-17-(propylamino)heptadec-11(Z)-enoate (14)

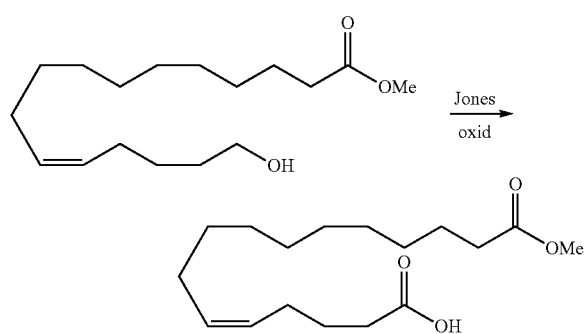

Jones oxidation of methyl 16-hydroxyhexadec-11(Z)-enoate (2.0 g, 7.04 mmol) as described above gave 16-methoxy-16-oxohexadec-5(Z)-enoic acid (1.72 g, 83%) as a colorless oil. TLC: 40% EtOAc/hexanes, $R_f$≈0.40; $^1$H NMR (CDCl$_3$, 300 MHz) δ 5.27-5.45 (m, 2H), 3.66 (s, 3H), 2.36 (t, 2H, J=7.7 Hz), 2.30 (t, 2H, J=7.4 Hz), 1.98-2.12 (m, 4H), 1.57-1.72 (m, 4H), 1.20-1.41 (m, 12H).

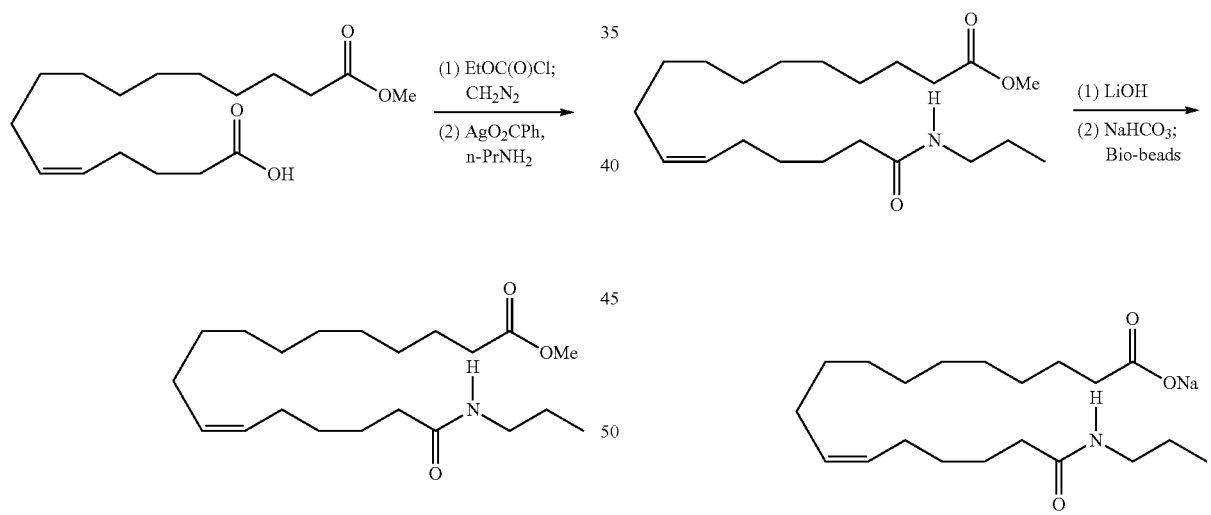

Triethylamine (122 mg, 1.18 mmol) and ethyl chloroformate (130 mg, 1.13 mmol) were added to a −15° C. solution of 16-methoxy-16-oxohexadec-5(Z)-enoic acid (300 mg, 1.06 mmol) in dry THF (50 mL) under an argon atmosphere. After 15 min, the reaction mixture was warmed to −5° C. and an ethereal solution of diazomethane was added slowly until the yellow color of diazomethane persisted for 15 min. Afterwards, the reaction mixture was stirred at room temperature for an additional 3 h, then the excess diazomethane was evaporated under a stream of argon. The reaction solution was washed with sat. aq. NaHCO$_3$ (50 mL), sat. aq. NH$_4$Cl (50 mL), brine (50 mL), dried over Na$_2$SO$_4$, and concentrated under reduced pressure. The residue was rapidly purified by SiO$_2$ column chromatography using 20% EtOAc/hexanes as eluent to give methyl 17-diazo-16-oxoheptadec-11(Z)-enoate (180 mg, 55%) as a light yellow oil that was used immediately in the next step. TLC: 40% EtOAc/hexanes, $R_f$≈0.40; $^1$H NMR (C$_6$D$_6$, 300 MHz) δ 5.25-5.48 (m, 2H), 4.13 (s, 1H), 3.32 (s, 3H), 2.07 (t, 2H, J=7.4 Hz), 1.85-2.04 (m, 6H), 1.44-1.61 (m, 4H), 1.15-1.38 (m, 12H). Lit. ref.: J. Cesar; M. S. Dolenc *Tetrahedron Lett.* 2001: 42, 7099.

A solution of silver benzoate (5 mg, 10 mol %) in triethylamine (68 mg, 100 μL, 0.66 mmol) was added to a −25° C. solution of methyl 17-diazo-16-oxoheptadec-11(Z)-enoate (70 mg, 0.22 mmol) and n-propylamine (40 mg, 10 equiv) in dry THF (20 mL) under an argon atmosphere with exclusion of light. The reaction mixture was warmed to room temperature over 3 h, diluted with ether (10 mL), quenched with 0.2 N HCl (5 mL), washed with brine (30 mL), sat. aq. NaHCO$_3$ (10 mL), dried over Na$_2$SO$_4$, and concentrated under reduced pressure. The residue was purified by SiO$_2$ column chromatography using 20% EtOAc/hexanes as eluent to give methyl 17-oxo-17-(propylamino)heptadec-11(Z)-enoate (49 mg, 64%) as a pale yellow oil. TLC: 30% EtOAc/hexanes, $R_f$≈0.40; $^1$H NMR (CDCl$_3$, 300 MHz) δ 5.47 (br s, 1H), 5.27-5.40 (m, 2H), 3.66 (s, 3H), 3.17-3.24 (m, 2H), 2.29 (t, 2H, J=7.1 Hz), 2.16 (t, 2H, J=7.1 Hz), 1.96-2.07 (m, 4H), 1.24-1.67 (m, 20H), 0.91 (t, 3H, J=7.3 Hz); $^{13}$C NMR (CDCl$_3$, 75 MHz) δ 174.62, 173.22, 130.59, 129.41, 51.68, 41.40, 37.05, 34.33, 29.93, 29.67, 29.63, 29.48, 29.36, 27.44, 27.16, 25.73, 25.17, 23.14, 11.60. Lit. ref.: J. Podlech; D. Seebach *Angew. Chem., Int. Ed.* 1995: 34, 471.

Methyl 17-oxo-17-(propylamino)heptadec-11(Z)-enoate (48 mg, 0.14 mmol) was converted to its sodium salt as described above to give sodium 17-oxo-17-(propylamino) heptadec-11(Z)-enoate as a white solid. M.P.: 84.8-85.2° C. TLC (free acid): 75% EtOAc/hexanes, $R_f$≈0.30; $^1$H NMR for sodium salt salt (CD$_3$OD, 300 MHz) δ 5.30-5.42 (m, 2H), 3.16 (t, 2H, J=7.0 Hz), 2.00-2.22 (m, 8H), 1.22-1.68 (m, 20H), 0.93 (t, 3H, J=7.2 Hz); $^{13}$C NMR for sodium salt (CD$_3$OD, 75 MHz) δ 180.33, 174.88, 130.08, 129.22, 39.07, 37.88, 36.80, 29.70, 29.53, 29.49, 29.45, 29.21, 28.90, 27.02, 26.96, 26.68, 26.12, 19.32, 12.88.

Example 12

Synthesis of 16-(Butylamino)-16-oxohexadec-11(Z)-enoic acid (24)

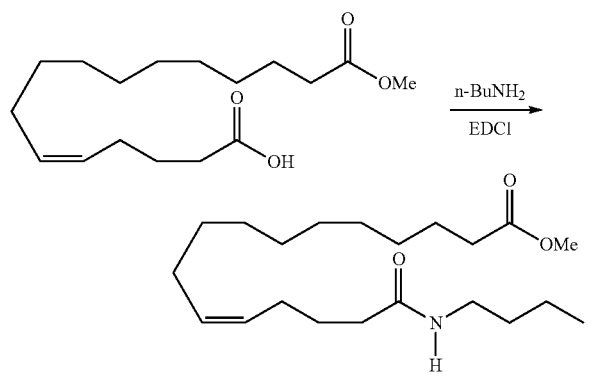

16-Methoxy-16-oxohexadec-5(Z)-enoic acid (230 mg, 0.77 mmol) was condensed with n-butylamine (70 mg, 1.08 mmol) using EDCI as described to give methyl 16-(butylamino)-16-oxohexadec-11(Z)-enoate (185 mg, 68%) as a colorless oil. TLC: 50% EtOAc/hexanes, $R_f$=0.40; $^1$H NMR (CDCl$_3$, 300 MHz) δ 5.26-5.42 (m, 2H), 3.66 (s, 3H), 3.21-3.29 (m, 2H), 2.30 (t, 2H, J=7.2 Hz), 2.16 (t, 2H, J=7.1 Hz), 1.97-2.08 (m, 4H), 1.55-1.74 (m, 4H), 1.24-1.54 (m, 14H), 0.92 (t, 3H, J=7.3 Hz); $^{13}$C NMR (CDCl$_3$, 75 MHz) δ 174.60, 173.1, 131.18, 128.83, 51.67, 39.42, 36.44, 34.32, 31.98, 29.91, 29.66, 29.60, 29.49, 29.45, 29.34, 27.47, 26.87, 25.95, 25.15, 20.30, 13.98.

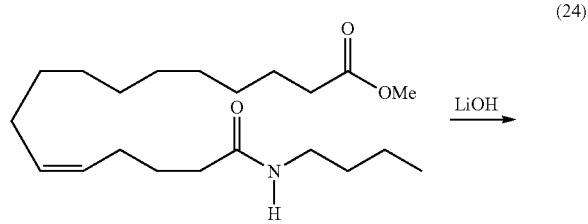

(24)

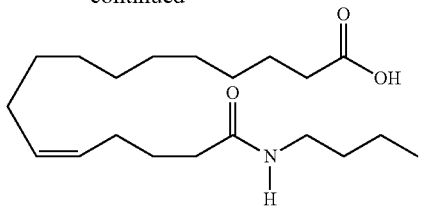

Methyl 16-(butylamino)-16-oxohexadec-11(Z)-enoate (150 mg, 0.44 mmol) was hydrolyzed to give 16-(butylamino)-16-oxohexadec-11(Z)-enoic acid (114 mg, 82%) as a white solid. M.P.: 78.2-78.8° C. TLC: 75% EtOAc/hexanes, $R_f$=0.3; $^1$H NMR (CDCl$_3$, 300 MHz) δ 5.81 (br s, 1H), 5.24-5.40 (m, 2H), 3.18-3.24 (m, 2H), 2.30 (t, 2H, J=7.3 Hz), 2.16 (t, 2H, J=7.2 Hz), 1.93-2.06 (m, 4H), 1.19-1.70 (m, 20H), 0.88 (t, 3H, J=7.4 Hz); $^{13}$C NMR (CDCl$_3$, 75 MHz) δ 178.98, 173.78, 131.19, 128.74, 39.54, 36.36, 34.37, 31.84, 29.84, 29.56, 29.53, 29.40, 29.38, 29.22, 27.42, 26.85, 25.99, 24.98, 20.26, 13.96.

Example 13

Synthesis of 2-(2-(2-Hydroxyethoxy)ethoxy)ethyl 16-(3-ethylureido)hexadec-11(Z)-enoate (18)

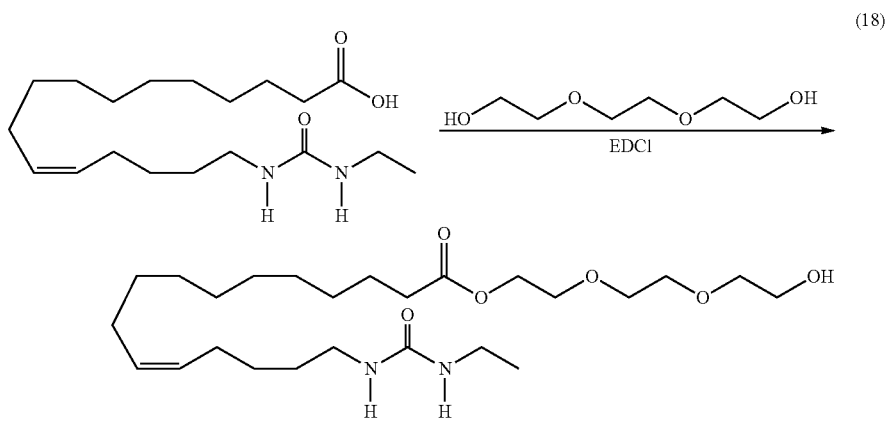

(18)

Triethyleneglycol (42 mg, 0.29 mmol; dried over molecular sieves) was added to a solution of 16-(3-ethyl-1,3-dimethylureido)hexadec-11(Z)-enoic acid (10 mg, 0.029 mmol) and N,N-dimethylaminopyridine (DMAP, 4.2 mg, 0.034 mmol) in anhydrous DMF (3 mL) under an argon atmosphere at room temperature. After 3 min, solid EDCI (6.4 mg, 0.034 mmol) was added. After 12 h, the reaction mixture was diluted with EtOAc (10 mL), washed with water (5 mL), and concentrated in vacuo. The residue was purified by SiO$_2$ column chromatography using EtOAc to give 2-(2-(2-Hydroxyethoxy)ethoxy)ethyl 16-(3-ethylureido)hexadec-11(Z)-enoate (11 mg, 85%) as a viscous, colorless oil. TLC: 100% EtOAc, $R_f$=0.20; $^1$H NMR (CDCl$_3$, 300 MHz) δ 5.27-5.42 (m, 2H), 4.34 (br s, 1H), 4.23 (t, 2H, J=5.8 Hz), 3.59-3.74 (m, 10H), 3.12-3.24 (m, 4H), 2.46 (br s, 1H), 2.33 (t, 2H, J=7.3 Hz), 1.96-2.07 (m, 4H), 1.22-1.64 (m, 18H), 1.13 (t, 3H, J=7.3 Hz); $^{13}$C NMR (CDCl$_3$, 75 MHz) δ 174.21, 158.42, 130.66, 129.44, 72.70, 70.79, 70.57, 69.44, 63.46, 61.98, 40.74, 35.59, 34.40, 30.11, 29.88, 29.63, 29.60, 29.44, 29.42, 29.31, 27.41, 27.22, 27.08, 25.10, 15.73.

Example 14

Synthesis of Sodium (Z)-2-(16-(3-Ethylureido)hexadec-11-enamido)acetate (17)

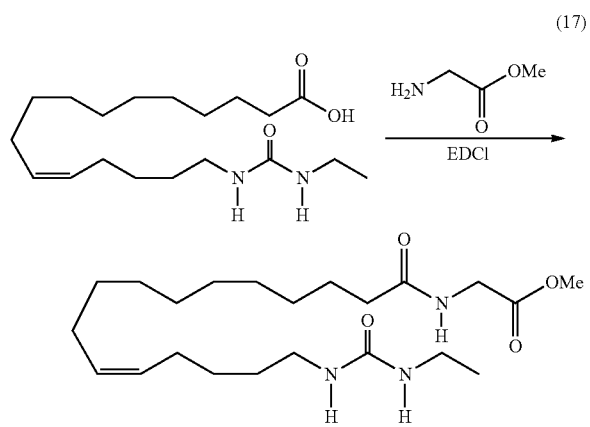

16-(3-Ethyl-1,3-dimethylureido)hexadec-11(Z)-enoic acid (50 mg, 0.15 mmol) was condensed with glycine methyl ester (96 mg, 0.38 mmol) as described above to give methyl 2-(16-(3-ethylureido)hexadec-11(Z)-enamido)acetate (51 mg, 84%) as a colorless oil. TLC: 75% EtOAc/hexanes, $R_f$=0.50; $^1$H NMR (CDCl$_3$, 300 MHz) δ 6.28 (br s, 1H), 5.26-5.42 (m, 2H), 4.89 (br s, 1H), 4.03 (d, 2H, J=5.2 Hz), 3.10-3.22 (m, 4H), 2.24 (t, 2H, J=7.1 Hz), 1.96-2.08 (m, 4H), 1.22-1.67 (m, 18H), 1.12 (t, 3H, J=7.3 Hz); $^{13}$C NMR (CDCl$_3$, 75 MHz) δ 173.84, 170.86, 158.68, 130.61, 129.50, 52.58, 41.40, 40.67, 36.58, 35.49, 30.18, 29.92, 29.73, 29.53, 29.46, 29.41, 29.22, 27.28, 27.25, 27.10, 25.78, 15.73.

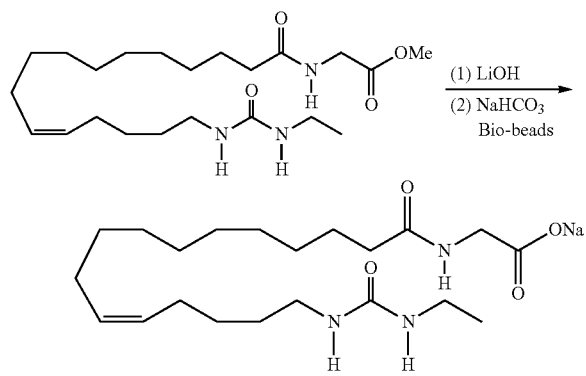

Methyl 2-(16-(3-ethylureido)hexadec-11(Z)-enamido)acetate was hydrolyzed as described above to give sodium 2-(16-(3-ethylureido)hexadec-11(Z)-enamido)acetate as a white solid. M.P.: 152.4-152.8° C. $^1$H NMR (CD$_3$OD, 300 MHz) δ 7.57-7.65 (m, 1H), 5.32-5.42 (m, 2H), 3.73 (s, 2H), 3.07-3.18 (m, 4H), 2.36 (t, 2H, J=7.3 Hz), 1.98-2.09 (m, 4H), 1.22-1.65 (m, 18H), 1.08 (t, 3H, J=7.1 Hz); $^{13}$C NMR (CDCl$_3$, 75 MHz) δ 175.41, 174.67, 160.72, 129.98, 129.31, 43.32, 39.70, 35.98, 34.58, 29.83, 29.66, 29.42, 29.31, 29.21, 29.14, 26.96, 26.91, 26.72, 25.70, 14.66.

Example 15

Synthesis of 16-[(1S,2R)-3-Ethyl-oxiranyl]hexadec-11(Z)-enoic acid (10)

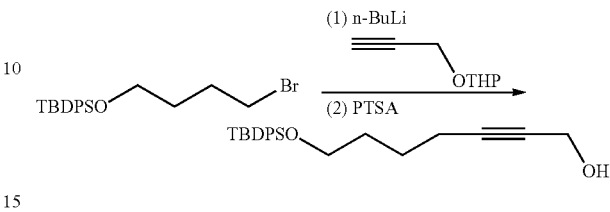

2-(Prop-2-ynyloxy)tetrahydro-2H-pyran (5.6 g, 36.36 mmol) was alkylated with (4-bromobutoxy)(tert-butyl)diphenylsilane (18.5 g, 47.2 mmol) as described above to give tert-butyldiphenyl(7-(tetrahydro-2H-pyran-2-yloxy)hept-5-ynyloxy)silane (10.64 g, 65%) and used after extractive isolation without further purification. TLC: 10% EtOAc/hexanes, $R_f$=0.5.

Removal of the THP ether from tert-butyldiphenyl(7-(tetrahydro-2H-pyran-2-yloxy)hept-5-ynyloxy)silane (10 g, 22.22 mmol) as described above furnished 7-(tert-butyldiphenylsilyloxy)hept-2-yn-1-ol (7.15 g, 88%) as a colorless oil. TLC: 30% EtOAc/hexanes, $R_f$=0.40; $^1$H NMR (CDCl$_3$, 300 MHz) δ 7.65-7.67 (m, 4H), 7.33-7.42 (m, 6H), 4.22-4.26 (m, 2H), 3.64 (t, 2H, J=6.4 Hz), 2.12-2.16 (m, 2H), 1.40-1.46 (m, 4H), 1.03 (s, 9H).

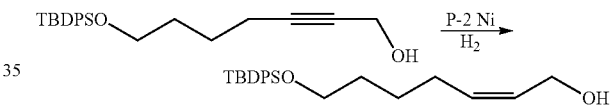

Semi-hydrogenation of 7-(tert-butyldiphenylsilyloxy)hept-2-yn-1-ol (7.4 g, 20.22 mmol) as described above furnished 7-(tert-butyldiphenylsilyloxy)hept-2(Z)-en-1-ol (7.3 g, 98%) as a colorless oil. TLC: 30% EtOAc/hexanes, $R_f$=0.5; $^1$H NMR (CDCl$_3$, 400 MHz) δ 7.65-7.69 (m, 4H), 7.40-7.44 (m, 6H), 5.44-5.64 (m, 2H), 4.16 (d, 2H, J=6.1 Hz), 3.65 (t, 2H, J=6.1 Hz), 2.03-2.10 (m, 2H), 1.42-1.60 (m, 4H), 1.04 (s, 9H).

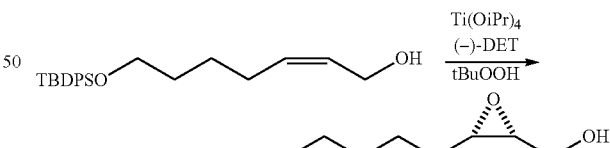

(−)-Diethyl tartrate (570 mg, DET) and titanium tetra (isopropoxide) (775 mg) were added sequentially to a stirring, −20° C. suspension of activated, powdered type 4 Å molecular sieves (2 g) in dry CH$_2$Cl$_2$ (50 mL) under an argon atmosphere. After 30 min, a solution of 7-(tert-butyldiphenylsilyloxy)hept-2(Z)-en-1-ol in (5 g, 13.58 mmol) dry CH$_2$Cl$_2$ (20 mL) was added slowly and the resulting mixture was stirred for 2 h at the same temperature. tert-butyl hydroperoxide (2.5 g, 5.1 mL of a 5.5 M solution in decane; TBHP) was added very slowly. After stirring at −20° C. for 2 d, water (2 mL) was added and the mixture was allowed to stir at 0° C. for 1 h. A solution of 1 M aq. NaOH (5 mL) was added and stirred for 30 min. The reaction mixture was then washed with water (100 mL) and concentrated under reduced pressure. Purification of the residue by SiO$_2$ column chromotography using 10% EtOAc/hexanes as eluent gave ((2R,3S)-3-(4-(tert-butyldiphenylsilyloxy)butyl)oxiran-2-yl)methanol (3.23 g, 62%) as a colorless oil. Chiral HPLC analysis as described above revealed the sample was 60% ee. TLC: 30% EtOAc/hexanes, R$_f$~0.4; $^1$H NMR (CDCl$_3$, 400 MHz) δ 7.64-7.68 (m, 4H), 7.35-7.44 (m, 6H), 3.79-3.88 (m, 1H), 3.61-3.69 (m, 3H), 3.12-3.17 (m, 1H), 2.98-3.04 (m, 1H), 1.53-1.65 (m, 4H), 1.03 (s, 9H). Lit. ref.: T. Katsuki; K. B. Sharpless *J. Am. Chem. Soc.* 1980: 102, 5974.

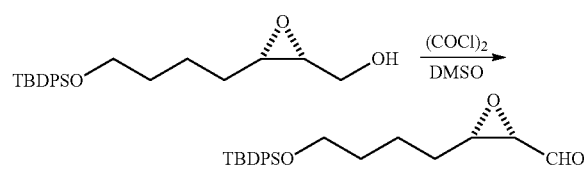

Dry DMSO (114 mg, 0.4 mmol) was added dropwise to a stirring, −80° C. solution of oxalyl chloride (110 mg, 0.3 mmol) in dry CH$_2$Cl$_2$ (10 mL) under an argon atmosphere. After 20 min, a solution of ((2R,3S)-3-(4-(tert-butyldiphenylsilyloxy)butyl)oxiran-2-yl)methanol (200 mg, 0.1 mmol) in dry CH$_2$Cl$_2$ (50 mL) was added slowly. After 45 min, triethylamine (200 mg, 0.5 mmol) was added and the reaction mixture was warmed to 0° C. After 0.5 h, the reaction mixture was quenched with water (50 mL). The aqueous layer was separated and back-extracted with CH$_2$Cl$_2$ (2×10 mL). The combined organic extracts were washed with water, brine, and dried over anhydrous Na$_2$SO$_4$, and evaporated in vacuo. The residue was purified via SiO$_2$ column chromatography using 5% EtOAc/hexanes to give (2S,3S)-3-[4-(tert-butyldiphenylsilanyloxy)-butyl]-oxirane-2-carbaldehyde. The crude aldehyde was used for the next reaction without further purification.

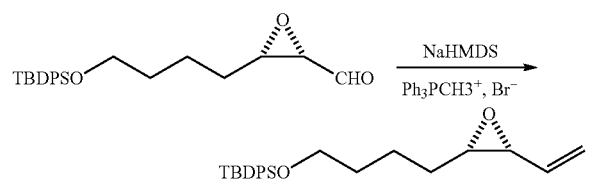

Sodium bis(trimethylsilyl)amide (2.4 g, 13.08 mmol, 13.1 mL, 1.0 M in THF) was added to a stirring, 0° C. solution of methyl triphenylphosphonium bromide (4.68 g, 13.08 mmol) in dry THF (10 mL). After 30 min, the reaction mixture was cooled to −50° C. and a solution of (2S,3S)-3-[4-(tert-butyldiphenylsilanyloxy)-butyl]-oxirane-2-carbaldehyde (2.5 g, 6.55 mmol) in THF (10 mL) was added over 5 min. The solution was warmed to room temperature over 1 h. After an additional 2 h at room temperature, the reaction mixture was quenched with water (30 mL) and extracted with ether (3×60 mL). The combined ethereal extracts were washed with water (2×100 mL), dried over anhydrous Na$_2$SO$_4$, and concentrated in vacuo. The residue was purified by SiO$_2$ column chromatography using 5% EtOAc/hexanes to give (3R,4S)-tert-butyldiphenyl-[4-(3-vinyl-oxiranyl)-butoxy]-silane (1.84 g, 76%) as a colorless oil. TLC: 30% EtOAc/hexanes, R$_f$~0.4; $^1$H NMR (CDCl$_3$, 400 MHz) δ 7.65-7.69 (m, 4H), 7.35-7.44 (m, 6H), 5.64-5.76 (m, 1H), 5.32-5.50 (m, 2H), 3.67 (t, 2H, J=7.06 Hz), 3.38-3.42 (m, 1H), 3.02-3.11 (m, 1H), 1.44-1.68 (m, 4H), 1.05 (s, 9H).

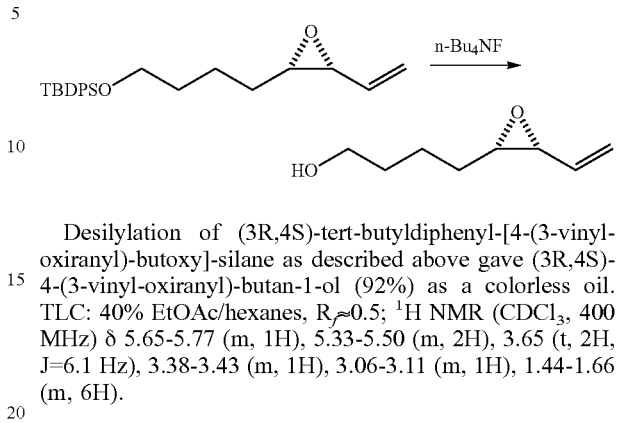

Desilylation of (3R,4S)-tert-butyldiphenyl-[4-(3-vinyloxiranyl)-butoxy]-silane as described above gave (3R,4S)-4-(3-vinyl-oxiranyl)-butan-1-ol (92%) as a colorless oil. TLC: 40% EtOAc/hexanes, R$_f$~0.5; $^1$H NMR (CDCl$_3$, 400 MHz) δ 5.65-5.77 (m, 1H), 5.33-5.50 (m, 2H), 3.65 (t, 2H, J=6.1 Hz), 3.38-3.43 (m, 1H), 3.06-3.11 (m, 1H), 1.44-1.66 (m, 6H).

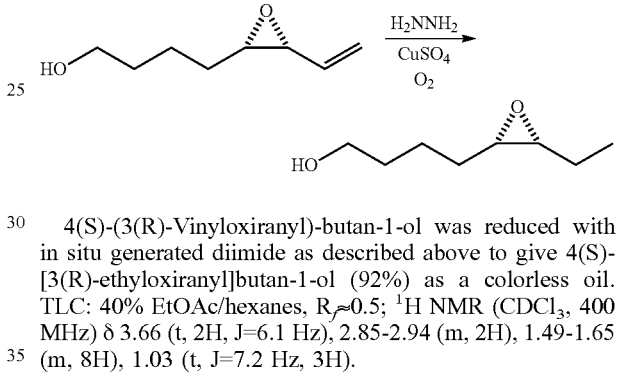

4(S)-(3(R)-Vinyloxiranyl)-butan-1-ol was reduced with in situ generated diimide as described above to give 4(S)-[3(R)-ethyloxiranyl]butan-1-ol (92%) as a colorless oil. TLC: 40% EtOAc/hexanes, R$_f$~0.5; $^1$H NMR (CDCl$_3$, 400 MHz) δ 3.66 (t, 2H, J=6.1 Hz), 2.85-2.94 (m, 2H), 1.49-1.65 (m, 8H), 1.03 (t, J=7.2 Hz, 3H).

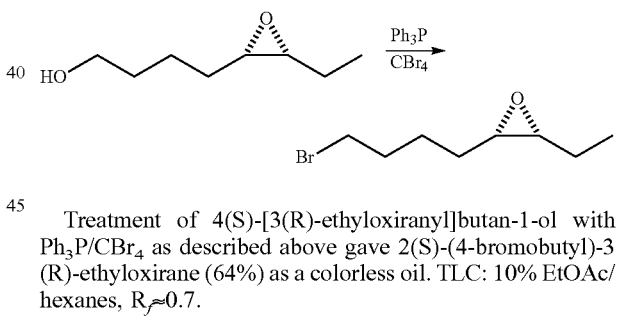

Treatment of 4(S)-[3(R)-ethyloxiranyl]butan-1-ol with Ph$_3$P/CBr$_4$ as described above gave 2(S)-(4-bromobutyl)-3(R)-ethyloxirane (64%) as a colorless oil. TLC: 10% EtOAc/hexanes, R$_f$~0.7.

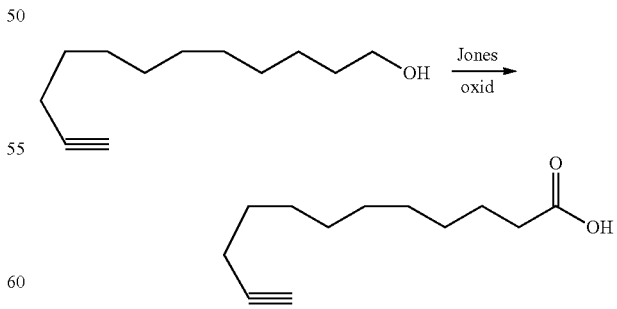

Jones oxidation of dodec-10-yn-1-ol (2.5 g, 13.73 mmol) as described above afforded dodec-11-ynoic acid (2.3 g, 86%). $^1$H NMR (CDCl$_3$, 400 MHz) δ 2.34 (t, 2H, J=7.0 Hz), 2.14-2.21 (m, 2H), 1.93 (t, 1H, J=2.75 Hz), 1.21-1.64 (m, 22H).

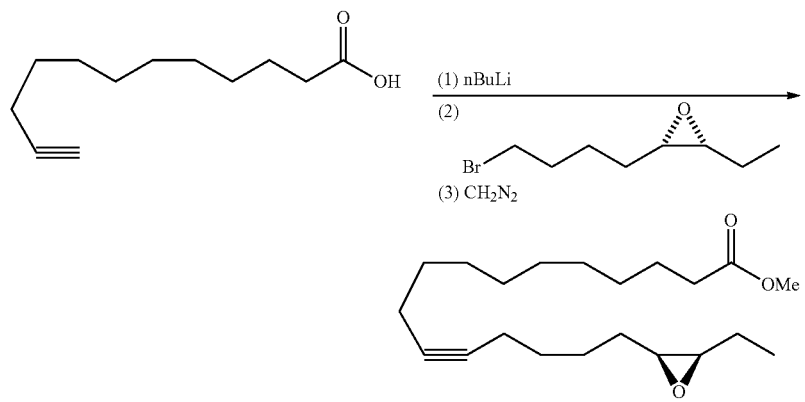

Alkylation of dodec-11-ynoic acid (580 mg) with 2(S)-(4-bromobutyl)-3(R)-ethyloxirane (500 mg) as described above furnished 16(S)-[3(R)-ethyloxiranyl]-hexadec-11-ynoic acid (64%) which was esterified with diazomethane to give methyl 16(S)-[3(R)-ethyloxiranyl]-hexadec-11-ynoate as a colorless oil. TLC: 10% EtOAc/hexanes, $R_f$=0.5; $^1$H NMR (CDCl$_3$, 400 MHz) δ 3.66 (s, 3H), 2.82-2.88 (m, 2H), 2.29 (t, 2H, J=7.3 Hz), 2.10-2.17 (m, 4H), 1.28-1.63 (m, 22H), 1.03 (t, 3H, J=7.1 Hz).

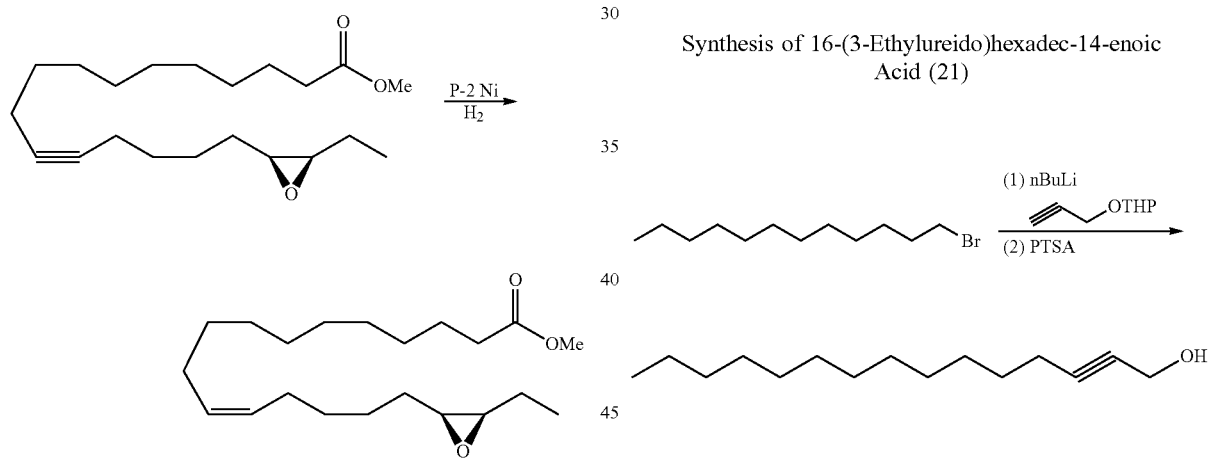

Semi-hydrogenation of methyl 16(S)-[3(R)-ethyloxiranyl]-hexadec-11-ynoate as described above gave methyl 16(S)-[3(R)-ethyloxiranyl]-hexadec-11(Z)-enoate (96%) as a colorless oil. TLC: 10% EtOAc/hexanes, $R_f$=0.55; $^1$H NMR (400 MHz, CDCl$_3$) δ 5.31-5.36 (m, 2H), 3.64 (s, 3H), 2.84-2.91 (m, 2H), 2.28 (t, 2H, J=7.3 Hz), 1.96-2.06 (m, 4H), 1.36-1.61 (m, 6H), 1.21-1.35 (m, 16H), 1.03 (t, 3H, J=7.3 Hz).

Column: Chiracel OJ-H preparative.
Wavelength: 210 nm
Mobil phase: 99.97:0.03 (Hex/IPA)
Flow rate 8 mL/min.
1st. Fraction is: PN-III-191-18. (Acid)
2nd fraction is: PN-III-192-13. (Acid)

Example 16

Synthesis of 16-(3-Ethylureido)hexadec-14-enoic Acid (21)

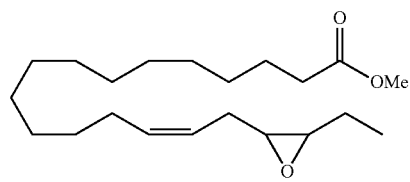 [SMILES: CCC1OC1C/C=C\CCCCCCCCCCCCC(=O)OC]

Alkylation of 2-(prop-2-ynyloxy)tetrahydro-2H-pyran (15.5 g, 110.71 mmol) with 1-bromododecane (34.0 g, 132.04 mmol) as described above gave 2-(pentadec-2-ynyloxy)tetrahydro-2H-pyran (27.2 g, 80%) which was used without further purification. TLC: 10% EtOAc/hexanes, $R_f$=0.5.

Cleavage of the THP ether from crude 2-(pentadec-2-ynyloxy)tetrahydro-2H-pyran (30 g) using PTSA as described above gave pentadec-2-yn-1-ol (18.6 g, 85%) as a colorless oil. TLC: 30% EtOAc/hexanes, $R_f$=0.40; $^1$H NMR (CDCl$_3$, 300 MHz) δ 4.25 (s, 2H), 2.17-2.23 (m, 2H), 1.70 (br s, 1H), 1.40-1.53 (m, 2H), 1.20-1.48 (m, 18H), 0.87 (t, 3H, J=7.3 Hz).

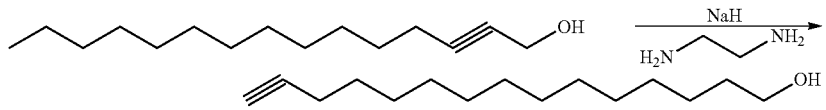

Isomerization of pentadec-2-yn-1-ol (12.5 g, 54.95 mmol) using NaH/ethylenediamine as described above furnished pentadec-14-yn-1-ol (9.4 g, 76%) as a white solid. M.P.: 54.2-54.8° C. TLC: 30% EtOAc/hexanes, $R_f$≈0.45; $^1$H NMR (400 MHz, CDCl$_3$) δ 3.60-3.65 (m, 2H), 2.16 (dt, 2H, J=7.1 Hz, 2.4 Hz), 1.92 (t, 1H, J=2.4 Hz), 1.47-1.60 (m, 4H), 1.22-1.35 (m, 18H).

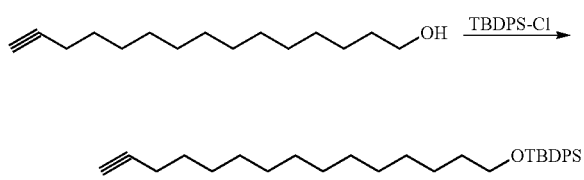

Silylation of pentadec-14-yn-1-ol (8.80 g, 39.28 mmol) using TBDPSCl (12.92 g, 47.14 mmol) as described above gave tert-butyl(pentadec-14-ynyloxy)diphenylsilane (16.7 g, 87%) as a colorless oil. TLC: 6% EtOAc/hexanes, $R_f$≈0.6; $^1$H NMR (CDCl$_3$, 300 MHz) δ 7.65-7.68 (m, 4H), 7.34-7.42 (m, 6H), 3.65 (t, J=7.3 Hz, 2H), 2.15-2.21 (m, 2H), 1.94 (t, J=1.9 Hz, 1H), 1.20-1.60 (m, 22H), 1.04 (s, 9H).

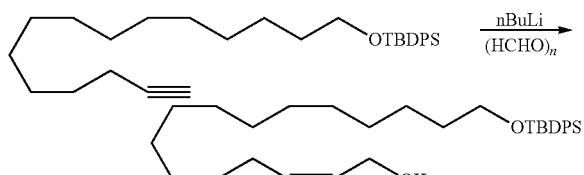

n-BuLi (2.5 M solution in hexanes, 1.29 g, 8 mL, 20.24 mmol) was added to a stirring, −40° C. solution of tert-butyl (pentadec-14-ynyloxy)diphenylsilane (8.5 g, 18.40 mmol) in THF (175 mL) under an argon atmosphere. After 30 min, the reaction mixture was gradually warmed over 3 h to −10° C., held at this temperature for 20 min, then re-cooled to −50° C. Then, a solution of paraformaldehyde (3.05 g, 92.2 mmol) in THF (30 mL) was cannulated into the stirring reaction mixture. After 30 min, the temperature was gradually warmed over 3 h to room temperature. Following 1 h at room temperature, the reaction mixture was quenched with sat. aq. NH$_4$Cl (10 mL), diluted with ether (100 mL), and washed with water (2×75 mL). The combined aqueous washes were back-extracted with ether (2×50 mL). The combined A11 of the organic extracts were combined, dried over Na$_2$SO$_4$, and concentrated under reduced pressure. The residue was purified by SiO$_2$ column chromatography using 5% EtOAc/hexanes as eluent to give 16-(tert-butyldiphenylsilyloxy) hexadec-2-yn-1-ol (6.12 g, 68%). TLC: 30% EtOAc/hexanes, $R_f$≈0.5; $^1$H NMR (CDCl$_3$, 300 MHz) δ 7.70-7.74 (m, 4H), 7.34-7.44 (m, 6H), 4.3 (t, 2H, J=2.1 Hz), 3.65 (t, 2H, J=7.3 Hz), 2.12-2.17 (m, 2H), 1.20-1.61 (m, 22H), 1.04 (s, 9H).

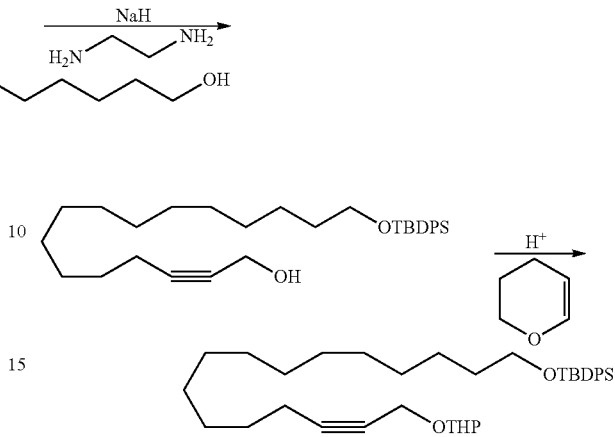

16-(tert-Butyldiphenylsilyloxy) hexadec-2-yn-1-ol (6.0 g, 12.5 mmol) was converted to the corresponding THP ether as described above to give tert-butyldiphenyl(16-(tetrahydro-2H-pyran-2-yloxy)hexadec-14-ynyloxy)silane (6.12 g, 87%). TLC: 10% EtOAc/hexanes, $R_f$≈0.5; $^1$H NMR (CDCl$_3$, 300 MHz) δ 7.70-7.73 (m, 4H), 7.35-7.43 (m, 6H), 4.82 (t, 1H, J=3.1 Hz), 4.16-4.32 (m, 2H), 3.80-3.88 (m, 1H), 3.64 (t, 2H, J=6.6 Hz), 3.50-3.56 (m, 1H), 2.17-2.23 (m, 2H), 1.22-1.81 (m, 28H), 1.05 (s, 9H).

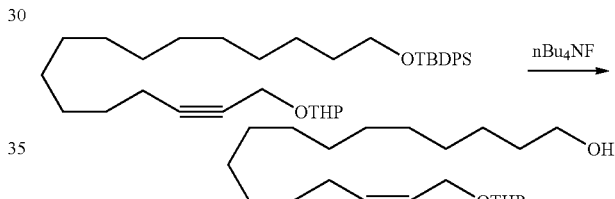

Desilylation of tert-butyldiphenyl (16-(tetrahydro-2H-pyran-2-yloxy) hexadec-14-ynyloxy) silane (6.1 g, 10.6 mmol) as described above furnished 16-(tetrahydro-2H-pyran-2-yloxy) hexadec-14-yn-1-ol (3.26 g, 91%) as a colorless oil. TLC: 40% EtOAc/hexanes, $R_f$≈0.4; 4.83 (t, 1H, J=3.0 Hz), 4.17-4.31 (m, 2H), 3.82-3.87 (m, 1H), 3.66 (t, 2H, J=7.2 Hz), 3.51-3.57 (m, 1H), 2.18-2.24 (m, 2H), 1.20-1.82 (m, 28H).

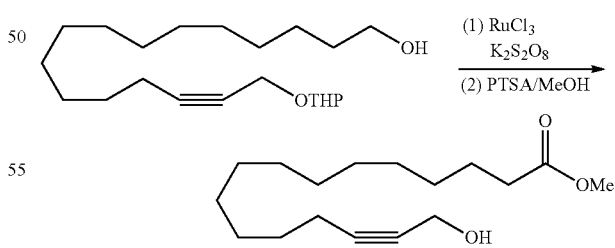

RuCl$_3$ (10 mg) and potassium persulphate (2.8 g, 10.2 mmol) were added to a solution of 16-(tetrahydro-2H-pyran-2-yloxy)hexadec-14-yn-1-ol (1.2 g, 3.55 mmol) in acetonitrile (20 mL). After 10 min, KOH (30 mL of a 2 M soln) was added.

After an additional 3 h, the reaction mixture was neutralized to pH 7, diluted with EtOAc (100 mL), and washed with water (3×75 mL). The combined aqueous extracts were back-extracted with EtOAc (3×75 mL). All of the organic extracts were combined, dried over Na$_2$SO$_4$, and concentrated under reduced pressure. The residue was purified by SiO$_2$ column chromotography using 20% EtOAc/hexanes as eluent to give 16-(tetrahydro-2H-pyran-2-yloxy)hexadec-14-ynoic acid (1.05 g, 91%) as a colorless oil that was used without further purification. TLC: 50% EtOAc/hexanes, R$_f$=0.35. Lit. ref.: R. S. Varma; M. Hogan *Tetrahedron Lett.* 1992: 33, 719.

Concomitant esterification of the carboxylic acid and cleavage of the THP ether in 16-(tetrahydro-2H-pyran-2-yloxy)hexadec-14-ynoic acid (1.0 g, 2.84 mmol) as described above furnished methyl 16-hydroxyhexadec-14-ynoate (665 mg, 83%) as a colorless oil. TLC: 30% EtOAc/hexanes, R$_f$=0.40; $^1$H NMR (CDCl$_3$, 300 MHz) δ 4.22-4.26 (m, 2H), 3.66 (s, 3H), 2.29 (t, 2H, J=7.3 Hz), 2.20 (tt, 2H, J=2.1 Hz, 6.8 Hz), 1.21-1.66 (m, 20H).

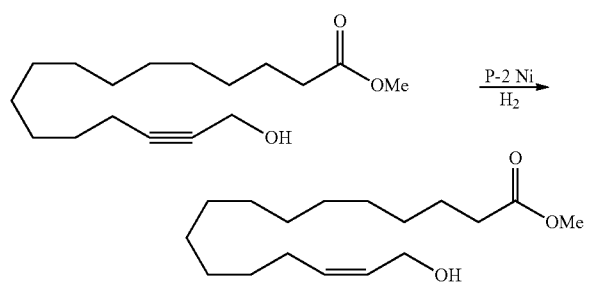

Semi-hydrogenation of methyl 16-hydroxyhexadec-14-ynoate (650 mg, 2.30 mmol) as described above furnished methyl 16-hydroxyhexadec-14(Z)-enoate (640 mg, 98%) as a colorless oil. TLC: 30% EtOAc/hexanes, R$_f$=0.45; $^1$H NMR (CDCl$_3$, 300 MHz) δ 5.49-5.62 (m, 2H), 4.17-4.21 (m, 2H), 3.66 (s, 3H), 2.30 (t, 2H, J=7.6 Hz), 2.02-2.09 (m, 2H), 1.42-1.68 (m, 4H), 1.20-1.41 (m, 16H).

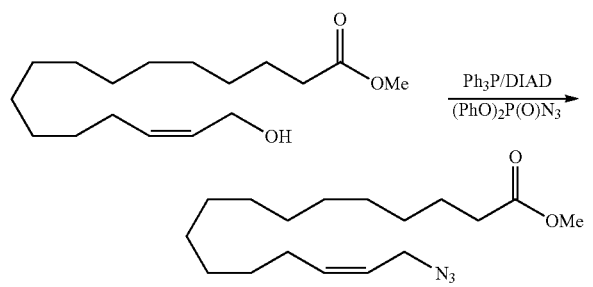

Conversion of methyl 16-hydroxyhexadec-14(Z)-enoate (0.6 g, 2.11 mmol) to the corresponding azide as described above gave methyl 16-azidohexadec-14(Z)-enoate (510 mg, 78%) as white solid. M.P.: 42.5-42.8° C. TLC: 10% EtOAc/hexanes, R$_f$=0.50; $^1$H NMR (CDCl$_3$, 300 MHz) δ 5.66-5.82 (m, 1H), 5.46-5.55 (m, 1H), 3.80 (d, 2H, J=7.4 Hz), 3.66 (s, 3H), 2.30 (t, 2H, J=7.3 Hz), 2.02-2.14 (m, 2H), 1.21-1.40 (m, 20H).

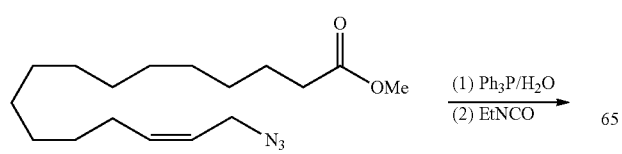

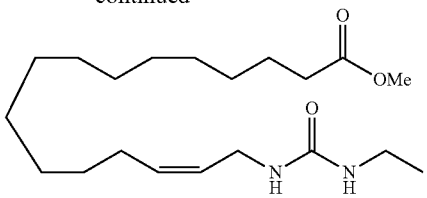

Starting with methyl 16-azidohexadec-14(Z)-enoate (150 mg, 0.48 mmol), the azide was reduced using Ph$_3$P and the resultant amine reacted with ethyl isocyanate as described above to give methyl 16-(3-ethylureido)hexadec-14(Z)-enoate (118 mg, 70% over two steps) as a white solid. M.P.: 63.4-63.6° C. TLC: 50% EtOAc/hexanes, R$_f$=0.30; $^1$H NMR (CDCl$_3$, 300 MHz) δ 5.31-5.52 (m, 2H), 5.08-5.22 (br s, 2H), 3.76 (t, 2H, J=5.2 Hz), 3.63 (s, 3H), 3.15 (q, 2H, J=6.7 Hz), 2.27 (t, 2H, J=7.3 Hz), 1.95-2.04 (m, 2H), 1.54-1.64 (m, 2H), 1.18-1.38 (m, 18H), 1.07 (t, 3H, J=6.9 Hz); $^{13}$C NMR (CDCl$_3$, 75 MHz) δ 174.69, 159.03, 132.91, 126.75, 51.67, 37.67, 35.27, 34.32, 29.81, 29.74, 29.64, 29.50, 29.46, 29.34, 27.57, 25.15, 15.76.

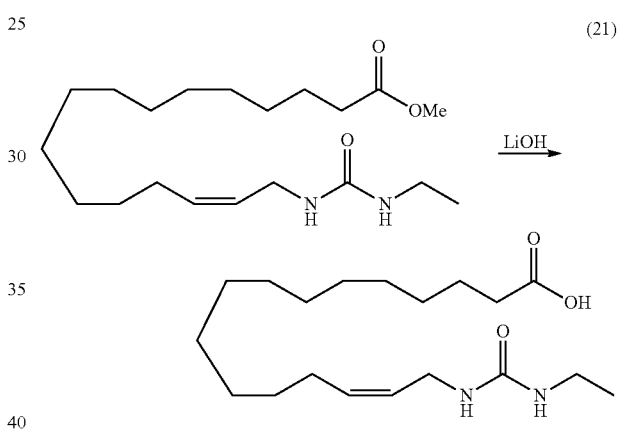

Hydrolysis of methyl 16-(3-ethylureido)hexadec-14(Z)-enoate as described above furnished 16-(3-ethylureido)hexadec-14(Z)-enoic acid (92%) as a white solid. M.P.: 59-60° C. TLC: 75% EtOAc/hexanes, R$_f$=0.30; $^1$H NMR (CD$_3$OD, 300 MHz) δ 5.33-5.56 (m, 2H), 3.74 (d, 2H, J=6.3 Hz), 3.13 (q, 2H, J=7.0 Hz), 2.26 (t, 2H, J=7.2 Hz), 1.98-2.12 (m, 2H), 1.52-1.64 (m, 2H), 1.18-1.38 (m, 18H), 1.06 (t, 3H, J=7.0 Hz); $^{13}$C NMR (CD$_3$OD, 75 MHz) δ 176.69, 159.94, 132.31, 126.57, 36.98, 34.70, 33.96, 29.63, 29.61, 29.54, 29.50, 29.34, 29.26, 29.15, 27.20, 24.98, 14.52.

Example 17

Synthesis of 16-Butyramidohexadec-14(Z)-enoic acid (22)

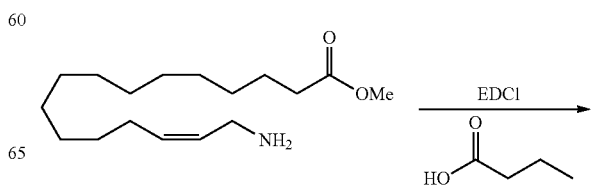

-continued

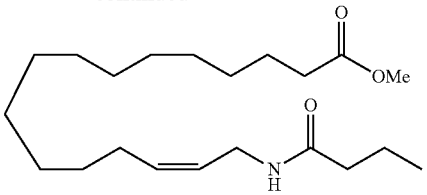

Crude methyl 16-aminohexadec-14(Z)-enoate (crude 150 mg) was condensed with n-butyric acid (48 mg, 0.55 mmol) as described above to give methyl 16-butyramidohexadec-14(Z)-enoate (100 mg, 71%) as a colorless oil. TLC: 50% EtOAc/hexanes, $R_f$≈0.40; $^1$H NMR (CDCl$_3$, 300 MHz) δ 5.28-5.64 (m, 2H), 3.78-3.90 (m, 2H), 3.65 (s, 3H), 2.30 (t, 2H, J=7.2 Hz), 2.14 (t, 2H, J=7.6 Hz), 1.97-2.08 (m, 2H), 1.54-1.65 (m, 4H), 1.20-1.38 (m, 18H), 0.93 (t, 3H, J=7.2 Hz); $^{13}$C NMR (CDCl$_3$, 75 MHz) δ 174.62, 173.18, 134.12, 125.84, 51.67, 41.65, 38.94, 38.88, 36.82, 34.32, 32.45, 29.79, 29.72, 29.65, 29.46, 29.36, 27.58, 25.16, 19.40, 13.99.

-continued

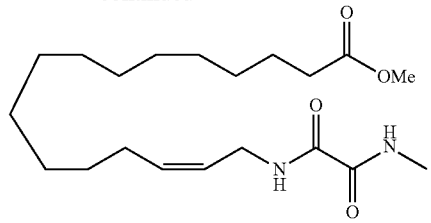

Condensation of methyl 16-aminohexadec-14(Z)-enoate (crude 140 mg) with 2-(methylamino)-2-oxoacetic acid (54 mg, 0.52 mmol) as described above gave methyl 16-(2-(methylamino)-2-oxoacetamido)hexadec-14(Z)-enoate (92 mg, 72%) as a white solid. M.P.: 104.5-1.4.8° C. TLC: 75% EtOAc/hexanes, $R_f$≤0.40. $^1$H NMR (CDCl$_3$, 300 MHz) δ δ 7.80 (br s, 2H), 5.32-5.71 (m, 2H), 3.82-3.96 (m, 2H), 3.62 (s, 3H), 2.82 (s, 3H), 2.28 (t, 3H, J=7.1 Hz), 1.93-2.08 (m, 2H), 1.56-1.64 (m, 2H), 1.22-1.36 (m, 18).

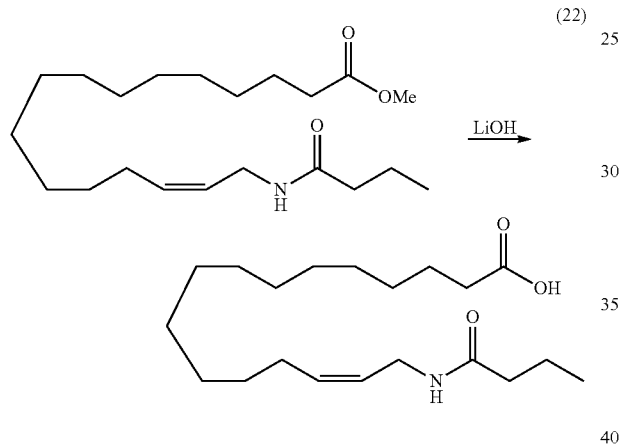

Hydrolysis of methyl 16-butyramidohexadec-14(Z)-enoate (96 mg, 0.27 mmol) as described above gave 16-butyramidohexadec-14(Z)-enoic acid (82 mg, 91%) as a white solid. M.P.: 72.7-73.1° C. TLC: 75% EtOAc/hexanes, $R_f$≈0.40; $^1$H NMR (CDCl$_3$, 300 MHz) δ 5.28-5.70 (m, 4H), 3.76-3.90 (m, 2H), 2.31 (t, 2H, J=7.4 Hz), 2.15 (t, 2H, J=6.9 Hz), 1.97-2.18 (m, 2H), 1.56-1.68 (m, 4H), 1.20-1.40 (m, 18H), 0.92 (t, 3H, J=7.3 Hz); $^{13}$C NMR (CDCl$_3$, 75 MHz) δ 179.27, 173.58, 134.23, 125.66, 41.75, 38.86, 38.80, 36.91, 34.37, 32.44, 29.76, 29.70, 29.66, 29.62, 29.44, 29.37, 29.29, 24.98, 19.42, 13.98.

Hydrolysis of methyl 16-(2-(methylamino)-2-oxoacetamido)hexadec-14(Z)-enoate (75 mg, 0.20 mmol) as described above gave 16-(2-(methylamino)-2-oxoacetamido)hexadec-14(Z)-enoic acid (63 mg, 88%) as a white solid. 118.9-119.3° C. TLC: 100% EtOAc, $R_f$≈0.30; $^1$H NMR (CDCl$_3$, 300 MHz) δ 5.12-5.47 (m, 2H), 3.58-3.72 (m, 2H), 2.66 (s, 3H), 2.05 (t, 3H, J=7.2 Hz), 1.76-1.86 (m, 2H), 0.99-1.41 (m, 20H). $^{13}$C NMR (CDCl$_3$, 75 MHz) δ 182.04, 163.77, 160.03, 134.06, 124.53, 41.28, 36.54, 34.11, 32.22, 29.62, 29.50, 29.35, 29.17, 29.08, 27.33, 27.56, 25.03.

Example 18

Synthesis of 16-(2-(Methylamino)-2-oxoacetamido)hexadec-14(Z)-enoic acid (23)

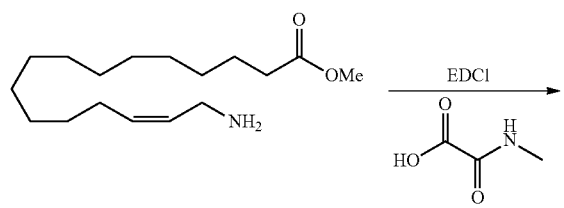

Example 19

Identification of Agonists

This example shows the identification of compounds which act as agonists of EPA and 17,18-EETeTr and thus mimic the physiological effects of n-3 PUFAs and their CYP-dependent omega-3 epoxy-metabolites. The agonistic effects determined in this example consist in a reduction of the spontaneous beating rate of cultured neonatal rat cardiomyocytes (NRCMs). This negative chronotropic effect reflects the capacity of the analogs to interact with and to activate a G-protein coupled receptor or other primary cellular targets that reduce the contractility of cardiomyocytes under basal and stress-induced conditions.

Materials and Methods

The structures of all compounds tested are given in FIG. 1. The compounds included EPA and 17,18-EETeTr (compounds 01 and 02; purchased from Cayman Chemical) as well as all but one (compound 16) of the analogs synthesized as described in examples 1-24. The R,S- and S,R-enantiomers of 17,18-EETeTr (compounds 03 and 04) were prepared resolving the racemic mixture (compound 02) by means of chiral-phase HPLC as described previously (Barbosa-Sicard E, Markovic M, Honeck H, Christ B, Muller D N, Schunck W H. Biochem Biophys Res Commun. 2005 Apr. 22; 329(4):1275-81). Before use, the compounds to be tested were prepared as 1000-fold stock solutions in ethanol.

Isolation and cultivation of NRCMs were performed as described previously (Wallukat, G; Wollenberger, A. *Biomed Biochim Acta*. 1987; 78:634-639; Wallukat G, Homuth V, Fischer T, Lindschau C, Horstkamp B, Jupner A, Baur E, Nissen E, Vetter K, Neichel D, Dudenhausen J W, Haller H, Luft F C. *J Clin Invest*. 1999; 103: 945-952). Briefly, neonatal Wistar rats (1-2 days old) were killed in conformity to the recommendations of the Community of Health Service of the City of Berlin and the cardiomyocytes were dissociated from the minced ventricles with a 0.2% solution of crude trypsin. The isolated cells were then cultured as monolayers on the bottom (12.5 cm$^2$) of Falcon flasks in 2.5 ml of Halle SM 20-I medium equilibrated with humidified air. The medium contained 10% heat-inactivated FCS and 2 µmol/l fluoro-deoxyuridine (Serva, Heidelberg, Germany), the latter to prevent proliferation of non-muscle cells. The NRCMs (2.4×10$^6$ cells/flask) were cultured at 37° C. in an incubator. After 5 to 7 days, the NRCMs formed spontaneously beating cell clusters. The cells in each cluster showed synchronized contraction with a beating rate of 120 to 140 beats per minute. On the day of the experiment, the culture medium was replaced by 2.0 ml fresh serum-containing medium. Two hours later, the beating rates were monitored at 37° C. using an inverted microscope equipped with a heating stage. To determine the basal rate, 6 to 8 individual clusters were selected and the number of contractions was counted for 15 sec. After that, the compound to be tested was added to the culture and the beating rate of the same clusters was monitored 5 min later again. Based on the difference between the basal and compound-induced beating rate of the individual clusters, the chronotropic effects (Δ beats/min) were calculated and are given as mean±SE values. N refers to the number of clusters monitored which originated, in general, from at least three independent NRCM cultures.

Results

The results of these experiments are presented in FIG. 1. Addition of EPA (C01) in concentrations above 1 µM to the NRCM cultures resulted in a progressive reduction of the beating rate. This effect was fully expressed using an EPA concentration of 3.3 µM and an incubation time of 30 min. In contrast, 17,18-EETeTr (C02) produced the same effect almost immediately and already in the low nanomolar range (EC50 of 1-2 nM, data not shown). To compare the activity of 17,18-EETeTr with that of its synthetic analogs, all these compounds were tested at a final concentration of 30 nM and using an incubation time of 5 min. Under the same conditions, the vehicle control (0.1% ethanol) showed no effect on the spontaneous beating rate.

As summarized in FIG. 1, various synthetic analogs showed a negative chronotropic effect similar to that of EPA and 17,18-EETeTr. These analogs are therefore designated as agonists. Agonists included:
(i) analogs containing a double bond in 11,12-position in combination with an epoxy-group in 17,18-position, whereby the epoxy-group is racemic or in R,S-configuration (C03, C2, C4 and C9)
(ii) analogs containing an 11,12-double bond in combination with a suitable substitute of the 17,18-epoxy-group (C11, C13 and C24)
(iii) analogs belonging to category ii but modified at the carboxy-group (C17 and C18)

In contrast, most of the analogs not carrying an 11,12-double bond showed no significant agonistic effects (i.e. their addition altered the beating rate of NRCMs by less than 5 beats per min). To this group belong C1, C3, C5, C6, C7, C8, C19 and C23. A shift of the double bond from the 11,12- to 14,15-position abolished the agonistic properties of some compounds; compare C9-C5 and C11-C23. Moreover, with some compounds the same shift of the double bond inversed the effect from a negative to positive chronotropic response of the NRCMs (compare C11-C21) or conferred a positive chronotropic effect to a compound that was largely inactive (compare C12 and C22).

A comparison of the effects of compounds C03-C04 shows that the 17,18-epoxy-group conferred agonistic properties if present in the R,S-configuration whereas the corresponding S,R-enantiomer was inactive. The respective racemic mixture (C02) acted as agonist indicating that the effect of the R,S-enantiomer was predominating. Exactly the same stereochemical conditions applied to the 17,18-EETeTr analogs which carry only one double-bond in 11,12-position: the racemate (C4) and the R,S-enantiomer (C9) exerted agonistic effects and the S,R-enantiomer was inactive. In contrast, the analog containing only one double bond in 14,15-position showed no effect as racemate (C5) and S,R-enantiomer (C19) but an agonistic effect as R,S-enantiomer (C20). Thus, in this case the agonistic effect of the R,S-enantiomer was abolished when the S,R-enantiomer was simultaneously present.

The effects of compounds C11, C13 and C24 demonstrate that the 17,18-epoxy-group can be replaced by residues carrying a suitable oxygen-functionality. These types of substitution did not only maintain (C24) but even significantly increased the agonistic effect: $p<0.05$ for the comparisons of the agonistic effects between C11 (−27.0±1.2; n=27) or C13 (−33.7±1.3; n=24) with 17,18-EETeTr (−22.5±0.8; n=60) and C4 (−18.3±1.5; n=21).

Example 20

Identification of Antagonists

This example shows the identification of compounds that act as antagonists of EPA and 17,18-EETeTr and thus block the physiological effects of n-3 PUFAs and their CYP-dependent omega-3 epoxy-metabolites. These antagonists were selected based on their capacity to abolish the negative chronotropic effects of EPA, 17,18-EETeTr and their synthetic agonists on the contractility of neonatal rat cardiomyocytes.

Materials and Methods

Figure 2:
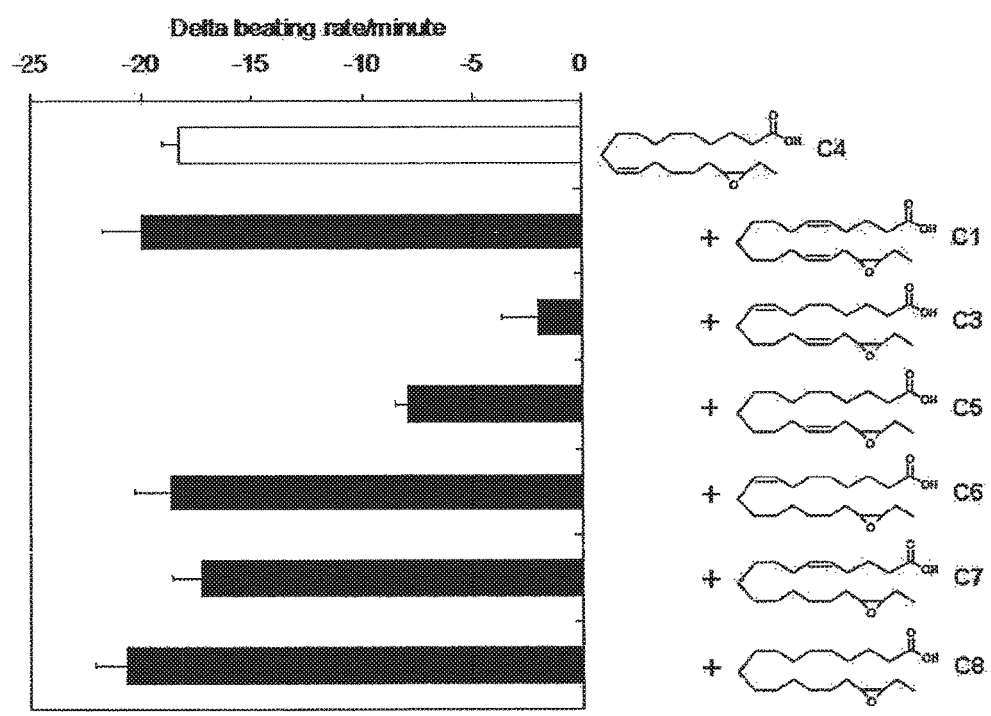
FIG. 2 shows the structures and chronotropic effects of compounds tested as potential antagonists of EPA and 17,18-EETeTr.

The structures of the compounds tested are presented in FIG. 2. Potential antagonists included compounds C1, C3, C5, C6, C7, and C8, which were synthesized as described above in the corresponding examples.

The bioassay was performed with NRCMs as described in example 25. In the first series of experiments, compound C4 was used as the agonist and its effect was determined after preincubating the cultured NRCMc for 5 min with one of the potential antagonists. Both C4 and the potential antagonist were used at a final concentration of 30 nM. In the second series of experiments, compound C3 (30 nM) was tested for its antagonistic effect against EPA (3.3 µM) and 17,18-EETeTr (30 nM) as well as against the agonistic analogs C2, C4 and C13 (30 nM each).

Results

Figure 3:
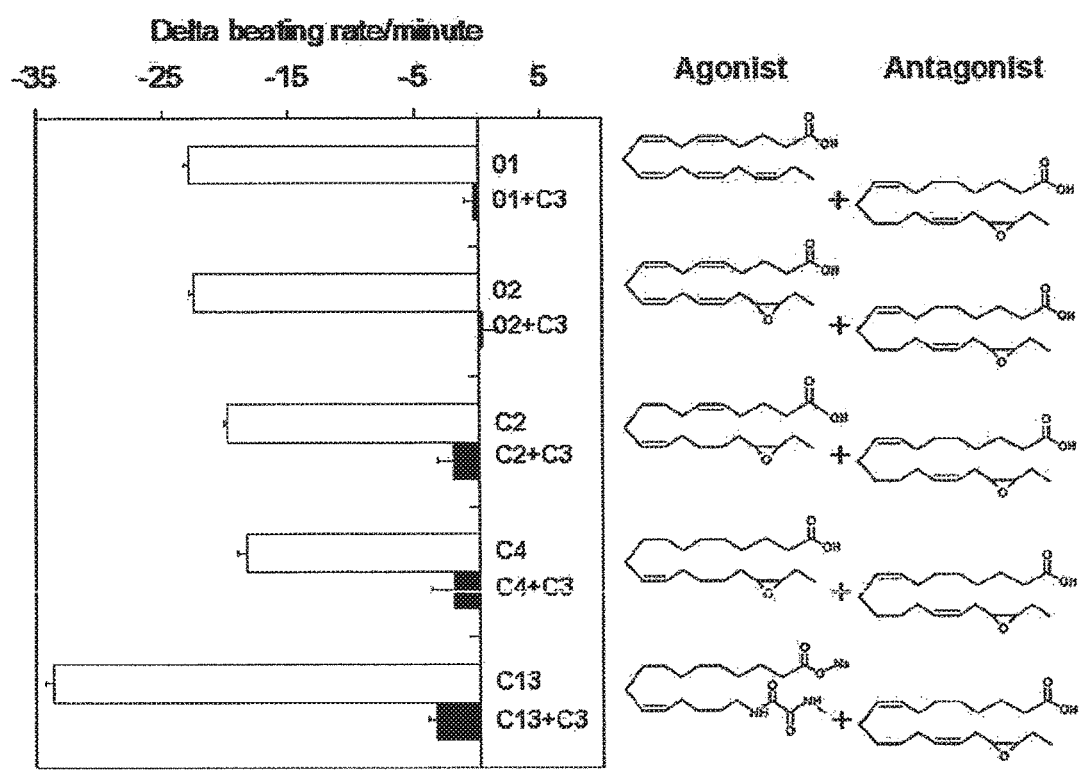
FIG. 3 shows that compound C3 is a highly potent antagonist not only of C4 but also of EPA, 17,18-EETeTr, C2 and C13.

The results are presented in FIGS. 2 and 3. The data summarized in FIG. 2 show that the agonistic effect of compound C4 was significantly inhibited by compounds C3 and C5. This antagonistic capacity of C3 and C5 became only obvious in combination with the agonist since both compounds did not exert any significant effect when added alone to the cultured NRCMs (compare example 25, FIG. 1). The other compounds (C1, C6, C7 and C8) did not inhibit the agonistic effect of C4 (FIG. 2) and were also inactive when tested alone (compare example 25, FIG. 1). The structural feature which distinguishes the active antagonists (C3 and C5) from the completely inactive analogs (C1, C6, C7 and C8) consisted in the presence of a 14,15-double bond.

The data summarized in FIG. 3 show that compound C3 is a highly potent antagonist not only of C4 but also of EPA, 17,18-EETeTr, C2 and C13. At a concentration of 30 nM, C3 abolished the negative chronotropic effect of EPA which was applied at a concentration of 3.3 µM. Even the effect of the most potent agonist (C13) was almost completely blocked by C3 when both analogs were present in equimolar concentrations (30 nM).

Example 21

EPA and its Agonistic Analogs Act Via the Same Cellular Mechanisms

This example shows that EPA, 17,18-EETeTr and their most potent synthetic agonist (C13) share the same mechanism of cellular action as judged by identical responses to several pharmacological interventions.

Materials and Methods

The bioassay with NRCMs was performed as described in examples 25 and 26. Compounds used as putative inhibitors of agonistic effects were: 11,12-epoxyeicosatrienoic acid (11,12-EET from Cayman Chemicals; used at a final concentration of 30 nM), AH6089 (unspecific antagonist of EP2 and related prostanoid receptors from Cayman Chemical; used at a final concentration of 10 µM), calphostin C (PKC-epsilon inhibitor from Sigma-Aldrich; used at a final concentration of 100 nM), and H89 (PKA-inhibitor from Sigma-Aldrich; used at a final concentration of 1 µM). The cultured NRCMs were preincubated without or with one of the compounds indicated in FIG. 4 for 5 min before the effect of the following agonists was determined: EPA (3.3 µM), 17,18-EETeTr (30 nM) or C13 (30 nM). In some experiments, the NRCMs were stimulated with a selective EP2 prostanoid receptor agonist (butaprost from Sigma-Aldrich; used at a final concentration of 100 nM) to provide a control for the effect of certain inhibitors.

Results

Figure 4:
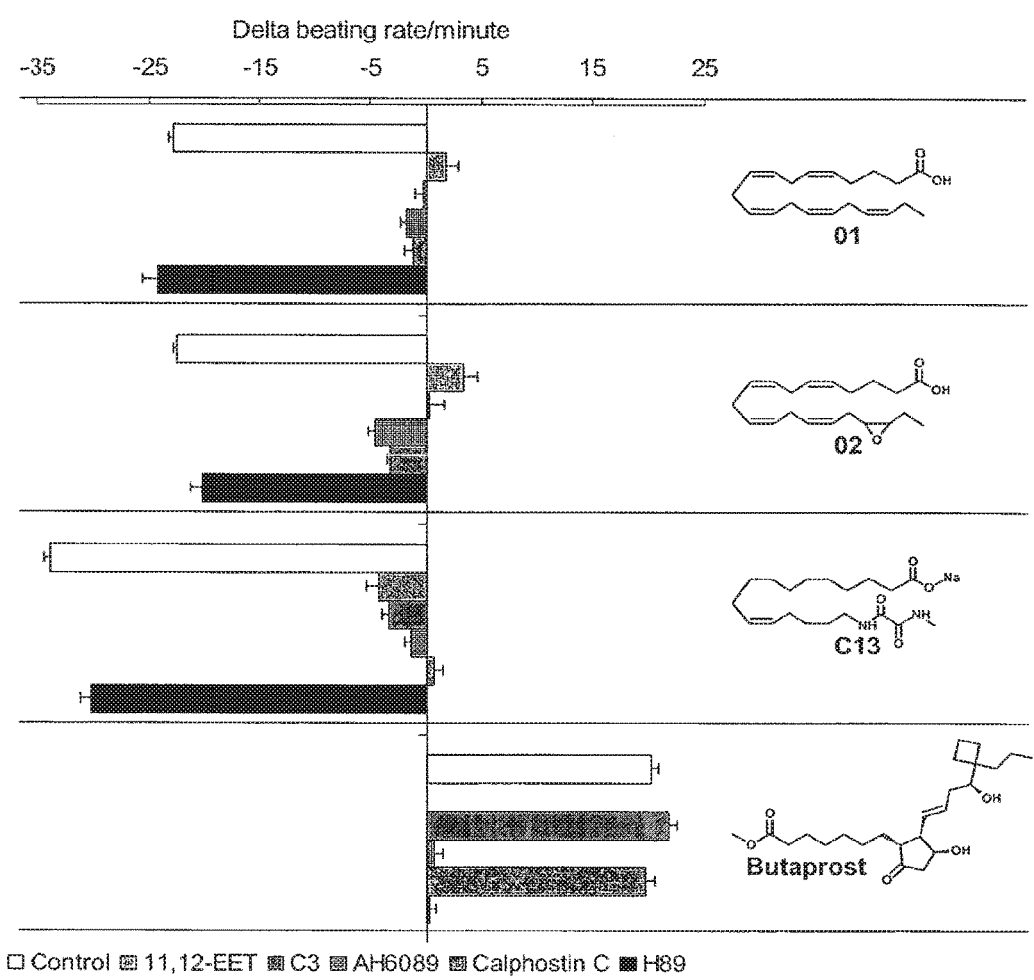
FIG. 4 shows the negative chronotropic effects of EPA (01), 17,18-EETeTr (02) and of the synthetic agonist C13 are blocked by 11,12-EET, compound C3, AH6089 (unselective prostanoid receptor antagonist) and calphostin C (PKC-inhibitor) but not by H89 (PKA inhibitor). The positive chronotropic effect of butaprost (EP2 agonist) is blocked by AH6089 and H89 but not by C3 and caplphostin C.

The results are presented in FIG. 4. The negative chronotropic effects of EPA, 17,18-EETeTr and compound C13 were strongly inhibited by 11,12-EET, C3, AH6089 and calphostin C but were not affected by H89. These results show that EPA, 17,18-EETeTr and their most potent synthetic analog share the same inhibitory profile and thus confirm that these compounds exert their biological effect via identical cellular mechanisms. More specifically, the results indicate that the three agonists compete with 11,12-EET, C3 and AH6089 for binding and activation of the same primary target (the putative omega-3 epoxyeicosanoid receptor) and that the subsequent signaling pathway includes the activation of a protein kinase C isoform as essential component. In contrast, to EPA, 17,18-EETeTr and C3, butaprost exerted a positive chronotropic effect. The butaprost effect was blocked by AH6089 and H89 but not by C3 and calphostin C. Thus, both the primary target of butaprost (EP2 receptor) and the butaprost-induced signaling pathway (involvement of PKA instead of PKC) are different from that of EPA, 17,18-EETeTr and their synthetic analog.

FIG. 4: The negative chronotropic effects of EPA (01), 17,18-EETeTr (02) and of the synthetic agonist C13 are blocked by 11,12-EET, compound C3, AH6089 (unselective prostanoid receptor antagonist) and calphostin C (PKC-inhibitor) but not by H89 (PKA inhibitor). The positive chronotropic effect of butaprost (EP2 agonist) is blocked by AH6089 and H89 but not by C3 and caplphostin C.

Example 22

17,18-EETeTr Agonists Protect Against Calcium Overload and β-Adrenergic Stimulation This example shows that stress-induced responses of cardiomyocytes such as to increased extracellular $Ca^{2+}$-concentrations or to β-adrenergic stimulation are suppressed by the 17,18-EETeTr agonist C11.

Materials and Methods

Compound C11 was synthesized as described above (example 11). NRCMs were isolated and cultured as in Example 19. The basal $Ca^{2+}$-concentration of the medium was 1.2 mM. Increased extracellular $Ca^{2+}$-concentrations (2.2, 5.2 and 8.2 mM) were adjusted by adding appropriate amounts of a 1 M $CaCl_2$ solution to the cultures. Isoproterenol (from Sigma-Aldrich) was used as β-adrenoreceptor agonist and added to the cultures to give final concentrations of 0.1, 1 or 10 µM. C11 was used at a final concentration of 30 nM and added to the cultures 5 min before changing the $Ca^{2+}$-concentration or adding isoproterenol. Controls were performed in the absence of C11.

Results

Figure 5A:
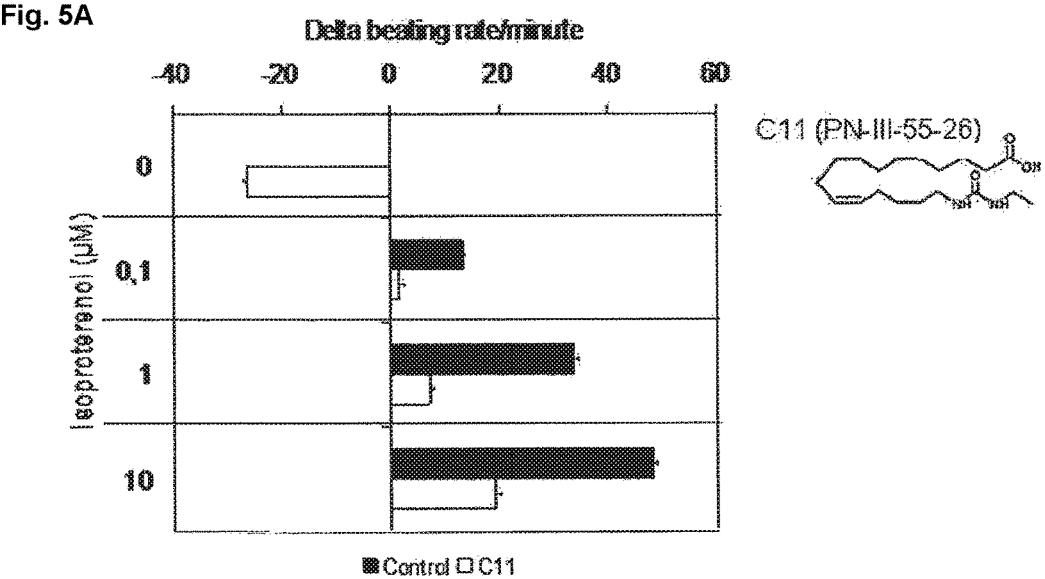
FIGS. 5A, B show the synthetic agonist C11 suppresses the response of NRCMs to β-adrenergic stimulation (isoptroterenol, FIG. 5A) and increased extracellular $Ca^{2+}$-concentrations (FIG. 5B).
Figure 5B:
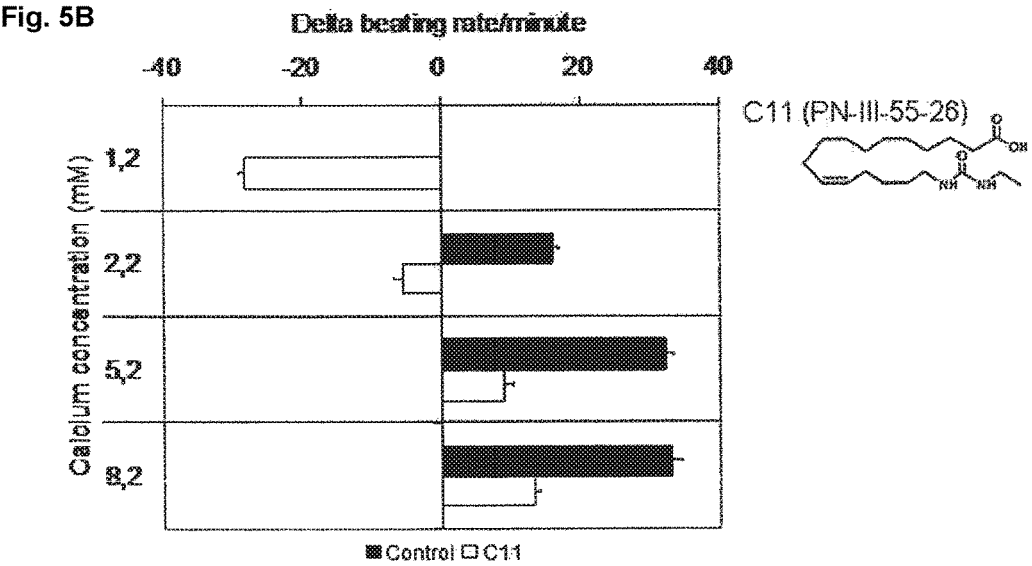

The results are presented in FIG. 5. In control experiments, the NRCMs responded to enhanced extracellular $Ca^{2+}$-concentrations with massively increased beating rates. Preincubation with C11 significantly reduced the beating rate of NRCMs not only under basal conditions (1.2 mM $Ca^{2+}$) but also at higher $Ca^{2+}$-concentrations up to 8.2 mM (FIG. 5A). Similarly, C11 reduced the response to increasing concentrations of isoproterenol which acts as an adrenoreceptor agonist and thereby enhances the contractility and beating rate of NRCMs (FIG. 5B).

FIG. 5: The synthetic agonist C11 suppresses the response of NRCMs to β-adrenergic stimulation (isoptroterenol, FIG. 5A) and increased extracellular $Ca^{2+}$-concentrations (FIG. 5B).

Example 23

Anti-Arrhythmic Effect of 17,18-EETeTr Agonists Under In Vivo Conditions

This example shows that the agonistic analog C17 ameliorates arrhythmias as induced by myocardial infarction.

Materials and Methods

Study design: To gain insight into the in-vivo effects of synthetic 17,18-EETeTr-agonists, myocardial infarction studies were performed in male Wistar rats. Briefly, rats weighing 220-250 g were randomized to receive an i.v. bolus of compound C17 (100 μg in 300 μl 0.9% NaCl) or only 300 μl 0.9% NaCl as vehicle control two hours before induction of myocardial infarction. For safe bolus application, animals were mildly anesthetized using isoflorane. Two hours after bolus application, animals were re-anesthetized with a mixture of ketamine and xylazine (i.v.). Continuous monitoring of the surface-ECG was started (EPTracer, Netherlands) and maintained until the end of the study. After recording of the basal ECG, myocardial infarction was induced by ligation of the left anterior descending artery (LAD). One hour after myocardial infarction animals were sacrificed and organ harvested. Samples from urine, blood, liver, kidney and heart were stored for further analysis.

Method of arrhythmia analysis: Ventricular tachycardia burden was calculated as the sum of all arrhythmic events originating from the ventricular myocardium, which were observed within the first hour after induction of myocardial infarction. In order to quantify not only the frequency but also the severity of the ventricular arrhythmias, an arrhythmia-severity-score was calculated. This score was calculated as the sum of the number of different arrhythmia events (PVC, couplet, triplet, VT<1.5 sec, VT>=1.5 sec), each class factorized by an increasing severity index of 1-5 (e.g. PVC×1, couplets×2, . . . , VT>=1.5 sec×5).

Results

Figure 6A:
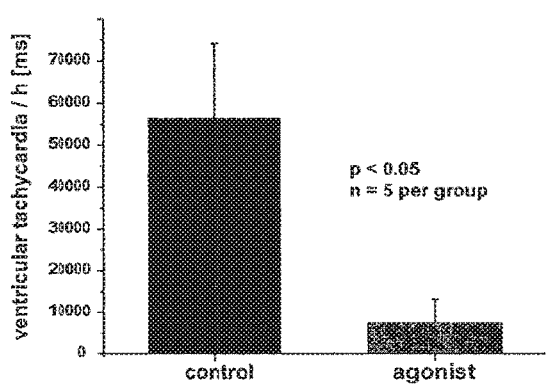
FIGS. 6A, B show treatment with compound C17, a synthetic agonist of 17, 18-EETeTr, ameliorates the frequency (FIG. 6A) and severity (FIG. 6B) of cardiac arrhythmias in a rat model of myocardial infarction.
Figure 6B:
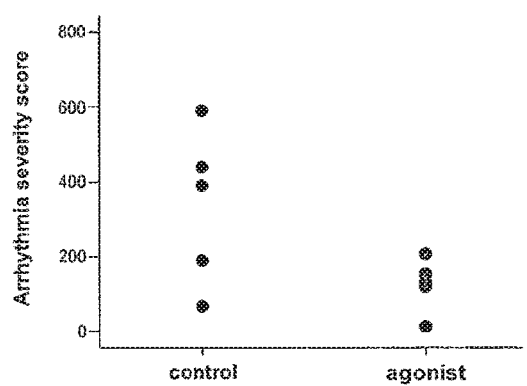

The results are presented in FIG. 6. Bolus injection of the synthetic 17,18-EETeTr agonist (compound C17) did not induce any obvious negative side effects. Ventricular arrhythmias occurred after coronary artery ligation and were observed as single premature ventricular contractions (PVC), short runs of non-sustained ventricular tachycardia (VT) and ventricular tachycardia/fibrillation. Rats treated with the synthetic 17,18-EETeTr-agonist showed a significantly reduced ventricular tachycardia burden compared to controls (7526.2±5664.3 vs. 56377.4±17749.9 ms/h, p<0.05, n=5 per group); FIG. 6A. Moreover, the arrhythmia severity score was lower (125±25 vs. 336±93 arbitrary units, n=5 per group) in the 17,18-EETeTr-agonist group; FIG. 6B.

FIG. 6: Treatment with compound C17, a synthetic agonist of 17,18-EETeTr, ameliorates the frequency (A) and severity (B) of cardiac arrhythmias in a rat model of myocardial infarction.

The invention claimed is:

1. A compound of the general formula (I):

(I)

or a pharmacologically acceptable salt, solvate, hydrate or a pharmacologically acceptable formulation thereof, wherein $R^1$ is selected from —CH$_2$OH; —CH$_2$OAc; —CHO;

—NHSO$_2$-alkyl;

-continued

—NO$_2$;

—SO$_2$NH$_2$; or $R^2$ is hydroxy, heteroalkyl, alkoxy, polyalkoxyalkyl, $NR^3R^4$, $(NHS(O)_2$-m-$(C_6H_4)N_3$, or $Xaa_o$;

$R^3$ and $R^4$ are each and independently of each other selected from hydrogen atom, hydroxy, alkyl, heteroalkyl, cycloalkyl, alkylcycloalkyl, heteroalkylcycloalkyl, aralkyl, or heteroaralkyl;

Xaa is Gly, a conventional D, L-, D- or L-amino acid, a non-conventional D, L-, D- or L-amino acid, or a 2- to 10-mer peptide, wherein Xaa is joined to —C(O) by an amide bond;

o is an integer selected from 1 to 10;

B is CH$_2$, O, or S;

m is an integer from 1 to 3;

T, and W are each and independently of each other selected from —CH$_2$CH$_2$—, and cis or trans —CH=CH— and U is —CH$_2$CH$_2$—;

V is cis or trans —CH=CH—;

X is absent or selected from CH$_2$, and NR$^5$;

Z is selected from CH$_2$, and NR$^{5'}$;

$R^5$ and $R^{5'}$ are each and independently of each other selected from a hydrogen atom, a hydroxy, alkyl, cycloalkyl, alkylcycloalkyl, heteroalkylcycloalkyl, aralkyl, heteroaralkyl group;

Y is —C(O)—, —C(O)—C(O)—, —O—, or —S—; and n is an integer from 0 to 6.

2. The compound according to claim 1, wherein $R^1$ is —COR$^2$.

3. The compound according to claim 1 wherein m is 1.

4. The compound according to claim 1, wherein n is 0 or 1.

5. The compound according to claim 1, wherein each of T, U and W is —CH$_2$CH$_2$—.

6. The compound according to claim 1, wherein Y is —C(O)— or —C(O)—C(O)—.

7. The compound according to claim 1, wherein X is NR$^5$ with R$^5$ being a hydrogen atom, a methyl, ethyl, propyl or iso-propyl group.

8. The compound according to claim 1, wherein Z is NR$^{5'}$ with R$^{5'}$ being a hydrogen atom, a methyl, ethyl, propyl or iso-propyl group.

9. A pharmaceutical composition that comprises at least one compound according to claim 1 and, optionally, a carrier substance and/or an adjuvant.

10. A method for treatment of conditions and diseases associated with inflammation, hypertension, coagulation, immune function, heart failure and cardiac damage comprising administering to a patient in need thereof the pharmaceutical composition of claim 9 in a treatment of conditions and diseases associated with inflammation, hypertension, coagulation, cardiac damage or immune function effective amount.

11. The method of claim 10, wherein the conditions and diseases are associated with cardiac damage.

12. The method of claim 10, wherein the conditions and diseases associated with inflammation, hypertension, coagulation, immune function, heart failure and cardiac damage is cardiac arrhythmia.

13. The method of claim 10, wherein the pharmaceutical composition is administered prophylactically.

* * * * *